(12) United States Patent
Ward et al.

(10) Patent No.: US 12,728,192 B2
(45) Date of Patent: Sep. 8, 2026

(54) FLUID DRAINAGE OR DELIVERY DEVICE FOR TREATMENT SITE

(71) Applicant: AROA BIOSURGERY LIMITED, Auckland (NZ)

(72) Inventors: Brian Roderick Ward, Pukekohe (NZ); Isaac Tristram Tane Mason, Auckland (NZ); Hamish Joshua Rose, Auckland (NZ); Alister Todd Jowsey, Auckland (NZ); Michael Andrew Loveland, Auckland (NZ); Liam Joseph Douglas, Auckland (NZ); Samuel Barry Turner, Auckland (NZ); Dorrin Asefi, Auckland (NZ); Sean James Gorman, Auckland (NZ); Henry David Chittock, Auckland (NZ)

(73) Assignee: AROA BIOSURGERY LIMITED, Auckland (NZ)

( * ) Notice: Subject to any disclaimer, the term of this patent is extended or adjusted under 35 U.S.C. 154(b) by 604 days.

(21) Appl. No.: 18/038,360

(22) PCT Filed: Nov. 24, 2021

(86) PCT No.: PCT/NZ2021/050206
§ 371 (c)(1),
(2) Date: May 23, 2023

(87) PCT Pub. No.: WO2022/114966
PCT Pub. Date: Jun. 2, 2022

(65) Prior Publication Data

US 2024/0001022 A1 Jan. 4, 2024

Related U.S. Application Data

(60) Provisional application No. 63/279,915, filed on Nov. 16, 2021, provisional application No. 63/217,889,
(Continued)

(51) Int. Cl.
*A61M 1/00* (2006.01)

(52) U.S. Cl.
CPC .............. *A61M 1/90* (2021.05); *A61M 1/915* (2021.05); *A61M 1/92* (2021.05)

(58) Field of Classification Search
CPC .......... A61M 1/90; A61M 1/915; A61M 1/92; A61M 1/94; A61M 2205/331;
(Continued)

(56) References Cited

U.S. PATENT DOCUMENTS

| | | | |
|---|---|---|---|
| 5,088,483 | A | 2/1992 | Heinecke |
| 5,180,375 | A | 1/1993 | Feibus |

(Continued)

FOREIGN PATENT DOCUMENTS

| | | | |
|---|---|---|---|
| AU | 2015210406 | A1 | 9/2015 |
| DE | 202019102362 | U1 | 7/2020 |

(Continued)

OTHER PUBLICATIONS

International Preliminary Report on Patentability, PCT/NZ2021/050205, dated May 30, 2023, 11 pages.

(Continued)

*Primary Examiner* — Theodore J Stigell
(74) *Attorney, Agent, or Firm* — Nelson Mullins Riley & Scarborough LLP; Jane E. Remillard, Esq.; Jeanne M. DiGiorgio

(57) ABSTRACT

A bioresorbable device for implantation in the body of a patient for administering fluid and/or negative pressure to a treatment site. The device includes a bioresorbable resilient truss for holding two tissue surfaces spaced apart. The truss has two flexible elongate wall members wound in a manner to define a channel, the two elongate wall members intersecting each other periodically at a plurality of cross-over nodes. The truss also includes at least two flexible elongate
(Continued)

bracing members, each bracing member being mechanically linked to the two elongate wall members at a plurality of the cross-over nodes.

36 Claims, 47 Drawing Sheets

Related U.S. Application Data filed on Jul. 2, 2021, provisional application No. 63/117,995, filed on Nov. 24, 2020.

(58) Field of Classification Search
CPC .. A61M 2205/3313; A61M 2205/3344; A61M 2205/3351; A61M 1/95; A61M 2205/7536; A61M 2206/10; A61M 1/96; A61M 1/964; A61M 1/966; A61M 1/98; A61M 1/916; A61M 1/74; A61M 2205/0216; A61M 2205/04; A61M 27/00; A61M 2205/7518; A61F 13/05; A61L 31/005; A61L 31/146; A61L 31/148; A61L 2430/40
See application file for complete search history.

(56) References Cited

U.S. PATENT DOCUMENTS 5,843,168 A * 12/1998 Dang ........................ A61F 2/88 606/198
6,159,187 A 12/2000 Park et al.
7,883,494 B2 2/2011 Martin
8,403,913 B2 3/2013 Dein
8,604,124 B2 12/2013 Yamaguchi et al.
8,623,047 B2 1/2014 Cornet et al.
8,777,911 B2 7/2014 Heagle et al.
8,939,933 B2 1/2015 Santora et al.
10,155,071 B2 12/2018 Locke et al.
10,682,446 B2 6/2020 Askem et al.
2002/0161346 A1 10/2002 Lockwood et al.
2003/0199817 A1 10/2003 Thompson et al.
2007/0185426 A1 8/2007 Ambrosio et al.
2009/0005746 A1 1/2009 Nielsen et al.
2009/0198167 A1 8/2009 Ambrosio
2009/0275922 A1 11/2009 Coulthard et al.
2009/0281526 A1 11/2009 Kenny et al.
2010/0160877 A1 6/2010 Kagan et al.
2010/0249688 A1 9/2010 Ambrosio et al.
2010/0298792 A1 11/2010 Weston et al.
2010/0305490 A1 12/2010 Coulthard et al.
2011/0028917 A1 2/2011 Hall et al.
2011/0213319 A1 9/2011 Blott et al.
2012/0022436 A1 1/2012 Bradley et al.
2012/0071814 A1 3/2012 Fallin et al.
2012/0135225 A1 5/2012 Colas et al.
2012/0330253 A1 12/2012 Robinson et al.
2013/0090588 A1 4/2013 Buus et al.
2013/0110058 A1 5/2013 Adie et al.
2013/0296815 A1 11/2013 Boehringer et al.
2014/0276288 A1 9/2014 Randolph et al.
2014/0303261 A1 10/2014 Ramjit et al.
2014/0316328 A1 10/2014 Rajendran et al.
2015/0018785 A1 1/2015 Vess et al.
2015/0273181 A1 10/2015 Leeflang et al.
2015/0320911 A1 11/2015 Sun et al.
2016/0022500 A1 1/2016 Tumey
2016/0106892 A1 4/2016 Hartwell
2016/0325028 A1 11/2016 Locke et al.
2016/0346444 A1 12/2016 Zamierowski
2017/0065458 A1 3/2017 Mumby et al.
2017/0189239 A1 7/2017 Dunn
2017/0360544 A1 12/2017 Ward et al.
2018/0104391 A1 4/2018 Luxon et al.
2018/0214313 A1 8/2018 Pratt et al.
2018/0214315 A1 8/2018 Mercer et al.
2018/0353336 A1 12/2018 Locke et al.
2018/0353339 A1 12/2018 Locke et al.
2019/0008694 A1 1/2019 Piotrowski et al.
2019/0117466 A1 4/2019 Kazala et al.
2019/0117861 A1 4/2019 Locke et al.
2019/0201595 A1 7/2019 Jardret et al.
2019/0321232 A1 10/2019 Jardret et al.
2020/0060879 A1 2/2020 Edwards et al.
2020/0129338 A1 4/2020 Gardiner et al.
2020/0246604 A1 8/2020 Asefi et al.
2020/0253788 A1 8/2020 Rehbein et al.
2020/0337906 A1 10/2020 Long et al.
2020/0368072 A1 11/2020 McNulty et al.
2021/0077302 A1 3/2021 Carroll et al.
2021/0187171 A1 6/2021 Collinson et al.
2022/0249763 A1 8/2022 Asefi et al.
2024/0000616 A1 1/2024 Ward et al.
2024/0293264 A1 9/2024 Ward et al.
2024/0358910 A1 10/2024 Ward et al.
2024/0390190 A1 11/2024 Ward et al.

FOREIGN PATENT DOCUMENTS

JP 2013-517839 A 5/2013
JP 2014-511222 A 5/2014
JP 2015-198975 A 11/2015
JP 2015-532147 A 11/2015
JP 2017-517312 A 6/2017
JP 2017518793 A 7/2017
JP 2017-527336 A 9/2017
JP 2019-500964 A 1/2019
WO 1994027697 A1 12/1994
WO 2007/106589 A2 9/2007
WO 2009/003886 A1 1/2009
WO 2011/091045 A2 7/2011
WO 2012/106590 A2 8/2012
WO 2019/070133 A1 4/2019
WO WO-2019/070133 * 4/2019
WO 2019/113275 A1 6/2019
WO 2019/140444 A1 7/2019
WO 2019/226454 A1 11/2019
WO 2020/226511 A1 11/2020
WO 2021/070051 A2 4/2021

OTHER PUBLICATIONS

International Preliminary Report on Patentability, PCT/NZ2018/050134, dated Apr. 8, 2020, 6 pages.
International Preliminary Report on Patentability, PCT/NZ2021/050206, dated May 30, 2023, 6 pages.
International Preliminary Report on Patentability, PCT/NZ2021/050207, dated May 30, 2023, 9 pages.
International Preliminary Report on Patentability, PCT/NZ2021/050208, dated May 30, 2023, 10 pages.
International Preliminary Report on Patentability, PCT/NZ2022/050090, dated Dec. 14. 2023, 8 pages.
International Search Report and Written Opinion, PCT/NZ2018/050134, dated Jan. 10, 2019, 11 pages.
International Search Report and Written Opinion, PCT/NZ2020/050044, dated Aug. 3, 2020, 20 pages.
International Search Report and Written Opinion, PCT/NZ2021/050205, dated Mar. 25, 2022, 24 pages.
International Search Report and Written Opinion, PCT/NZ2021/050206, dated Feb. 22, 2022, 14 pages.
International Search Report and Written Opinion, PCT/NZ2021/050207, dated Feb. 22, 2022, 25 pages.
International Search Report and Written Opinion, PCT/NZ2021/050208, dated Mar. 1, 2022, 15 pages.
International Search Report and Written Opinion, PCT/NZ2022/050090, dated Oct. 12, 2022, 11 pages.
Extended European Search Report, European Application No. 21898777.4, dated Oct. 24, 2024, 7 pages.
U.S. Appl. No. 16/753,725, filed Apr. 3, 2020, Dorrin Asefi.
U.S. Appl. No. 18/038,356, filed May 23, 2023, Brian Roderick Ward.

(56) References Cited

OTHER PUBLICATIONS

U.S. Appl. No. 18/038,365, filed May 23, 2023, Brian Roderick Ward, US 20250000616.
U.S. Appl. No. 17/608,305, filed Nov. 2, 2021, Dorrin Asefi, US20220249763.
U.S. Appl. No. 18/038,353, filed May 23, 2023, Brian Roderick Ward.
U.S. Appl. No. 18/575,184, filed Dec. 28, 2023, Brian Roderick Ward.
Extended European Search Report, European Application No. 21898775.8, dated Sep. 17, 2024, 8 pages.

* cited by examiner 413
405
411
403

405
495
407
409
403

407
495
405
403
493
491
409
485
475
481
471

405
403

495
405
407
409
403

407
495
409
405
493
491
403
485
475
471
481

Bubbly Slug Churn Annular Wispy-Annular

FLUID DRAINAGE OR DELIVERY DEVICE FOR TREATMENT SITE

CROSS-REFERENCE TO RELATED APPLICATIONS

This application is a 35 U.S.C. § 371 national stage filing of International Application No. PCT/NZ2021/050206, filed Nov. 24, 2021, which claims priority to U.S. provisional application No. 63/117,995, filed Nov. 24, 2020, U.S. provisional application No. 63/217,889, filed Jul. 2, 2021, and U.S. provisional application No. 63/279,915, filed Nov. 16, 2021. The contents of the aforementioned applications are hereby incorporated by reference in their entirety.

TECHNICAL FIELD

The invention relates to a device for implanting at a treatment site for the drainage of fluid from the site or for the delivery of fluid to the site. In particular, the device is bioresorbable. The invention further relates to a system and method for draining fluid from a treatment site or delivering fluid to a treatment site using the device of the invention, and to a method of manufacturing said device.

BACKGROUND OF THE INVENTION

The drainage of fluid and the reduction of dead space from surgical or traumatic wounds is often a critical factor in the timely and effective recovery of a patient. Currently, there is no good solution for eliminating dead space at the time of surgery. Suturing provides linear closure rather than offering closure across the entire separated tissue plane. Surgical drains are only partially effective in removing fluid and do not deal with the primary issue of closing dead space immediately following surgery. Tissue adhesives have not proven to be reliably effective, and manually suturing across a total area only provides limited amount of localized closure.

Seroma or hematoma formation post-surgery or trauma can hinder recovery. Seromas and hematomas are pockets of serous fluid or blood that accumulate at wound sites. In the absence of adequate drainage, poor healing, infection or dehiscence may lead to a requirement for additional surgery and longer hospital stays. Seromas and hematomas are common after reconstructive plastic surgery procedures, trauma, mastectomy, tumour excision, caesarean, hernia repair and open surgical procedures involving extensive tissue elevation and separation.

While reducing dead space and providing drainage of fluid from a wound site is highly desirable in many instances, it is useful in other circumstances to be able to deliver fluid directly to a wound site to aid in the wound healing process. For example, instilling antimicrobial solutions locally to prevent infections. Similarly, instillation of local anaesthetics can aid pain management.

The applicant's earlier application PCT/NZ2018/050134 discloses a device for implanting at a treatment site for the drainage of fluid from the site or for the delivery of fluid to the site. The device comprises a bioresorbable resilient truss for holding two tissue surfaces spaced apart and defining a channel into which fluid from the treatment site can drain or from which fluid can be delivered to the treatment site. Many of the trusses described in that application are manufactured by heat bonding bioresorbable polymeric filament. The bioresorbable polymeric filaments utilised in these trusses are polymers having a microstructure that is highly oriented. The process of heat bonding the filaments changes the microstructure of the polymer at and adjacent to the bond site, typically lowering the degree of orientation, such that the material in these regions is in a lower energy state. These regions of filament with an altered microstructure have been found to be reabsorbed at a faster rate than the portions of filament with an unaltered microstructure, meaning the truss may fail at the bonded regions first, losing its structural integrity. Heat bonding can also cause the filament to shrink and distort.

Further, there is a need for an implant that is able to withstand greater compressive (transverse, crush-type) forces, to reduce the likelihood of the channel collapsing and becoming blocked or constricted, while maintaining longitudinal flexibility. These characteristics are particularly important when the implant is placed in a region that undergoes a relatively high level of stress and strain due to movement of the recipient.

The implantation of synthetic materials can contribute to elevated levels of inflammation that typically manifest within the body following implantation, most particular in sensitive and vascular areas such as the pelvic floor or abdominal wall. Many bioresorbable materials also degrade and resorb through a process of bulk hydrolysis where the polymer chains of the synthetic material absorb water to break down the chemical structure to the various monomers which release harmful acids that can trigger elevated inflammation and a foreign body response such as seen with synthetic meshes commonly used in hernia abdominal wall repair and pelvic organ prolapse repair. Therefore, there is a desire to minimise the amount of synthetic material used in an implant.

It is therefore an object of the invention to provide a fluid drainage or delivery device that addresses one or more of the abovementioned shortcomings, and/or at least to provide a useful alternative to existing devices.

In this specification where reference has been made to patent specifications, other external documents, or other sources of information, this is generally to provide a context for discussing features of the invention. Unless specifically stated otherwise, reference to such external documents or sources of information is not to be construed as an admission that such documents or such sources of information, in any jurisdiction, are prior art or form part of the common general knowledge in the art.

SUMMARY OF INVENTION

According to a first aspect, the invention described herein broadly consists in a bioresorbable device for implantation in the body of a patient for administering fluid and/or negative pressure to a treatment site, the device comprising a bioresorbable resilient truss for holding two tissue surfaces spaced apart. The truss comprises two flexible elongate wall members wound in a manner to define a channel, the two elongate wall members intersecting each other periodically at a plurality of cross-over nodes; and at least two flexible elongate bracing members, each bracing member being mechanically linked to the two elongate wall members at a plurality of the cross-over nodes.

In an embodiment, the bracing members extend generally longitudinally along a side of the channel.

In an embodiment, the bracing truss members are provided on opposite sides of the channel.

In an embodiment, the wall members are wound to form a porous wall such that fluid from the treatment site can drain from the channel and/or fluid can be delivered to the treatment site from the channel. The device may be generally tubular.

In an embodiment, each bracing member is mechanically linked to the two elongate wall members at the respective cross-over nodes by way of the respective bracing member looping around the wall members.

In an embodiment, each bracing member comprises a main filament that forms a full 360 degree loop around the wall members at the respective cross-over nodes. In some embodiments, each bracing member main filament may form a 720 degree loop around the wall members at the respective cross-over nodes In an embodiment, each bracing member further comprises a secondary filament that twists around the main filament.

In an embodiment, each bracing member comprises two filaments twisted together, with the wall members held between the two filaments at the respective cross-over nodes.

In an embodiment, there is at least one full twist of the filaments between adjacent interlinked cross-over nodes.

In an embodiment, each bracing member is mechanically linked to the two elongate wall members at the respective cross-over nodes by way of the wall members looping around the respective bracing members.

In an embodiment, each elongate wall member is generally helical. In an embodiment, a first one of the wall members is generally helical with a first pitch length, and a second one of the wall members is generally helical with a second pitch length that is the same as the first pitch length. The two helical wall members may be oppositely wound.

Alternatively, a first one of the wall members may be a left-side wall member, and a second one of the wall members may be a right-side wall member. Optionally the truss may comprise two left-side wall members, and two right-side wall members. The left and right wall members may snake between the bracing members in a non-helical form.

In an embodiment, each wall member has a pitch length that is between about 2 mm and about 10 mm. Each wall member may have a pitch length of about 4 mm.

In an embodiment, the wall members and bracing members comprise suture.

In an embodiment, the truss forms a flexible tube having a round or oval cross-section.

In an embodiment, the channel has a cross-sectional area of at least 16 $mm^2$.

In an embodiment, the device further comprising a flexible bioresorbable sheet, the sheet forming at least a portion of a wall of the channel.

In an embodiment, the flexible bioresorbable sheet is wrapped around the truss. The flexible bioresorbable sheet may comprise a plurality of apertures in the flexible bioresorbable sheet to permit fluid flow into the channel.

In an embodiment, the device further comprises two flexible bioresorbable sheets, wherein the channel is formed between facing surfaces of the two flexible sheets. A plurality of apertures may be formed in one or both flexible sheets along a wall of the channel to permit fluid flow into the channel.

In such embodiments, the or each flexible sheet comprises one or more layers of extracellular matrix (ECM) or polymeric material. The ECM may be formed from decellularised propria-submucosa of a ruminant forestomach.

In an embodiment, the device comprises a port in fluid communication with the one or more channels and being connectable to a source of negative pressure or positive pressure. Preferably the port is connectable to a source of negative pressure.

In an embodiment, the treatment site is a space between surfaces of muscle tissue, connective tissue or skin tissue that have been separated during surgery or as a result of trauma.

According to a second aspect, the invention described herein broadly consists in a system for draining fluid from a treatment site or delivering fluid to a treatment site in the body of a patient. The system comprising: (i) a device according to the first aspect of the invention; (ii) a conduit releasably coupled to either the port of the device or to a fluid impermeable dressing; (iii) a reservoir located external to the body of the patient, the reservoir in fluid communication with the conduit for receiving fluid from the conduit or delivering fluid to the conduit; and (iv) a source of pressure coupled to the conduit for delivering positive pressure or negative pressure to the device.

In an embodiment, the source of pressure is capable of delivering negative pressure to the device so that fluid is drained from the treatment site into the device and transferred through the conduit to the reservoir. Alternatively, the source of pressure is capable of delivering positive pressure to the device so that fluid in the reservoir is transferred through the conduit into the device and to the treatment site.

According to a third aspect, the invention described herein broadly consists in a method of draining fluid from a treatment site or delivering fluid to a treatment site in the body of a patient. The method comprising: (i) implanting a device according to the first aspect of the invention at the treatment site; (ii) coupling a conduit to the device, the conduit being connected to a reservoir located external to the body of the patient for receiving fluid from the conduit or delivering fluid to the conduit; and (iii) delivering negative pressure to the device so that fluid is drained from the treatment site into the device and transferred through the conduit to the reservoir, or delivering positive pressure to the device so that fluid in the reservoir is transferred through the conduit into the device and to the treatment site.

In a fourth aspect, the present invention provides a system for treating a wound comprising: a fluid input and a fluid output for connection to a wound treatment device located at the wound. The wound treatment device may be as described above. The fluid input is adapted to be fluidly connected to an upstream side of the wound treatment device and the fluid output is adapted to be fluidly connected to a downstream side of the wound treatment device. The system further comprises an air inlet valve upstream of the fluid output; an actuator to drive the air inlet valve between an open position and a closed position; a pump downstream of the fluid input; a motor to drive the pump to provide a negative pressure to the wound treatment device; and a controller in communication with the actuator and the motor to operate the air inlet valve and the pump. The controller is configured to: i) open the air inlet valve and operate the pump to maintain a first vacuum pressure at the wound treatment device and introduce air into the wound treatment device; ii) close the air inlet valve and operate the pump to maintain a second vacuum pressure at the wound treatment device and remove air and fluid from the wound treatment device. The first vacuum pressure is less than or equal to the second vacuum pressure.

In an embodiment, the controller is configured to operate the pump to continuously maintain a negative pressure environment at the wound treatment device when the air valve is open and closed.

In an embodiment, the first and second vacuum pressures provide for effective negative pressure wound therapy.

In an embodiment, the controller is configured to repeat steps i) and ii) to cycle the air inlet valve between the open and closed positions.

In an embodiment, the controller is configured to repeat steps i) and ii) to continuously cycle the air inlet valve between the open and closed positions.

In an embodiment, the controller is configured to operate the pump when the air inlet valve is open to maintain a substantially constant first vacuum pressure.

In an embodiment, the controller is configured to operate the pump with the air inlet valve open so that a flow rate of air into the system through the air inlet valve is equal to a flow rate of the pump.

In an embodiment, the controller is configured to operate the pump when the air inlet valve is closed to maintain a substantially constant second vacuum pressure.

In an embodiment, the controller is configured to: in step (i), operate the pump with the air inlet valve open so that the system is in an equilibrium state with a zero or constant pressure differential across the treatment device.

In an embodiment, controller is configured to: in step (ii), operate the pump with the air inlet valve closed so that the system is in an equilibrium state with a zero or constant pressure differential across the treatment device.

In an embodiment, the controller is configured to operate the air inlet valve between open and closed to introduce a flow rate of air into the system that generates a bubble flow or slug flow comprising bubbles or slugs of air entrained in fluid flow from the wound treatment device.

In an embodiment, the controller is configured to operate the air inlet valve between open and closed to reduce a density of fluid at the wound to lift the fluid from the wound against gravity.

In an embodiment, the controller is configured to open and close the air inlet valve periodically.

In an embodiment, in step i) the controller is configured to open the air inlet valve for a predetermined time period. In an embodiment, in step i) the controller is configured to open the air inlet valve for at least 10 seconds.

In an embodiment, in step ii) the controller is configured to close the air inlet valve for a predetermined time period.

In an embodiment, the air inlet valve is open for at least 10% of the cycle pitch, or at least 20% of the cycle pitch, or at least 30% of the cycle pitch, or at least 40% of the cycle pitch, or at least 50% of the cycle pitch.

In an embodiment, in step i), the air inlet valve is open for a sufficient time period so that a volume of air delivered through the system is at least a substantial portion of a total volume of the system. For example in step (i), the air inlet valve may be open for a sufficient time period so that the volume of air delivered to the system is at least 50%, or at least 100% of the total volume of the system.

In an embodiment, the first vacuum pressure is about 30% to 100% of the second vacuum pressure.

In an embodiment, the first vacuum pressure is about 50 to 100 mmHg, preferably between about 80 and about 90 mmHg.

In an embodiment, the second vacuum pressure is about 100 to 150 mmHg, preferably between about 100 and about 110 mmHg.

In an embodiment, the first vacuum pressure is about 10 to 50 mmHg less than the second pressure.

In an embodiment, in step (i) the controller is configured to operate the pump to achieve a vacuum pressure threshold.

In an embodiment, in step (ii) the controller is configured to operate the pump to achieve a vacuum pressure threshold.

In an embodiment, the system comprises a downstream pressure sensor located downstream of the wound treatment device and in communication with the controller. The controller may be configured to, in step i) operate the pump to achieve the vacuum pressure threshold based on a pressure sensed by the downstream pressure sensor.

In an embodiment, the system comprises an upstream pressure sensor located upstream of the wound treatment device and in communication with the controller. The controller may be configured to, in step ii), operate the pump to achieve the vacuum pressure threshold based on a pressure sensed by the upstream pressure sensor.

In an embodiment, the system comprises:

an upstream pressure sensor located upstream of the wound treatment device and in communication with the controller, a downstream pressure sensor located downstream of the wound treatment device and in communication with the controller, and the controller is configured to, in step i) operate the pump to achieve a first vacuum pressure threshold based on a pressure sensed by the downstream pressure sensor; and in step ii), operate the pump to achieve a second vacuum pressure threshold based on a pressure sensed by the upstream pressure sensor.

In an embodiment, the first vacuum pressure threshold is less than or equal to the second vacuum pressure threshold.

In an embodiment, the system comprises an inlet restriction, and the upstream pressure sensor is located upstream of the inlet restriction so that the upstream pressure sensor measures ambient pressure when the air inlet valve is open.

In an embodiment, the system comprises an inlet restriction to present a predetermined pressure drop between ambient pressure and a vacuum pressure at the wound treatment device.

In an embodiment, the system comprises a filter to filter air introduced to the system, and wherein the filter is or comprises the inlet restriction.

In an embodiment, the pressure drop is approximately 20 to 130 mmHg.

In an embodiment, when the air inlet valve is open, substantially all pressure differential between ambient pressure and a pressure downstream of the wound treatment device is at the inlet restriction.

In an embodiment, the system comprises a reservoir for collecting fluid removed from the wound, and wherein the reservoir is located downstream of the pump such that fluid removed from the wound passes through the pump to the reservoir.

In an embodiment, the reservoir comprises a flexible bag.

In an embodiment, the reservoir comprises a vent to vent the reservoir to the ambient atmosphere.

In an embodiment, the system comprises a treatment fluid inlet upstream of the fluid outlet to connect a supply of treatment fluid.

In an embodiment, the system is configured so that, in step i) the introduction of treatment fluid to the wound treatment device is prevented or reduced by the introduction of air to the wound treatment device by the first vacuum pressure, and in step ii), treatment fluid is drawn to the wound treatment device by the second vacuum pressure.

In an embodiment, the system comprises:

a treatment fluid valve between the treatment fluid inlet and the fluid outlet, and an actuator to drive the treatment fluid inlet valve between an open position and a closed position, wherein the controller is in communication with the fluid inlet valve actuator and the controller is configured to, in a fluid supply state:

iii). open the fluid inlet valve and operate the pump to maintain a vacuum pressure at the wound treatment device and introduce treatment fluid into the wound treatment device;

iv). close the fluid inlet valve and operate the pump to maintain a vacuum pressure at the wound treatment device and remove fluid from the wound treatment device.

In an embodiment, the controller is configured to operate the pump to continuously maintain a negative pressure environment at the wound treatment device when the fluid inlet valve is open and closed.

In an embodiment, the controller is configured to, in step (iii), operate the pump to generate a third vacuum pressure at the wound treatment device, and, in step (iv), operate the pump to generate a fourth vacuum pressure at the wound treatment device, wherein the third vacuum pressure is less than or equal to the fourth vacuum pressure.

In an embodiment, the third vacuum pressure is equal or similar to the first vacuum pressure and the fourth vacuum pressure is equal or similar to the second vacuum pressure.

In an embodiment, the third and fourth vacuum pressures provide for effective negative pressure wound therapy.

In an embodiment, after closing the fluid inlet valve and operating the pump to generate the vacuum pressure at the wound, the controller is configured to:

(v) flush the treatment fluid from the wound by:

(v)(a) opening the air inlet valve and operating the pump to maintain a vacuum pressure (e.g. the first vacuum pressure) at the wound treatment device and introduce air into the wound treatment device, and (v)(b) closing the air inlet valve and operating the pump to maintain a vacuum pressure (e.g. the second vacuum pressure) at the wound treatment device and remove fluid from the wound treatment device.

In an embodiment, in step (v) the controller is configured to repeat steps (v)(a) and (v)(b) a predetermined number of times (for example, three times) to remove treatment fluid from the wound.

In an embodiment, in the fluid treatment state, the controller is configured to repeat steps (iii) to (v) a predetermined number of times.

In an embodiment, the controller is configured to, in step (iv), close the fluid inlet valve, wait for a predetermined time period, and operate the pump to generate the vacuum pressure at the wound treatment device and remove fluid from the wound treatment device.

In an embodiment, the controller is configured to activate the fluid supply state periodically.

In an embodiment, a time period between activating the fluid supply state is much greater than a cycle time of the air inlet valve.

In an embodiment, the system comprises an upstream pressure sensor and/or a downstream pressure sensor in communication with the controller, and, in step (iii), the controller is configured to operate the pump to achieve a vacuum pressure threshold based on a pressure sensed by the upstream and/or downstream pressure sensor.

In an embodiment, the system comprises an upstream pressure sensor and/or a downstream pressure sensor in communication with the controller, and, in step (iv), the controller is configured to operate the pump to achieve a vacuum pressure threshold based on a pressure sensed by the upstream and/or downstream pressure sensor.

This invention may also be said broadly to consist in the parts, elements and features referred to or indicated in the specification of the application, individually or collectively, and any or all combinations of any two or more said parts, elements or features. Where specific integers are mentioned herein which have known equivalents in the art to which this invention relates, such known equivalents are deemed to be incorporated herein as if individually described.

The term ‘comprising’ as used in this specification and claims means ‘consisting at least in part of’. When interpreting statements in this specification and claims that include the term ‘comprising’, other features besides those prefaced by this term can also be present. Related terms such as ‘comprise’ and ‘comprised’ are to be interpreted in a similar manner.

It is intended that reference to a range of numbers disclosed herein (for example, 1 to 10) also incorporates reference to all rational numbers within that range and any range of rational numbers within that range (for example, 1 to 6, 1.5 to 5.5 and 3.1 to 10).

Therefore, all sub-ranges of all ranges expressly disclosed herein are hereby expressly disclosed.

As used herein the term ‘(s)’ following a noun means the plural and/or singular form of that noun. As used herein the term ‘and/or’ means ‘and’ or ‘or’, or where the context allows, both.

BRIEF DESCRIPTION OF THE FIGURES

The present invention will now be described by way of example only and with reference to the accompanying drawings in which:

FIG. 44A is a perspective view of the set-up of the apparatus, and FIG. 44B is a section view through the mandrel for the truss illustrating the first step of winding filaments around the mandrel and bracing members;

FIG. 45A is a perspective view of the set-up of the apparatus, and FIG. 45B is a section view through the mandrel for the truss illustrating the second step of winding filaments around the mandrel;

FIG. 46A is a perspective view of the set-up of the apparatus, and FIG. 46B is a section view through the mandrel for the truss illustrating the third step of winding filaments around the mandrel;

FIG. 47A is a perspective view of the set-up of the apparatus, FIG. 47B is a perspective view of a portion of the wound truss wall members, and FIG. 47C is a section view through the mandrel for the truss illustrating the fourth step of winding filaments around the mandrel;

FIG. 48A is a perspective view of the set-up of the apparatus, FIG. 48B is a perspective view of a portion of the wound truss wall members, and FIG. 48C is a section view through the mandrel for the truss illustrating the fifth step of winding filaments around the mandrel;

DETAILED DESCRIPTION

Definitions

The term "bioresorbable" as used herein means able to be broken down and absorbed or remodelled by the body, and therefore does not need to be removed manually.

The term "treatment site" as used herein refers to a site in a human or animal body where surfaces of muscle tissue, connective tissue or skin tissue have been separated during surgery or as a result of trauma or removal.

The term "propria-submucosa" as used herein refers to the tissue structure formed by the blending of the lamina propria and submucosa in the forestomach of a ruminant.

The term "lamina propria" as used herein refers to the luminal portion of the propria-submucosa, which includes a dense layer of extracellular matrix.

The term "extracellular matrix" (ECM) as used herein refers to animal or human tissue that has been decellularised and provides a matrix for structural integrity and a framework for carrying other materials.

The term "decellularised" as used herein refers to the removal of cells and their related debris from a portion of a tissue or organ, for example, from ECM.

The term "helical" as used herein refers to a generally spiralling form, it may relate to a form with a circular cross-section, but also refers to forms with non-circular cross sections.

The term "polymeric material" as used herein refers to large molecules or macromolecules comprising many repeated subunits, and may be natural materials including, but not limited to, polypeptides and proteins (e.g. collagen), polysaccharides (e.g. alginate) and other biopolymers such as glycoproteins, or may be synthetic materials including, but not limited to polyglycolic acid, polylactic acid, P4HB (Poly-4-hydroxybutyrate), polylactic and polyglycolic acid copolymers, polycaprolactone and polydioxanone.

Device

Figure 58:
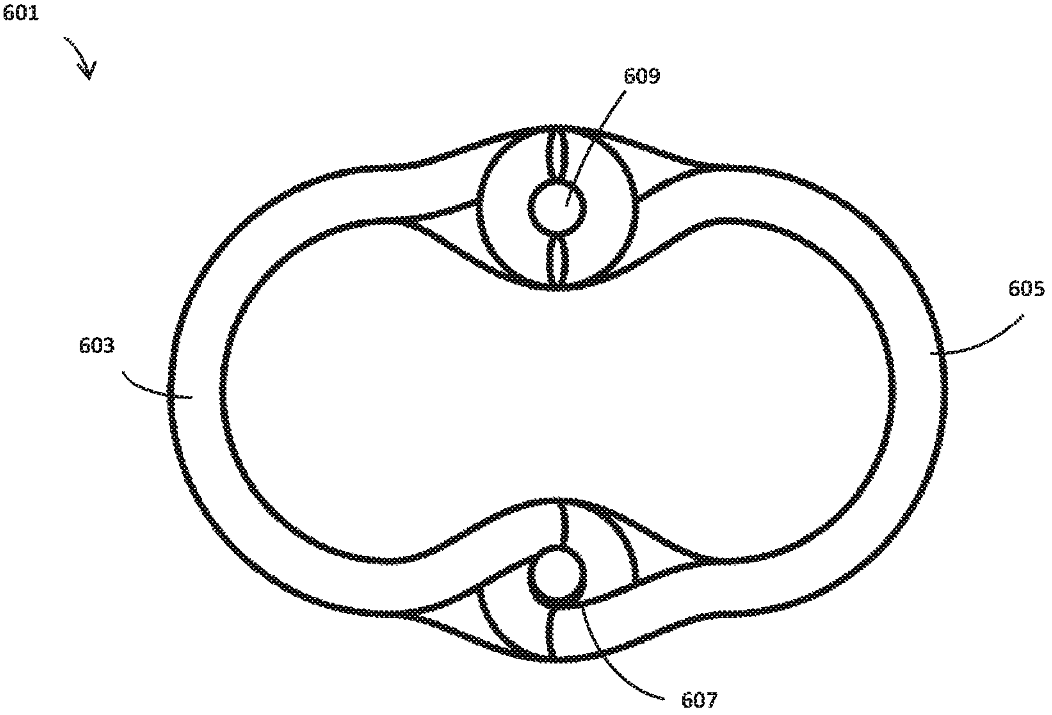
FIG. 58 is an end view of transverse section view of the truss structure of FIGS. 54 to 57.

Various embodiments of the device and system of the present invention will now be described with reference to FIGS. 1 to 58. In these figures, unless otherwise described, like reference numbers are used to indicate like features. Where various embodiments are illustrated, like reference numbers may be used for like or similar features in subsequent embodiments but with the addition of a multiple of 100, for example 2, 102, 202, 302 etc.

Directional terminology used in the following description is for ease of description and reference only, it is not intended to be limiting. For example, the terms 'front', 'rear', 'upper', 'lower', and other related terms are generally used with reference to the way the device is illustrated in the drawings.

FIGS. 1 to 26, 31 to 35 and 49 to 53 show various embodiments of a flexible truss for a bioresorbable device for implantation at a treatment site 62 in the body of a patient to drain fluid from the treatment site or deliver fluid to the treatment site. The truss 1, 101, 201, 301, 401, 501 is a resilient three-dimensional structure that defines an elongate channel into which fluid from the treatment site can drain or from which fluid can be delivered to the treatment site. The truss is flexible in its longitudinal direction LD to allow the channel(s) to flex to substantially conform to the contours of the treatment site 62 while having sufficient strength to hold two tissue surfaces apart, at least at the time of implantation, without the truss buckling or the channel collapsing or kinking under movement or application of clinically appropriate levels of negative pressure.

The truss 1, 101, 201, 301, 401, 501 is tubular in nature, with a non-circular or circular cross section. The truss is configured to, in use, provide support to the surrounding tissue surfaces in all generally radial directions. The truss comprises two or more flexible elongate wall members, which are wound in a manner to form a framework for, and thereby define, a channel into which fluid from the treatment site can drain or from which fluid can be delivered to the treatment site. The wall truss members are curved so as to follow a curved contour of the internal surface of the channel wall, at the periphery of the channel. In many embodiments, the truss wall members have a generally helical form.

The elongate wall members are wound such that they intersect each other periodically at a plurality of cross-over nodes. In preferred embodiments first and second truss wall members are generally helical but oppositely wound with a first of the wall members having a left-hand wind and the second wall member having a right-hand wind, such that they overlap each other periodically. The pitch of the first and second wall members may be the same or different. In alternative embodiments, the wall members may comprise first and second generally helical members wound in the same direction but with different pitches, or wall members of an alternative repetitive shape, such that results in the first and second wall members having periodic cross-over nodes.

In further alternative embodiments, the first and second wall members may be wound in a non-helical manner such that the first and second wall members generally remain on opposite sides of the device, engaging with each other at the cross-over nodes.

The truss wall and bracing members may be formed from any suitable bioresorbable filaments that have a degree of flexibility to allow the device to conform to the contours of the treatment site, and with sufficient structural strength and integrity to hold the two surfaces apart and thereby allow channels to form. The structural integrity of this material and resulting shape will also provide a means for the fluid flow channel to be reinstated should the device be kinked or crushed in any circumstance. For example, the truss members may comprise a length of suture, thread, cord, or tape made from a bioresorbable material such as polyglycolic acid (PGA), polylactic acid (PLA), polyglycolic-polylactic copolymers, P4HB (Poly-4-hydroxybutyrate), polycaprolactone or polydioxanone, or any blends of these materials.

For most applications, a channel with a cross-sectional area of at least 16 $mm^2$ is desirable. In such embodiments, the wall members may have a pitch length that is between about 2 mm and about 10 mm.

The truss further comprises at least two flexible elongate bracing members, each bracing member is mechanically linked to the two elongate wall members at a plurality of the wall member cross-over nodes forming periodic interlocked points along the truss. In preferred embodiments, each bracing member extends generally longitudinally along a side of the channel, along the channel wall. These bracing members act to hold the periodic cross-over nodes of the wall members in spaced apart relation, to reduce or prevent collapse of the channel walls due to relative movement of these points, and preventing crushing and kinking.

The mechanical link between the wall members and the respective bracing members is one that prevents or minimises relative movement between the wall members and prevents or minimises movement of the respective bracing member relative to the cross-over nodes. That is, the cross-over nodes of the intersecting wall members cannot slide along the length of the respective bracing member. The mechanical link may be formed by way of the respective bracing members looping around the wall members at the respective cross-over nodes, or by way of the wall members looping around the respective bracing member at the respective cross-over nodes. This mechanical interlocking of the bracing members and wall members ensures the microstructure of the truss at the join point is unaltered, and therefore the truss at that node will not generally be resorbed faster or slower than the rest of the truss structure.

The bracing truss members are typically provided as a pair of bracing members, positioned on opposite sides of the channel. However, alternative embodiments may include additional bracing members, for example three bracing members, generally spaced evenly about the periphery of the truss tube.

The truss has a porous structure which permits free fluid exchange from the internal channel to the surrounding area for more effective passage of fluid while using less material than existing solutions. This is advantageous because synthetic bioresorbable polymers typically release acid when they breakdown which can cause elevated levels of inflammation.

Various embodiments are described below with reference to the drawings.

Embodiment 1

FIGS. 1 to 5 show a truss 1 according to a first embodiment. The truss 1 comprises a first wall member 3 having a generally helical form with a left-hand wind, and an oppositely wound second wall member 5 having a generally helical form with a right-hand wind. The pitch length P1 of the first wall member 3 is the same as the pitch length of the second wall member 5.

The truss 1 forms a tube and channel that is oval or elliptical in cross section (FIG. 4), with a major dimension M1, and a minor dimension N1 that is less than the major dimension. A dimension N1 that is less than M1 may increase the ability of the truss to withstand side loading compared with a truss having a circular cross section. The oval or elliptical cross section may also improve the ease of manipulation of the truss, allowing the linear device to be more readily shaped into a looped or 'S' shaped device when fabricated and helps ensures the truss is correctly orientated when it is implanted, with the N1 axis holding the opposing tissue surfaces apart.

Two elongate bracing members 7, 9 are provided, extending along sides of the truss, in line with the minor axis N1. Referring to the orientation shown, a first bracing member 7 is positioned at a bottom side of the truss 1 and a second bracing member 9 at the top side of the truss. These side bracing members 7, 9 have a length that is substantially the same as the length of the channel or the portion of the channel along which they extend. That is, they are generally straight members that extend the length of the truss.

At each cross-over node 11, 13, where the first and second wall members 3, 5 intersect, the first and second members are twisted together and extend tightly around the respective bracing member 7 or 9. In the embodiment shown, the first and second members 3, 5, form two full twists with each other and about the respective bracing member 7 or 9, and are interlocked with the bracing member 7, 9 along a distance Y1.

In one example embodiment having this design, for a tube having a cross sectional area of about 50 $mm^2$ the wall members 3, 5 have a half-pitch length x1 of about 2 mm, and the length of the interlocked portion y1 is about 2.75 mm, formed from two full loops of the wall members 3, 5.

Figure 1:
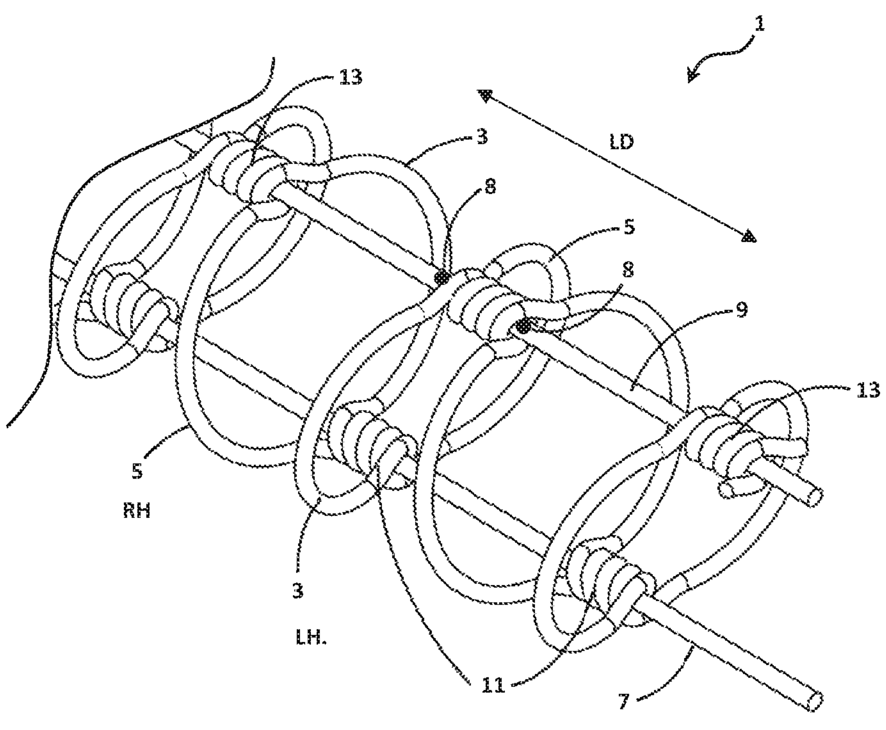
FIG. 1 is a right side perspective view showing a first embodiment truss structure having an indeterminate length.
Figure 2:
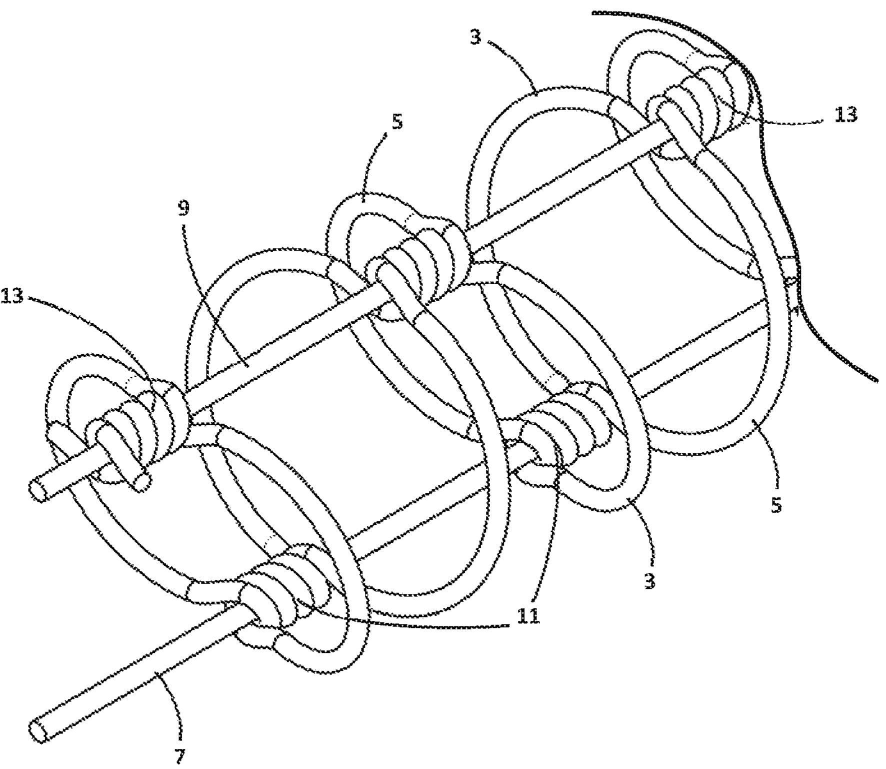
FIG. 2 is a left side perspective view showing truss structure of FIG. 1, the truss having an indeterminate length.
Figure 3:
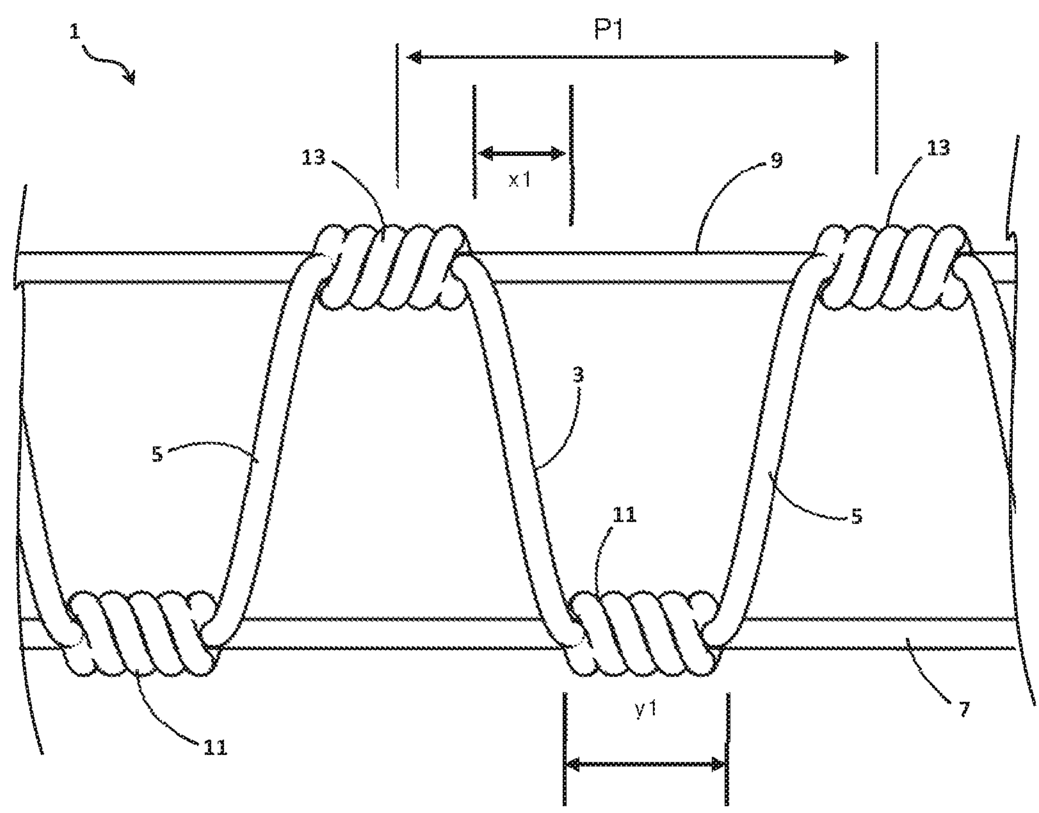
FIG. 3 is a side elevation view corresponding to FIGS. 1 and 2.
Figure 4:
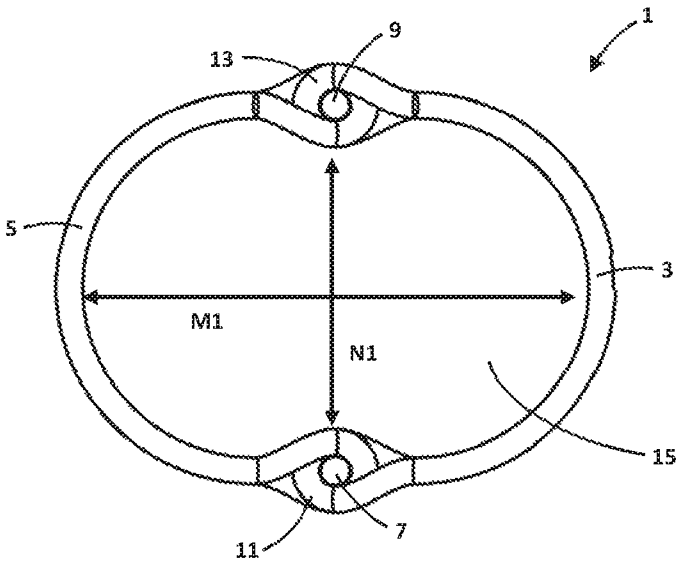
FIG. 4 is an end elevation view (or a transverse section view) of the embodiment of FIGS. 1 to 3.
Figure 5:
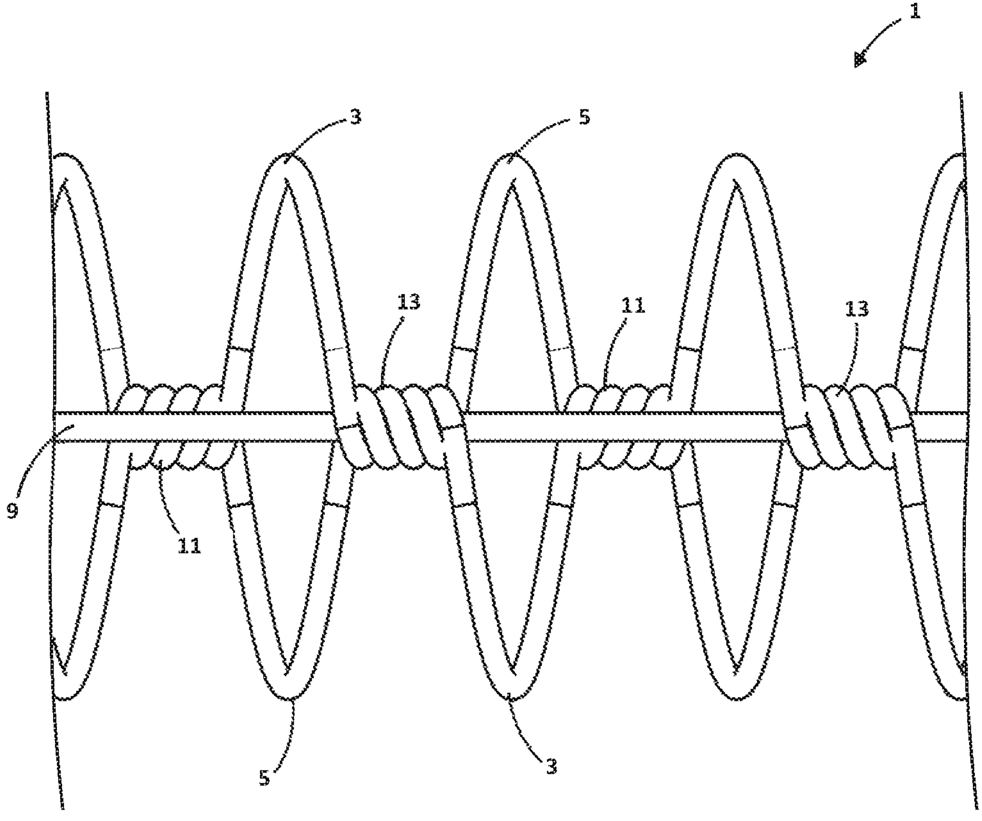
FIG. 5 is a plan view of the embodiment of FIGS. 1 to 4.
Figure 6:
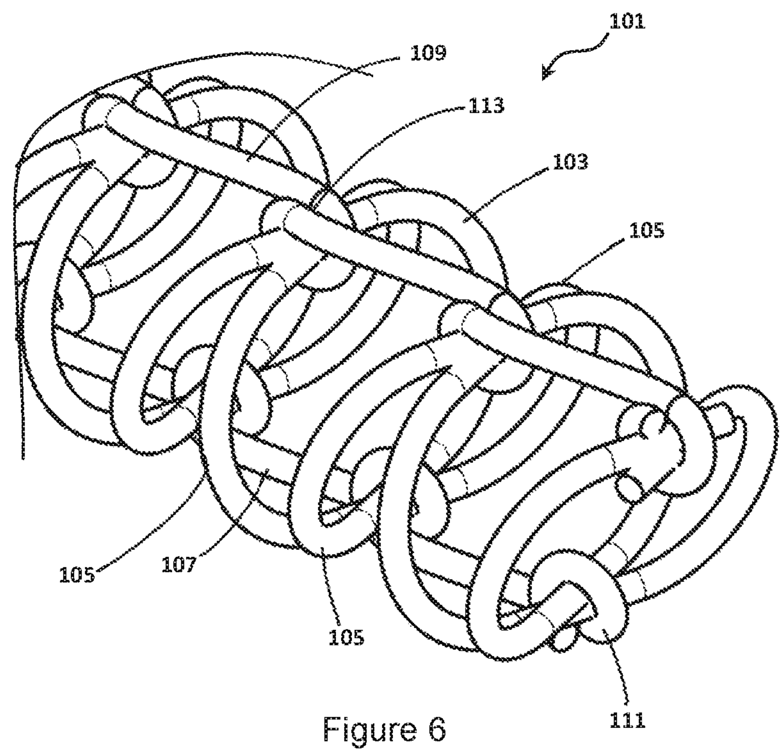
FIG. 6 is a right side perspective view showing a second embodiment truss structure having an indeterminate length.
Figure 7:
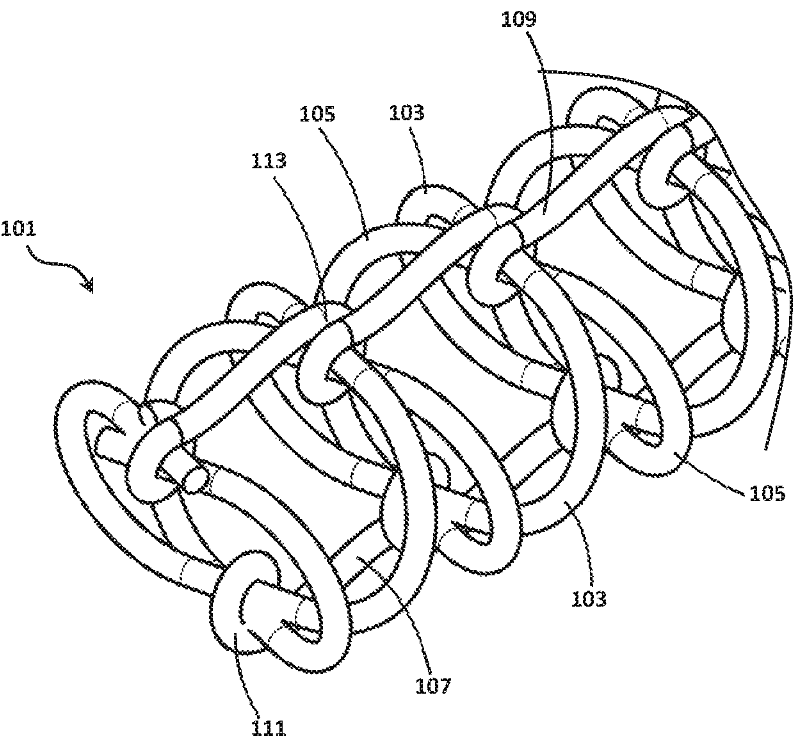
FIG. 7 is a left side perspective view showing truss structure of FIG. 6, the truss having an indeterminate length.
Figure 8:
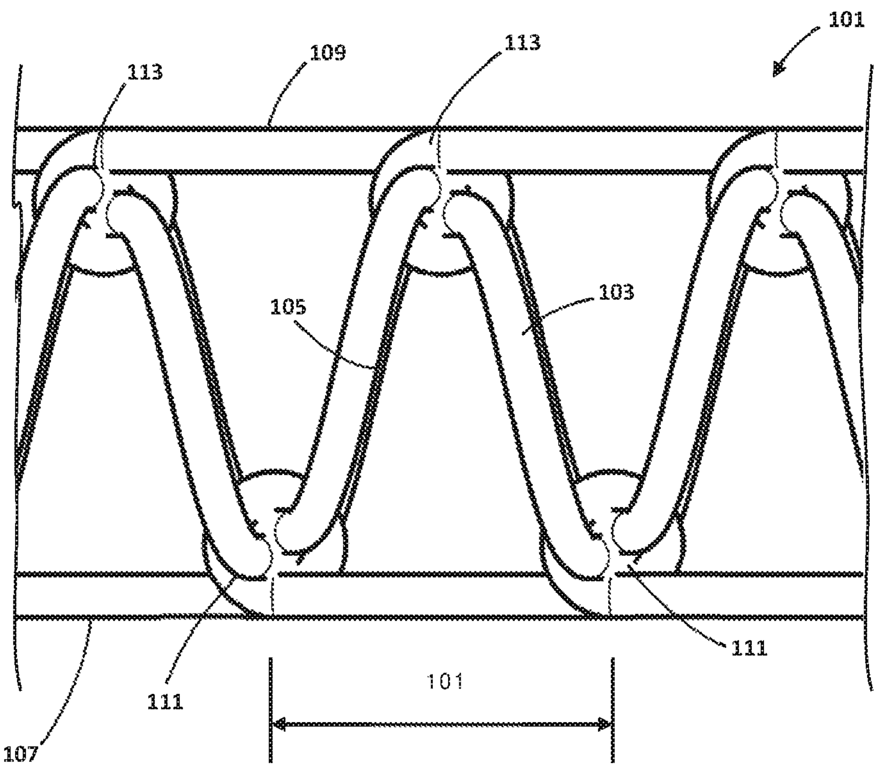
FIG. 8 is a side elevation view corresponding to FIGS. 6 and 7.
Figure 9:
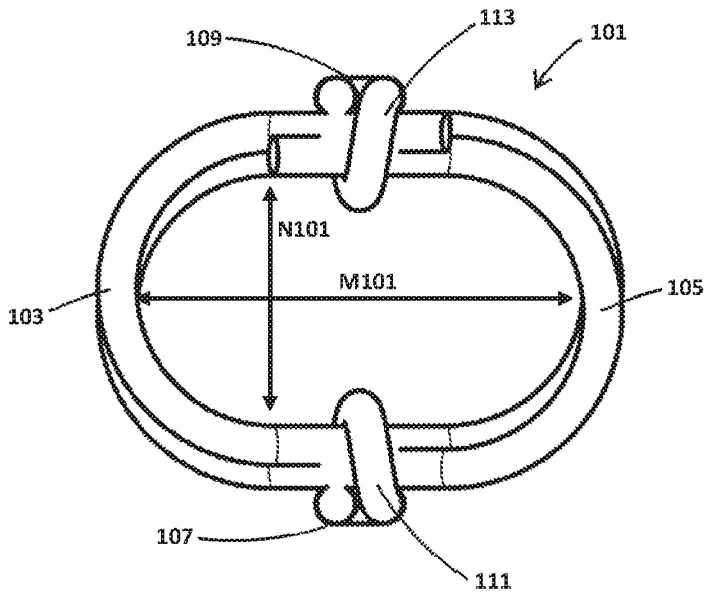
FIG. 9 is an end elevation view (or a transverse section view) of the embodiment of FIGS. 6 to 8.

To reduce the likelihood of the cross-over nodes 11, 13 sliding along the respective bracing member 7 or 9, knots may be provided in the bracing members on either side of each node 11, 13, for example at the points 8 indicated in FIG. 1. These knots would act obstruct movement of the twisted portion of the wall members at the nodes along the bracing members and thereby reduce the likelihood of collapse of the truss 1.

As described in more detail with respect to the embodiments below, the process of manufacturing the truss involves wrapping filaments around a mandrel. Before removing the truss from the mandrel, the truss is heat treated to set the truss shape. The final truss shape is determined by the mandrel shape and set by the heat treatment step.

Embodiment 101

FIGS. 6 to 10 show a truss 101 according to a second embodiment. The truss 101 comprises a first wall member 103 having a generally helical form with a right-hand wind, and an oppositely wound second wall member 105 having a generally helical form with a left-hand wind. The pitch length P101 of the first wall member 103 is the same as the pitch length of the second wall member 105. The truss 101 forms a tube and channel that is oval in cross section (FIG. 9), with a major dimension M101, and a minor dimension N101 that is less than the major dimension.

In one example, a truss 101 according to this embodiment has a cross-sectional channel of about 16 $mm^2$ with a with a major dimension M101 of about 6.4 mm, a minor dimension N101 of about 3.2 mm, and a pitch length P101 of about 4 mm.

Two elongate bracing members 107, 109 extend longitudinally along the wall of the truss 101, in line with the minor axis N101 on an outer side of the wall members 103, 105. Referring to the orientation shown, a first bracing member 107 is positioned at a bottom of the truss 101 and a second bracing member 109 at the top side of the truss 101. These side bracing members 107, 109 have an unwound length that is longer the length of the channel or the portion of the channel along which they extend. The bracing members 107, 109 are positioned to lie on the external side of the wall members, but in alternative embodiments may be positioned to extend along the internal side of the wall members 103, 105.

At each cross-over node 111, 113, where the first and second wall members 103, 105 intersect, a respective one of the bracing members 107, 109 loops tightly around the intersecting first and second wall members 103, 105, forming a full 360 degree loop at that node 111, 113. The loop formed generally sits in the vertical longitudinal plane of the truss which is coincident with the minor axis.

Figure 10:
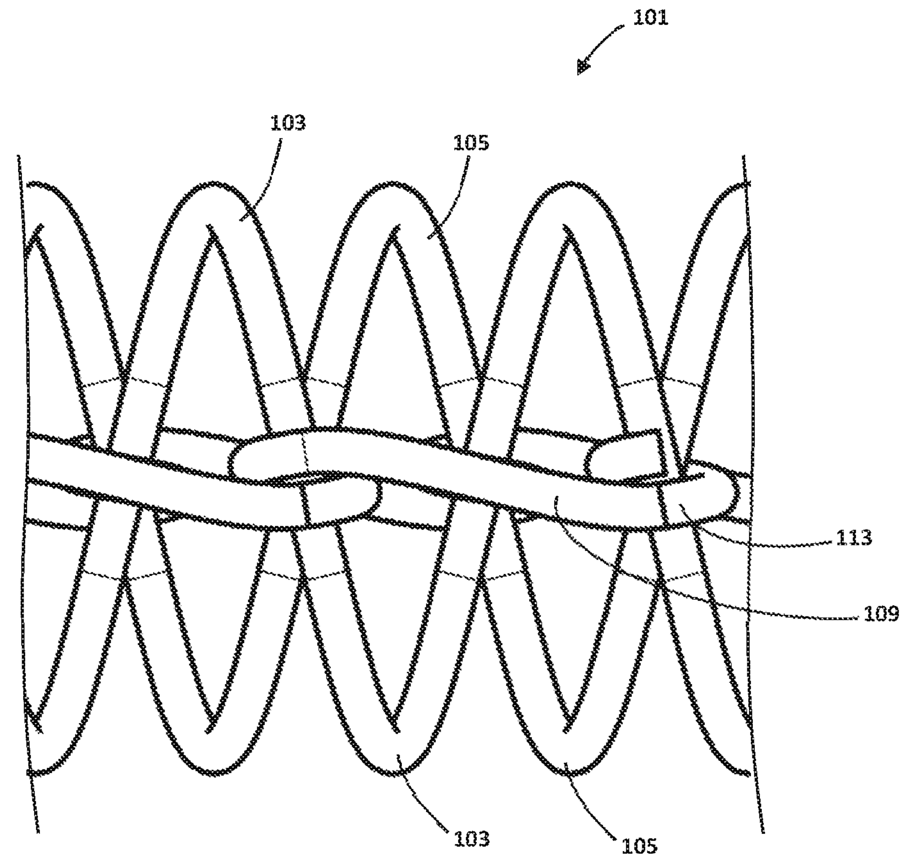
FIG. 10 is a plan view of the embodiment of FIGS. 6 to 9.
Figure 11:
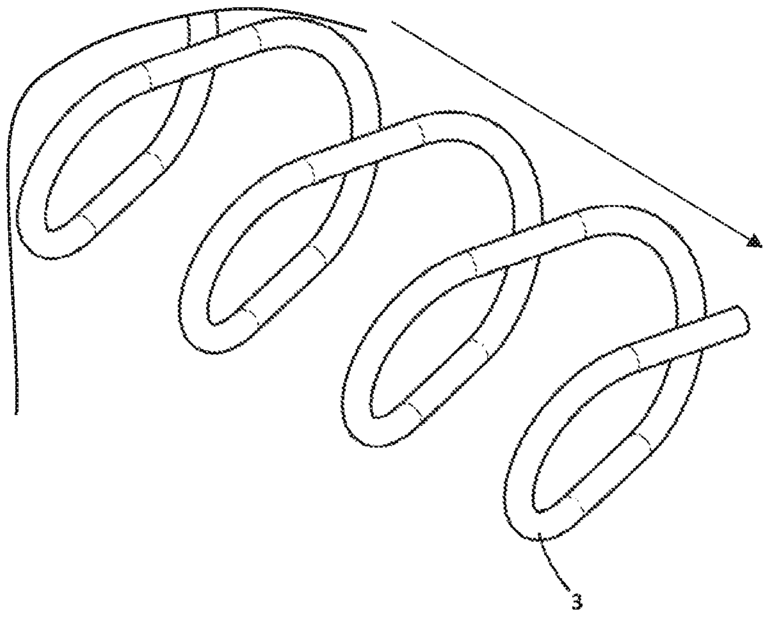
FIG. 11 is a perspective view illustrating a step for manufacturing the first wall member in the truss of FIGS. 6 to 10.
Figure 12:
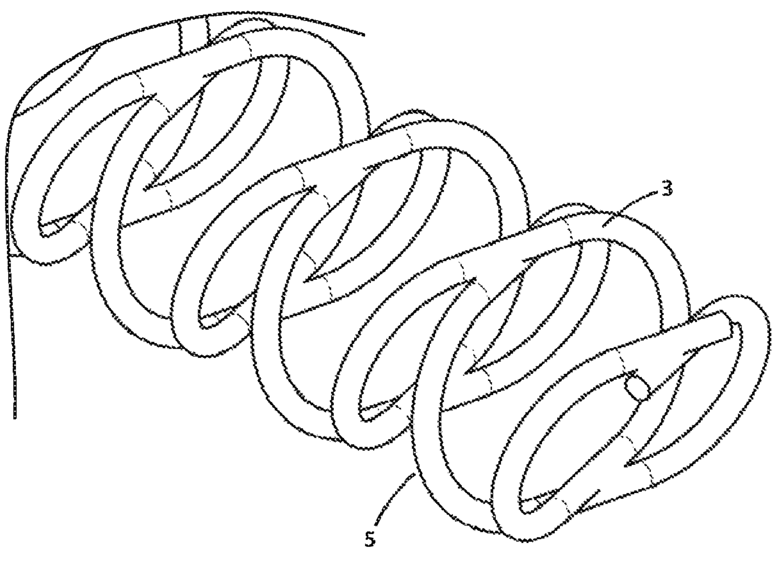
FIG. 12 is a perspective view illustrating a step for manufacturing the second wall member in the truss embodiment of FIGS. 6 to 10.

In the embodiment shown, each bracing member 107, 109 enters each locking loop from the same side (e.g. left side as illustrated), and exits each loop on the other side (e.g. the right side as illustrated) such that between adjacent cross-over join nodes 111 or 113, the bracing member 107, 109 is at a slight angle to the longitudinal axis of the truss as is best illustrated in FIG. 10. Alternatively, each bracing member 107, 109 may enter each locking loop from one side (e.g. left side) and exit the loop on the other side (e.g. the right side), then reverse the direction for alternating loops such that between adjacent cross-over join nodes 111 or 113, the bracing member 107, 109 is substantially parallel to the longitudinal axis of the truss.

FIGS. 11 to 16 illustrate a method for manufacturing the truss 101 shown in FIGS. 6 to 10. In a first step (FIG. 11), the helical first wall member 103 is formed by winding a filament of suture or other bioresorbable polymeric filament around a mandrel. For this embodiment with its non-circular shape, the mandrel may comprise two cylindrical rods placed side-by-side. In one embodiment, the mandrel rods are about 3.2 mm. The filament is secured at one end, for example by clamping, then wound about the mandrel by rotating a filament dispenser around the mandrel while moving in a linear direction, winding the filament in a helical manner at a first pitch length P101. When the desired length for the truss is reached, the filament is secured on the mandrel at a second end, for example by way of a locking wind.

To form the second helical wall member 105, the rotational direction and linear movement speed of the filament dispenser is unchanged, but the linear direction is reversed to return the dispenser to the first end while winding the second helical wall member as a left-hand wind with the same pitch length as the first wall member. The wall member filament is then secured at the first end and may be cut. The mandrel remains unheated through this process such that no heat bonding occurs between the first and second wall members.

Figure 13:
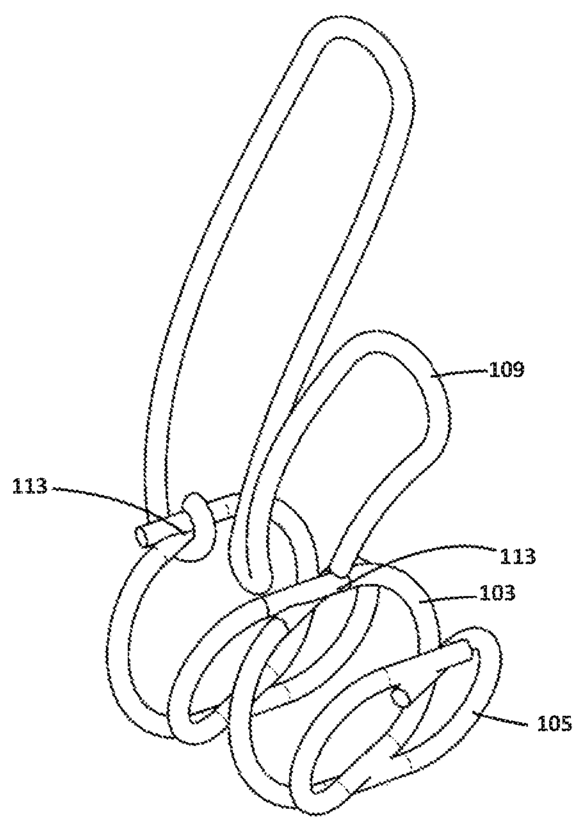
FIG. 13 is a perspective view illustrating a first step for forming a first one of the bracing members in the truss of FIGS. 6 to 10.
Figure 14:
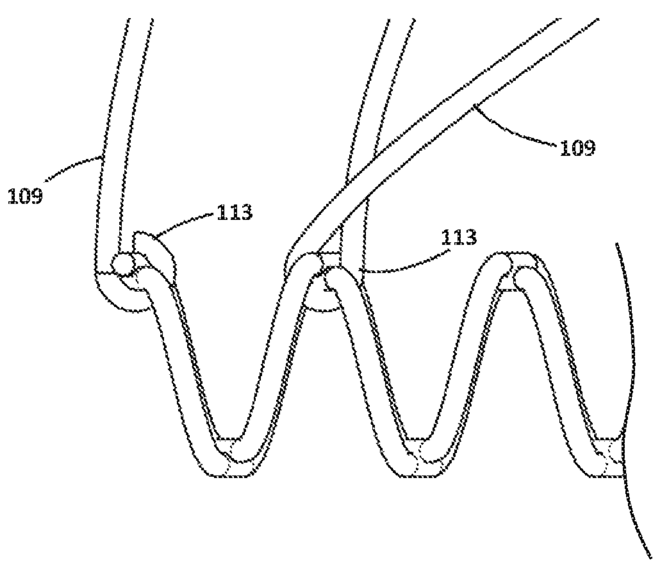
FIG. 14 is a side view illustrating a second step for forming a first one of the bracing members in the truss of FIGS. 6 to 10.
Figure 15:
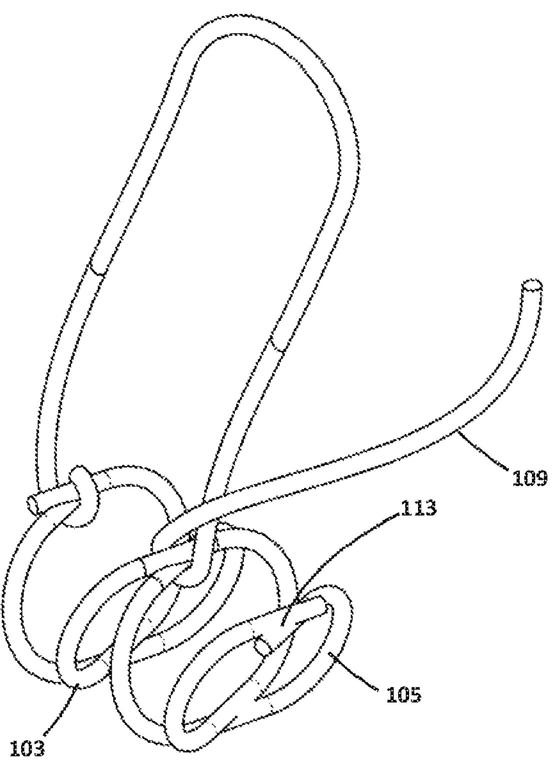
FIG. 15 is a perspective view illustrating the second step of FIG. 14.
Figure 16:
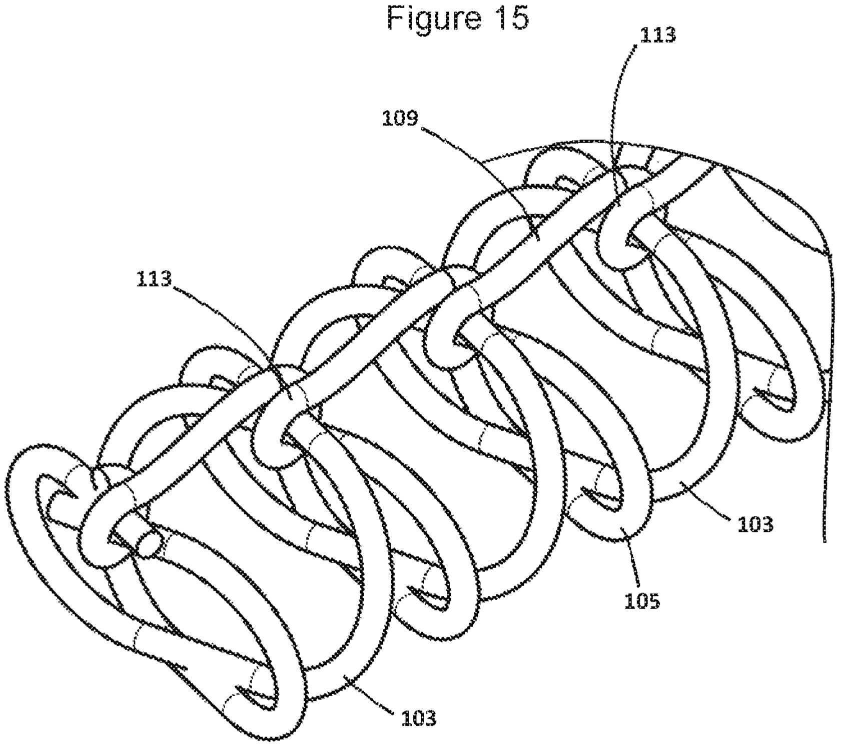
FIG. 16 is a perspective view showing a partly manufactured truss having one bracing member.
Figures 17, 18:
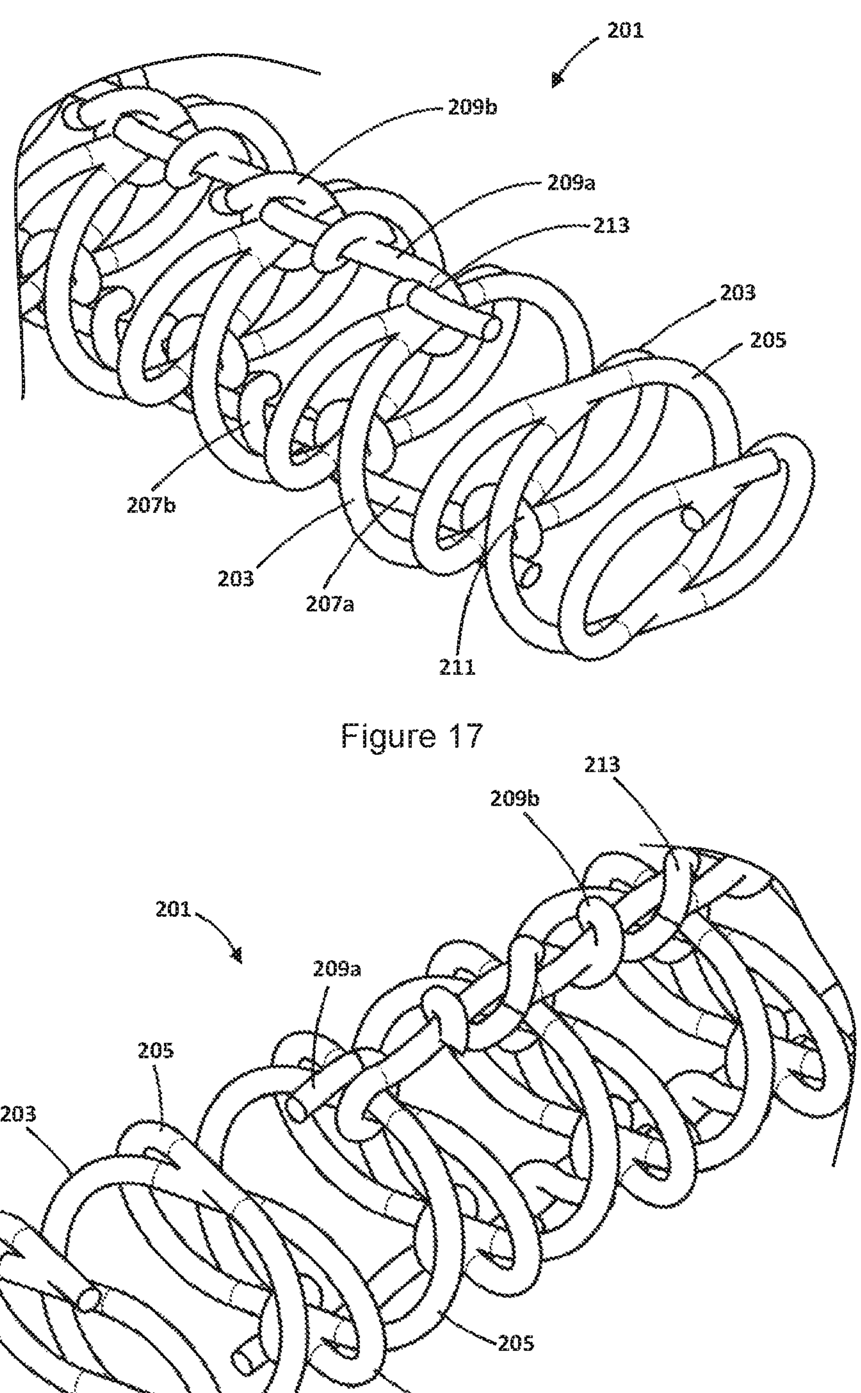
FIG. 17 is a right side perspective view showing a third embodiment truss structure having an indeterminate length, and showing the top and bottom bracing members partially cut-away for clarity.
FIG. 18 is a left side perspective view showing truss structure of FIG. 17, the truss having an indeterminate length, and showing the top and bottom bracing members partially cut-away for clarity.

Referring to FIGS. 13 to 15, to form a first one of the bracing members, in a first step a filament for the bracing member is secured to the wall members at the first forming a 'throw' of filament forward of the secured end.

The 'throw' of filament is passed forward over a node where the wall members 103, 105, intersect, then threaded beneath and around the node before being pulled forward again towards the next node. The entire length of the filament throw is pulled through, forming an interlocking 'loop' around the node once all of the bracing member filament has been pulled through. Tension is applied to the bracing member filament once the loop is formed to interlock the bracing member with the wall members. Retention means keep the bracing member 109 from losing tension while the looping process is repeated for each node 113 along the top spine of the truss 101. This process is repeated for the bracing member 107 for the nodes 111 on the underside of the truss 101.

Embodiment 201

FIGS. 17 to 21 show a truss 201 according to a third embodiment. The truss 201 is substantially as described above for the second embodiment truss 101, but the bracing members 207, 209 each comprise a secondary filament 207*b*, 209*b* that is twisted about a main bracing member filament 207*a*, 209*a*. Each secondary filament 207*b*, 209*b* is wrapped around or twisted with the respective main filament 207*a*, 209*a*, acting to strengthen the bracing members, improve the buckling resistance of the bracing members, and prevent migration of the interlocking loops 211, 213 along the bracing member.

In the embodiment shown, the bracing member secondary filaments 207*b*, 209*b* wrap around the respective main member 207*a*, 209*a* for one full loop between adjacent interlocking nodes 211, 213, and pass over the interlocking loops at the nodes 211, 213 on the outer side of the join. The secondary filaments in this embodiment do not interlock directly to the wall members 203, 205. The secondary filaments 207*b*, 209*b* may help to prevent movement of the interlocking loop in the respective main bracing member filament 207*a*, 209*a*.

Figure 19:
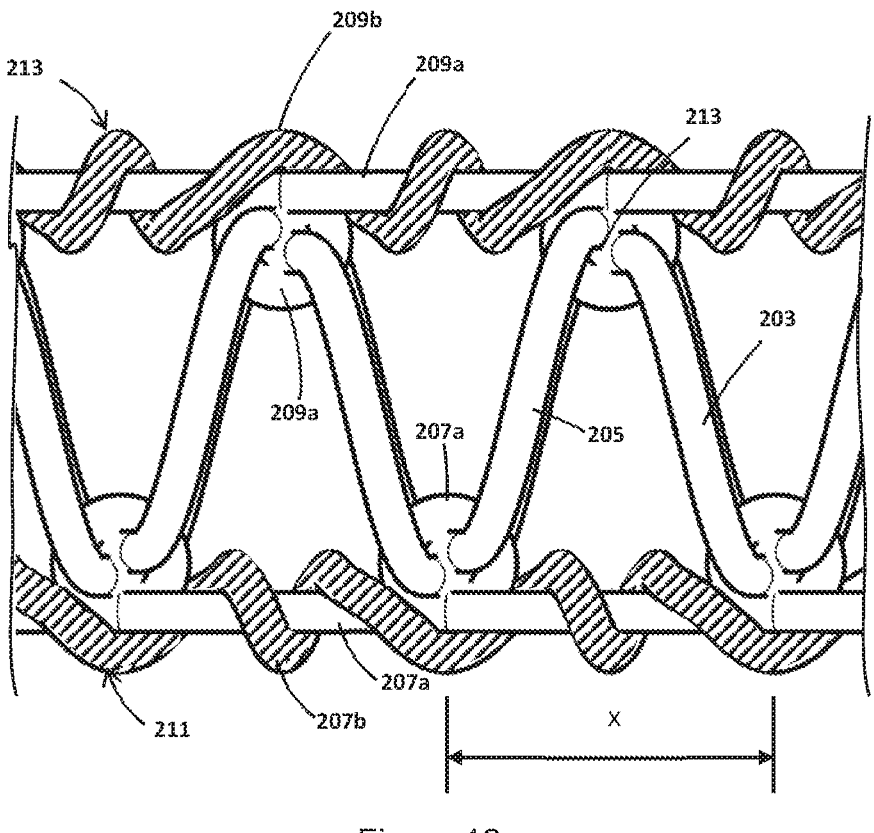
FIG. 19 is a side elevation view corresponding to FIGS. 17 and 18, illustrating the winding of the bracing members.
Figure 20:
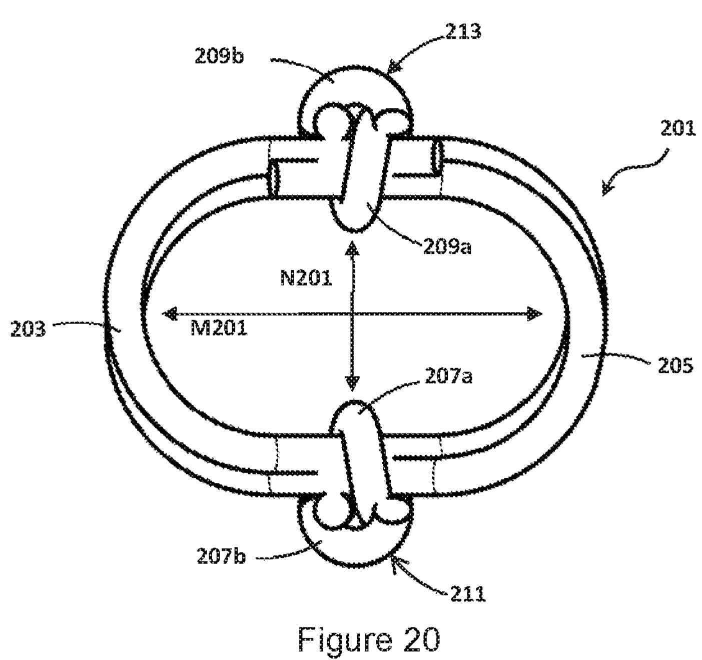
FIG. 20 is an end elevation view (or a transverse section view) of the embodiment of FIGS. 17 to 19.
Figure 21:
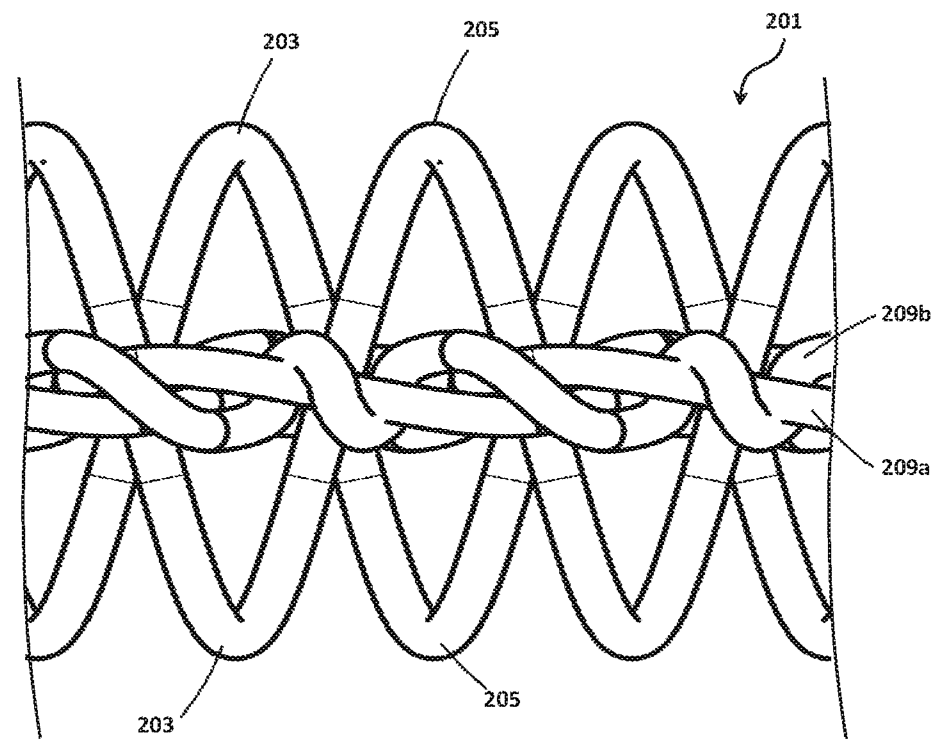
FIG. 21 is a plan view of the embodiment of FIGS. 17 to 20.
Figure 22:
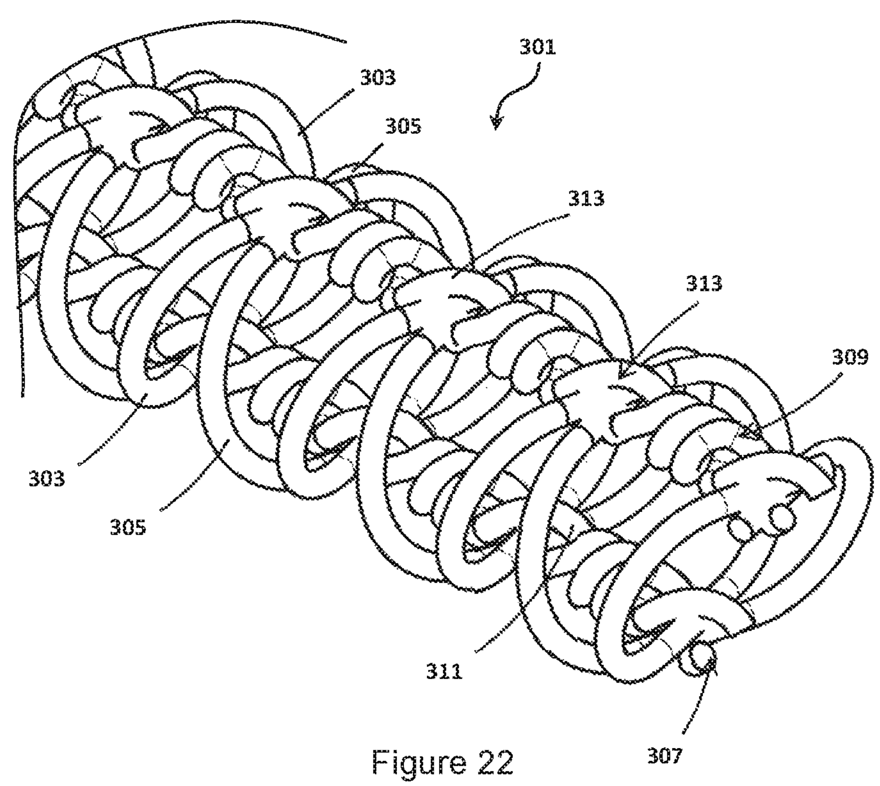
FIG. 22 is a right side perspective view showing a fourth embodiment truss structure having an indeterminate length.
Figure 23:
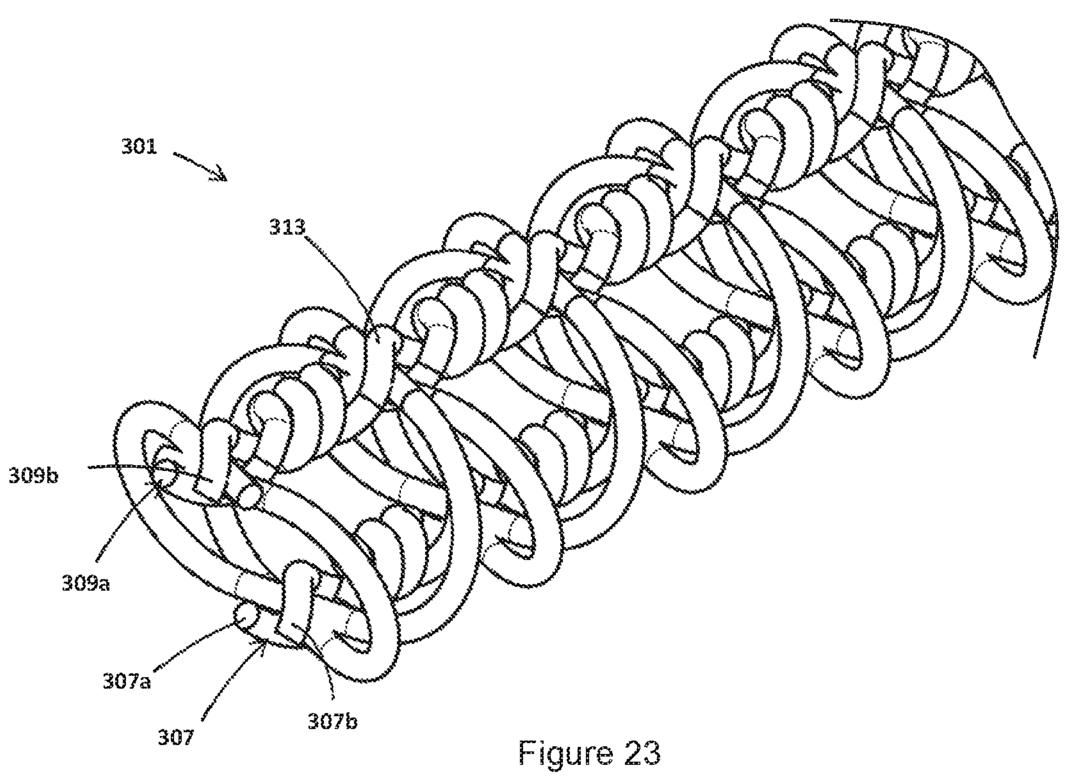
FIG. 23 is a left side perspective view showing truss structure of FIG. 22, the truss having an indeterminate length.
Figure 24:
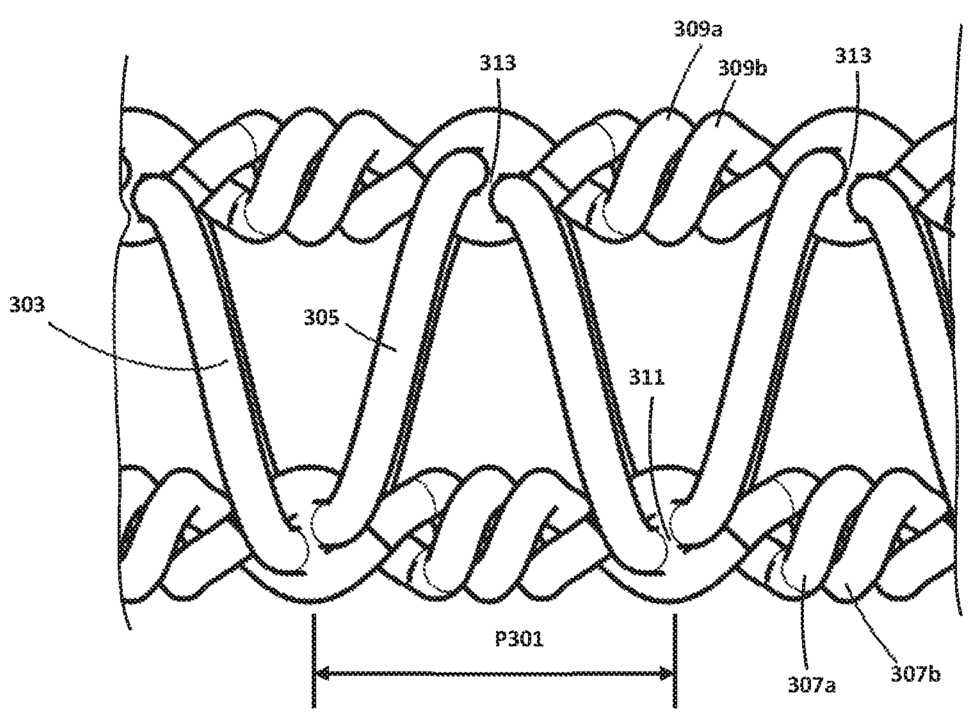
FIG. 24 is a side elevation view corresponding to FIGS. 22 and 23.
Figure 25:
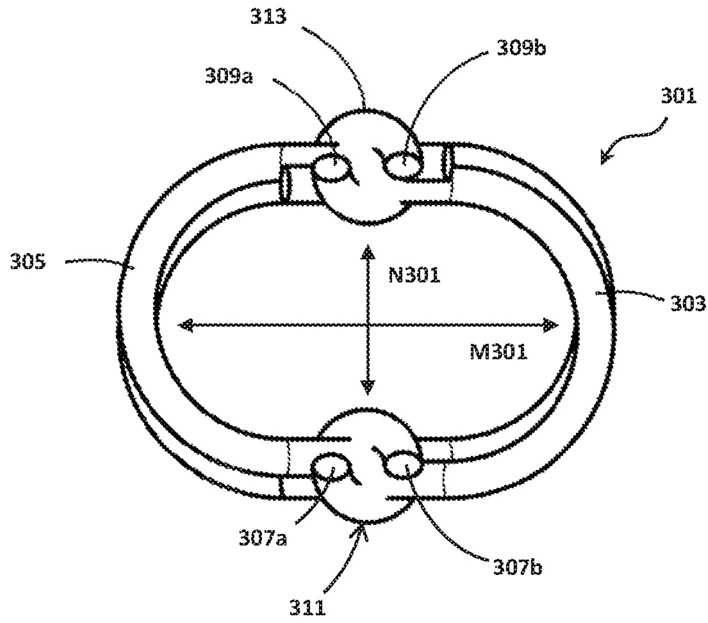
FIG. 25 is an end elevation view (or a transverse section view) of the embodiment of FIGS. 22 to 24.
Figure 26:
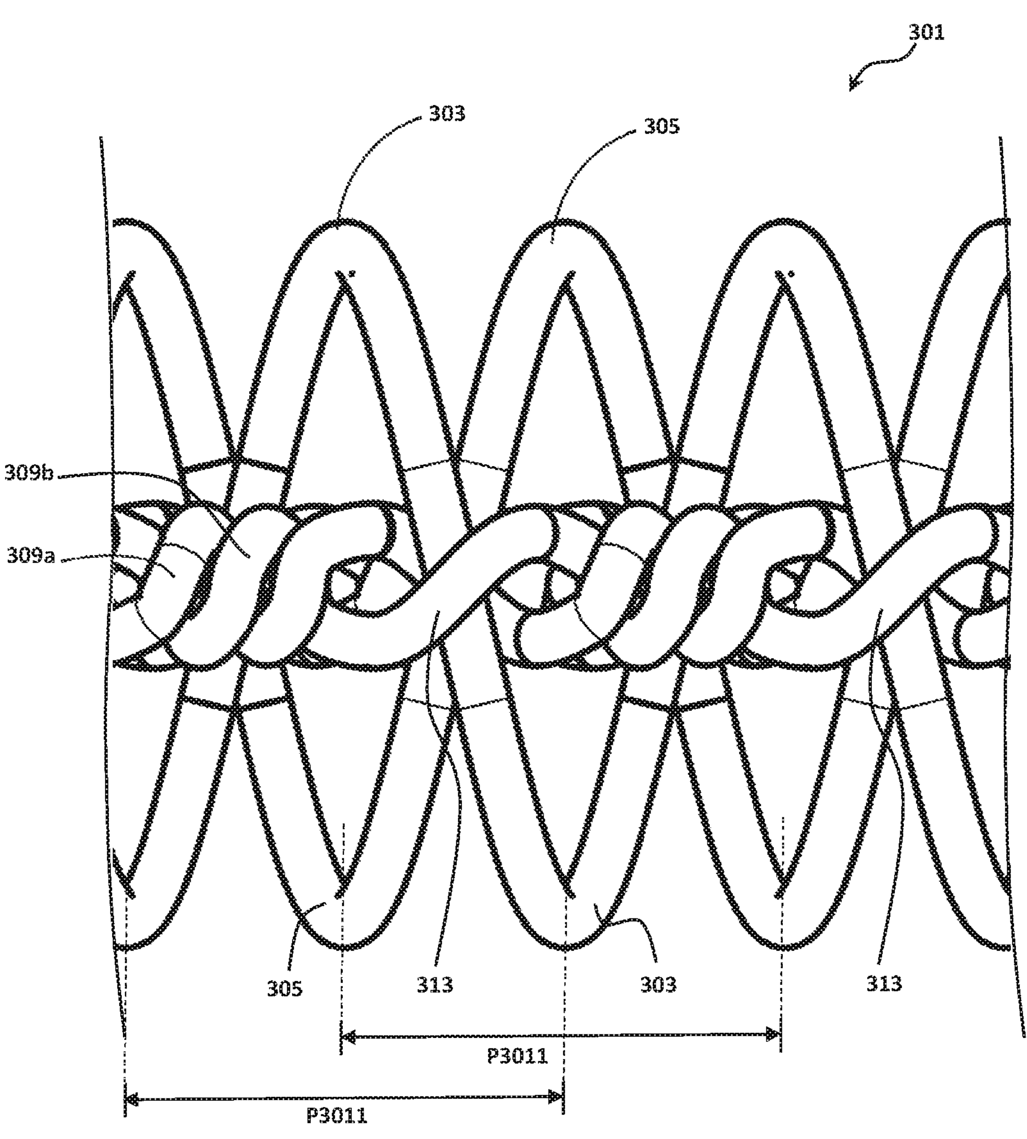
FIG. 26 is a plan view of the embodiment of FIGS. 22 to 25.

As best illustrated in FIG. 19, the winds of the bracing member secondary filaments 207*b*, 209*b* wrap around the respective main member 207*a*, 209*a*, with a consistent rotational direction and wind travel, but with a varying wind angle. The wind angle tends to be shallower, and the length of a wind longer, when the secondary filament is passing over the interlocking loops, whereas the angle will be steeper when the secondary filament is winding around the main filament of the bracing member between nodes.

In some embodiments, the first and second secondary filament 277*b*, 209*b* are wound in opposing directions to each other. This opposite winding may be helpful to prevent the twisting of the manufactured truss once it is removed from the mandrel.

Embodiment 301

FIGS. 22 to 26 show a truss 301 according to a fourth embodiment. As for the previously described embodiments, the truss 301 comprises a first wall member 303 having a generally helical form with a left-hand wind, and an oppositely wound second wall member 305 having a generally helical form with a right-hand wind. The pitch length P301 of the first wall member 303 is the same as the pitch length of the second wall member 305. The truss 301 forms a tube and channel that is oval in cross section (FIG. 25), with a major dimension M301, and a minor dimension N301 that is less than the major dimension.

The truss 301 has two elongate bracing members 307, 309 that extend longitudinally along the wall of the truss 301, at the top and bottom sides, in line with the minor axis N301. Each bracing member comprises two filaments 307*a*, 307*b*, 309*a*, 309*b* twisted together, with the wall members 303, 305 captured and held between the two filaments of the respective bracing member at the respective wall member cross-over nodes 211, 213.

In the embodiment shown, the bracing member filaments 207*a*, 207*b*, 209*a*, 209*b* form two full twists along the pitch length of the wall members, but in alternative embodiments there may be more or fewer twists depending on the thickness of the bracing member filaments and the pitch length P301 of the wall members. The pitch length P301 is determined by the number of twists between nodes 311, 313.

In some embodiments, the filaments 307*a*, 307*b* of the first bracing member 307 are twisted in the opposite direction to the filaments 309*a*, 309*b* of the second bracing member 309. This opposite winding of the top and bottom bracing members may be helpful to prevent the twisting of the manufactured truss 301 once it is removed from the mandrel.

Embodiment 401

FIGS. 31 to 35 show a truss 401 according to a fifth embodiment. The truss 401 is substantially as described above for the first embodiment truss 1 with the first and second wall members 403, 405 wound around the bracing members 407, 409 at nodes 411, 413. However, in this embodiment, the wall members are not helical. The first wall member is a right-side wall member, and the second wall member is a left-side wall member.

Figure 33:
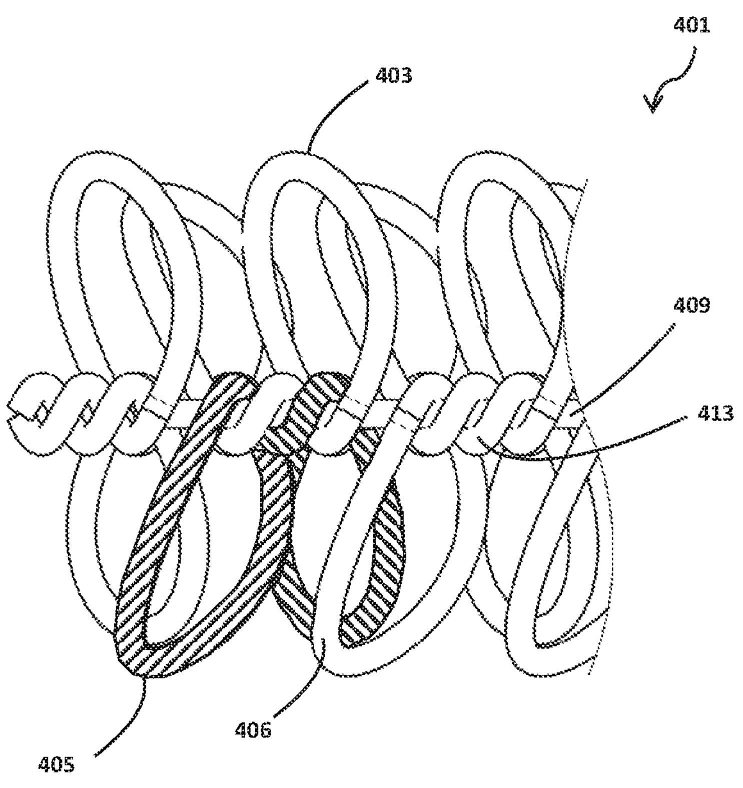
FIG. 33 is a top view of a portion of the truss of FIGS. 31 and 32, illustrating the winding of the truss wall members.
Figure 34:
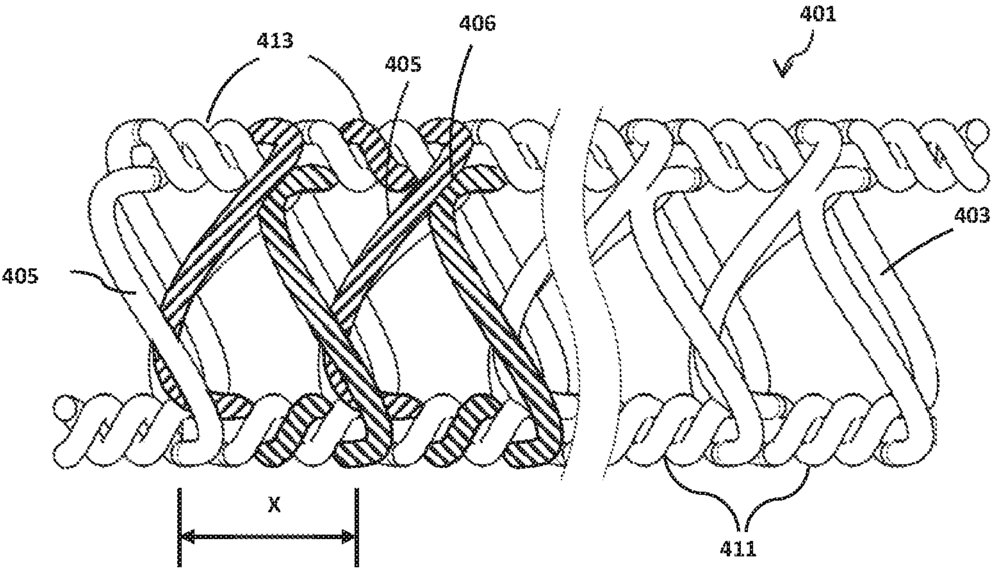
FIG. 34 is a side view of a portion of the truss of FIGS. 31 to 33, illustrating the winding of the truss wall members.

The first and second wall members 403, 405 are wound such that they remain generally on the same side of the bracing members along the length of the truss. At each node 411, 413, each wall member 403, 405 is looped one and a half times around the respective bracing member 407, 409, exiting the node on the same side it entered the node. This is best illustrated in FIGS. 33 and 34, where a length of the second wall member 405 is shaded to illustrate the nature of the winding. The number of loops of each wall member 403, 405 about the respective bracing member 407, 409 is at least one but may vary between embodiments, in the embodiment shown the wall members are wrapped 540 degrees (i.e one and a half turns) about the bracing member. In another embodiment, the wall members may be wrapped 720 degrees (i.e two turns) about the bracing member, or more.

Referring to the plan view of FIG. 33, subsequent 'winds' of each wall member 403, 405 extending between the first and second bracing members 407, 409, may overlap with or abut a previous wall member wind at a contact point 406. This contact point 406 will generally occur at about a midpoint between the first and second bracing members 407, 409 but may occur at other positions.

From FIGS. 33 and 34, it can also be seen, that the direction of the winds of the wall members 403, 405 about the first bracing member 407 is opposite to the direction of the winds of the wall members 403, 405 about the second bracing member 409. This opposite winding may be helpful to prevent the twisting of the manufactured truss 401 once it is removed from the mandrel after manufacture.

Figures 35, 36:
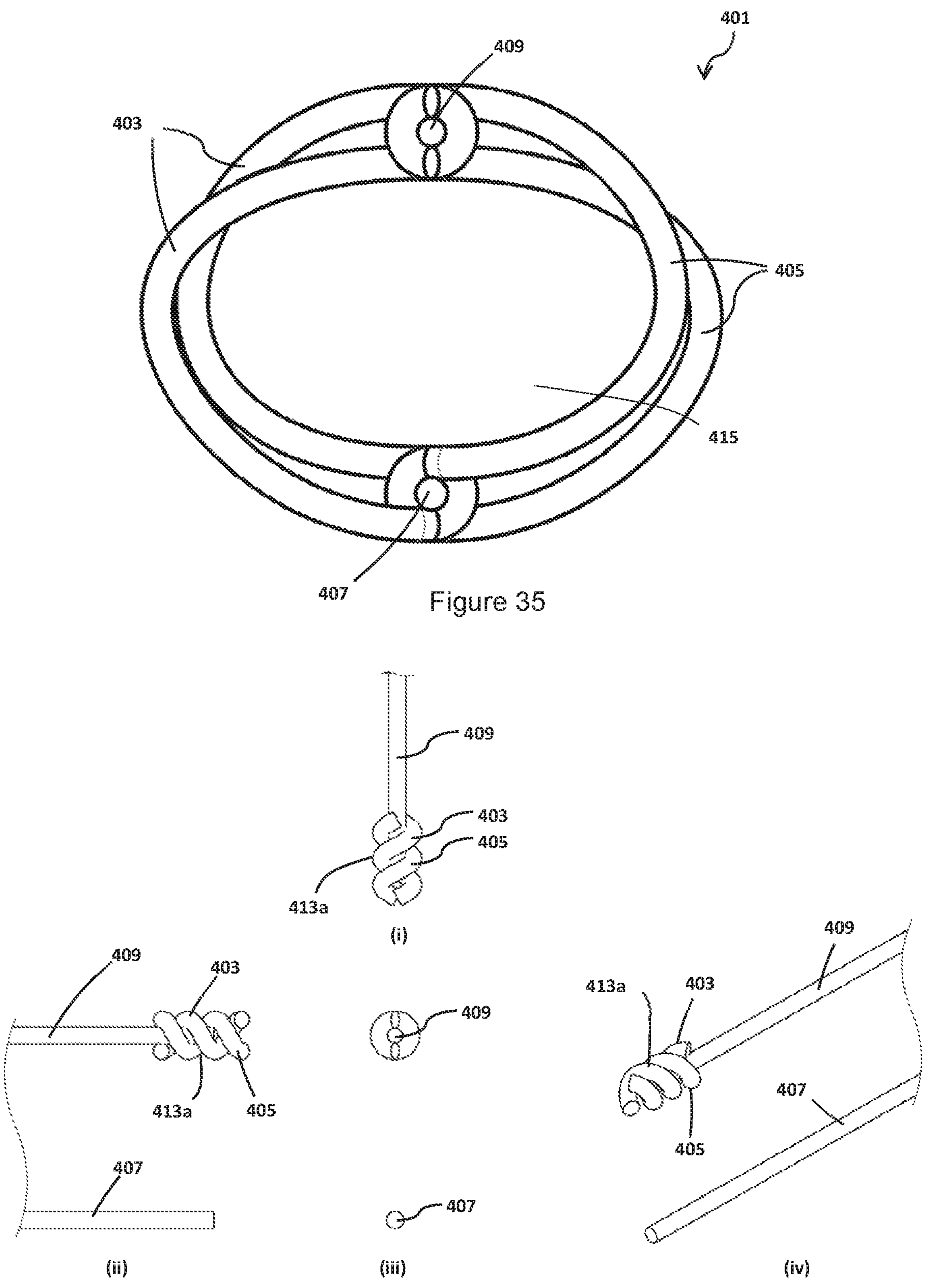
FIG. 35 is an end view (or a transverse section view) of the truss of FIGS. 31 to 34.
FIGS. 36(*i*) to 36(*iv*) illustrate a first step in fabricating the truss of FIGS. 31 to 35, where FIG. 36(*i*) is a top view, FIG. 36(*ii*) is a side view, FIG. 36(*iii*) is an end view, and FIG. 36(*iv*) is a perspective view.

FIGS. 36(*i*) to 39(*iv*) illustrate the formation of this embodiment truss 401. In a first step shown in FIGS. 36(*i*) to 36(*iv*), the first and second wall members 405, 407 are twisted around the top bracing member 409 for 1.5 loops, forming a first node 413*a*.

Figure 37:
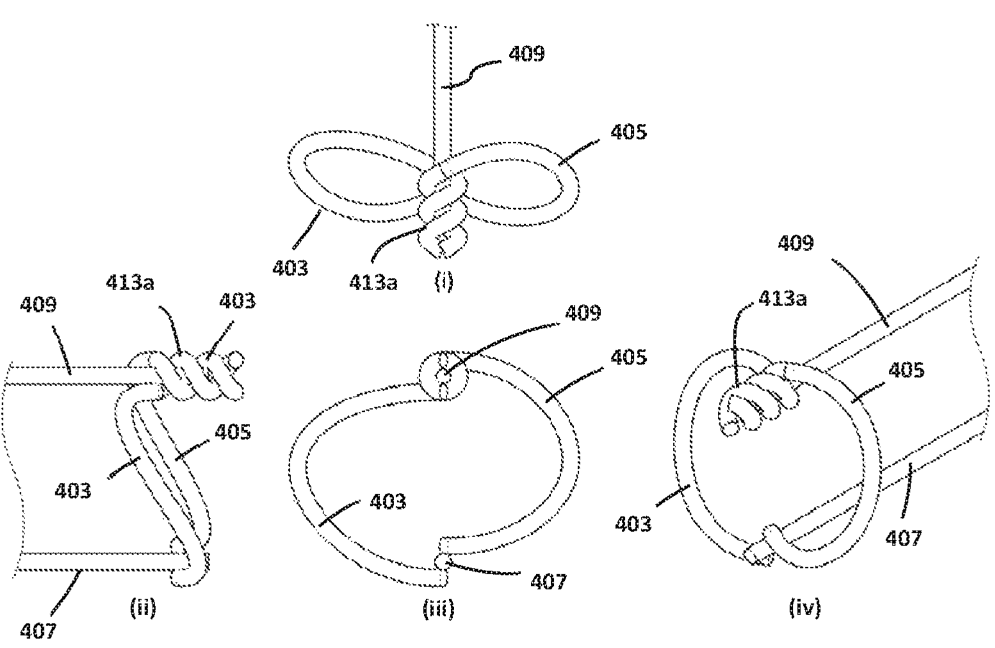
FIGS. 37(*i*) to 37(*iv*) illustrate a second step in fabricating the truss of FIGS. 31 to 35, where FIG. 37(*i*) is a top view, FIG. 37(*ii*) is a side view, FIG. 37(*iii*) is an end view, and FIG. 37(*iv*) is a perspective view.

In second and third steps shown in FIGS. 37(*i*) to 38(*iv*), the first and second wall members 405, 407 are then drawn down to the lower bracing member 407, to a point approximately directly below their exit from the first node 413*a*, before being twisted together about the lower bracing member 407 at a new node 411. The wall members 403, 405 are twisted in an opposite direction to the direction of twisting about the upper bracing member 409.

Figure 38:
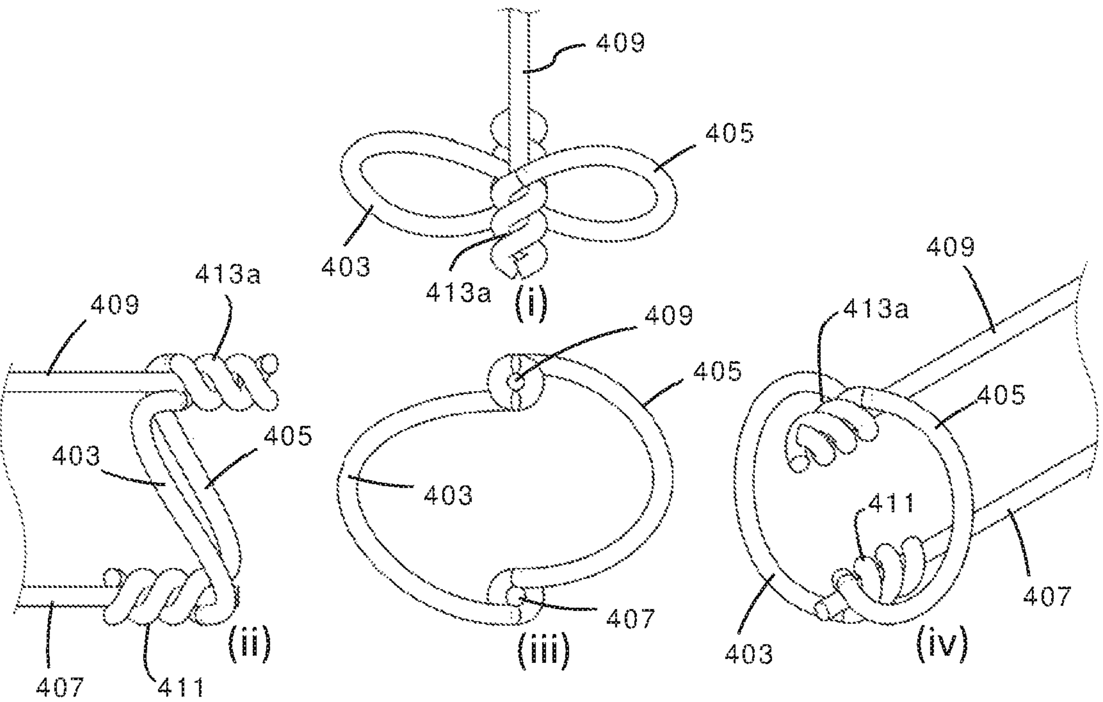
FIGS. 38(*i*) to 38(*iv*) illustrate a third step in fabricating the truss of FIGS. 31 to 35, where FIG. 38(*i*) is a top view, FIG. 38(*ii*) is a side view, FIG. 38(*iii*) is an end view, and FIG. 38(*iv*) is a perspective view.
Figure 39:
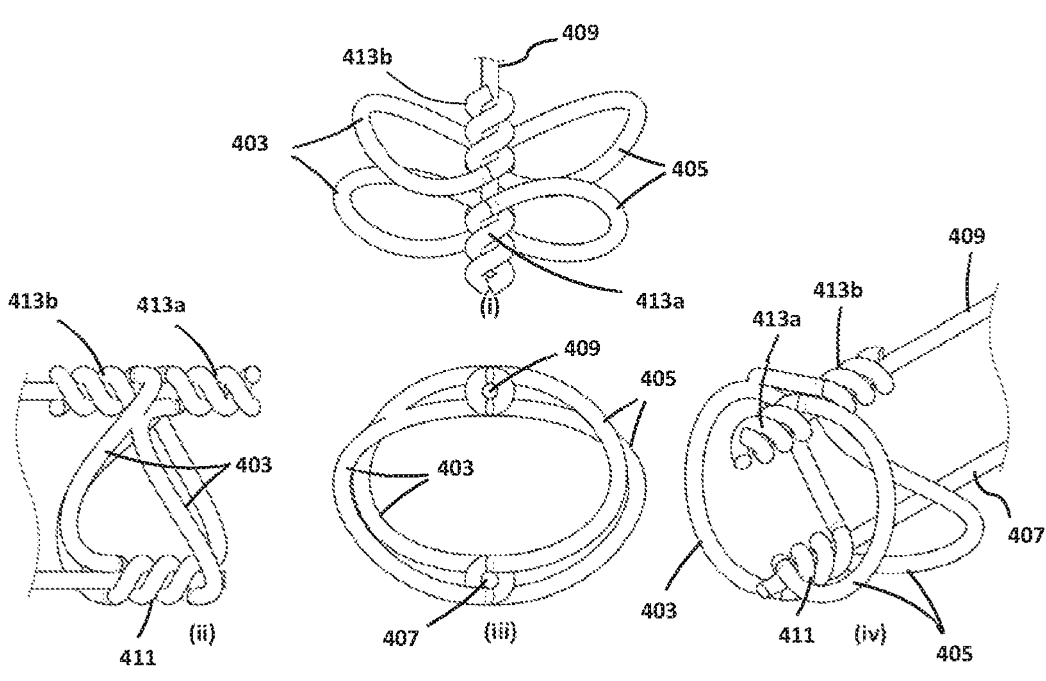
FIGS. 39(*i*) to 39(*iv*) illustrate a fourth step in fabricating the truss of FIGS. 31 to 35, where FIG. 39(*i*) is a top view, FIG. 39(*ii*) is a side view, FIG. 39(*iii*) is an end view, and FIG. 39(*iv*) is a perspective view.
Figure 40:
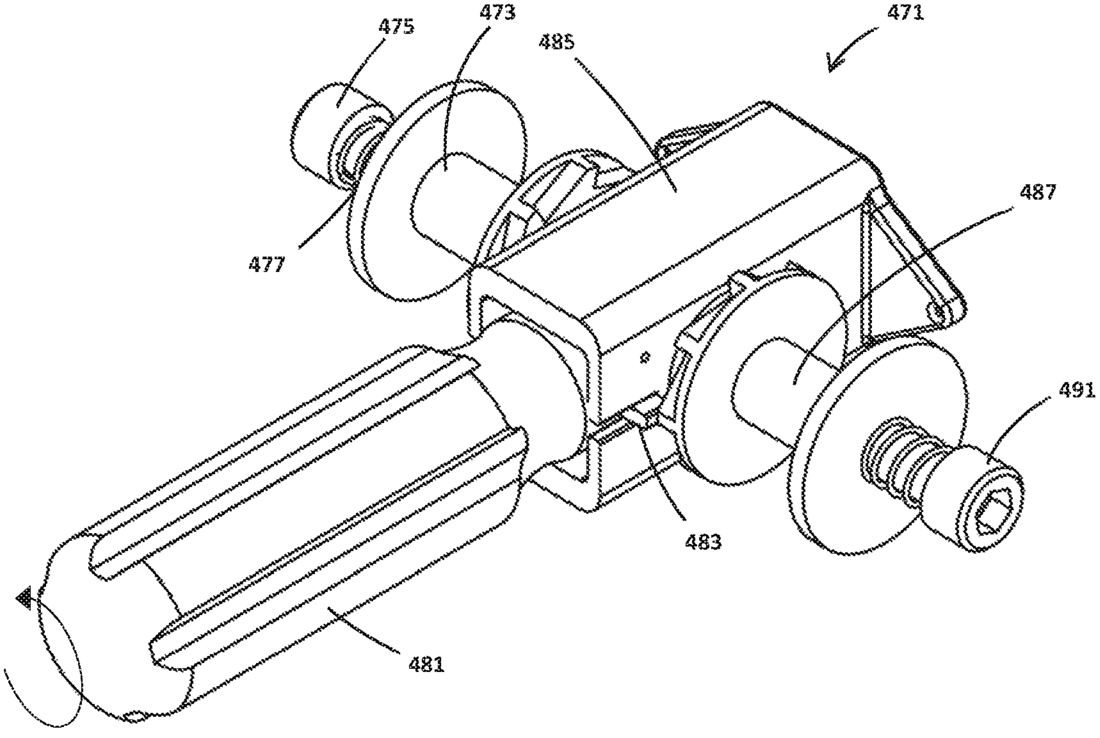
FIG. 40 is a rear perspective view of an apparatus for manufacturing various embodiment trusses described herein.
Figure 41:
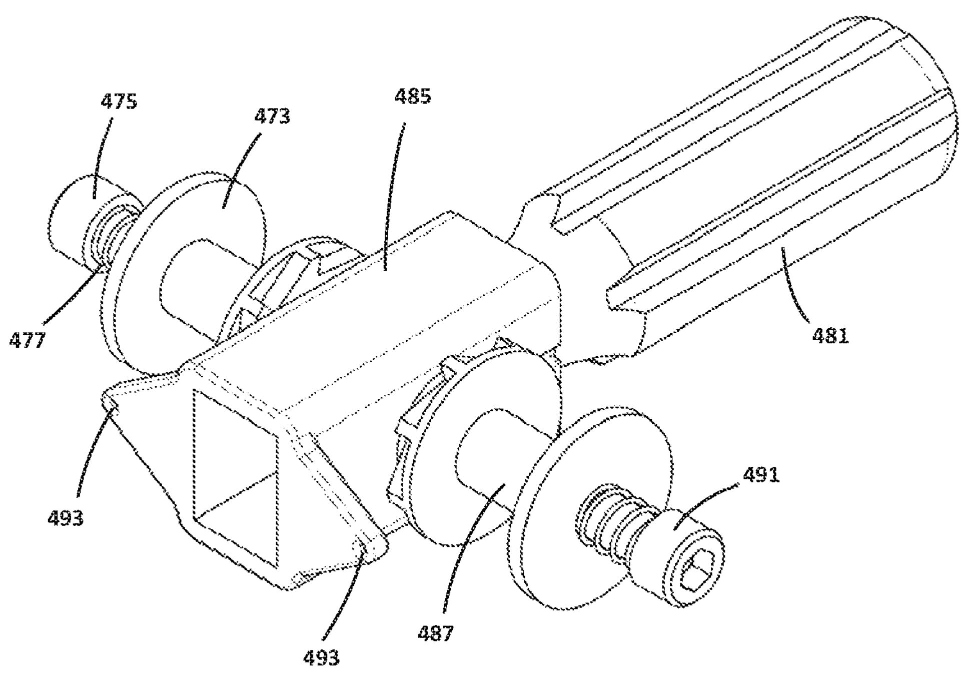
FIG. 41 is a front perspective view of the manufacturing apparatus of FIG. 40.
Figure 42:
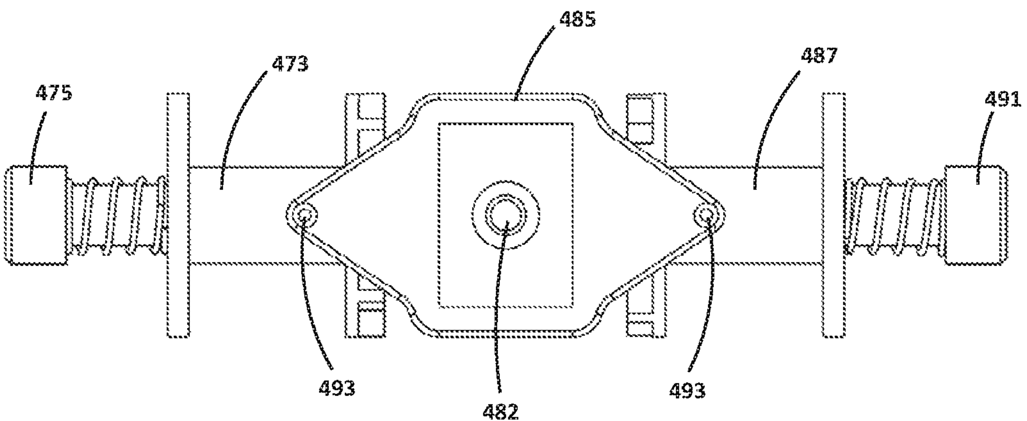
FIG. 42 is a front elevation view of the manufacturing apparatus of FIGS. 40 and 41.
Figure 43:
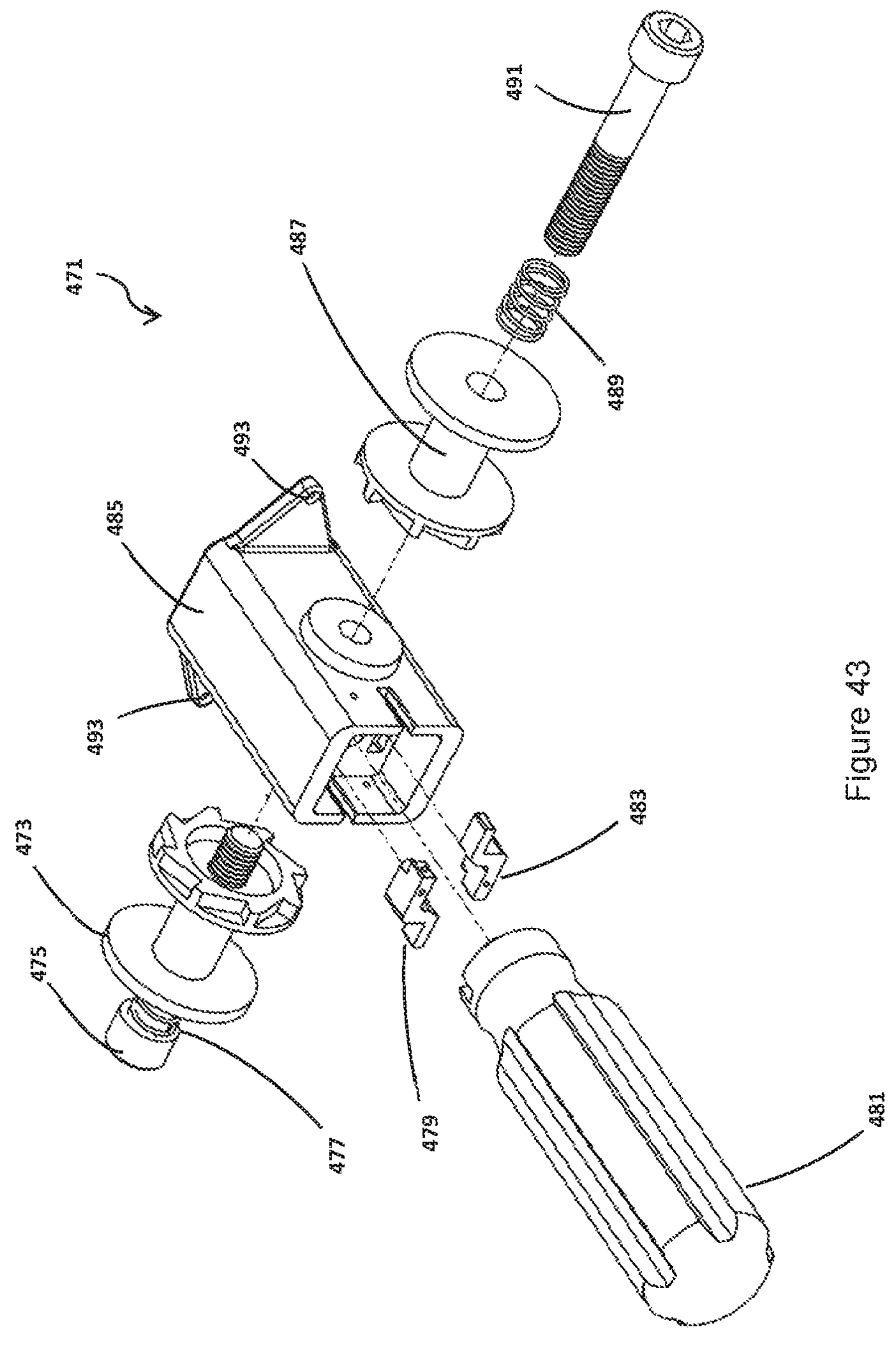
FIG. 43 is an exploded rear perspective view of the manufacturing apparatus of FIGS. 40 to 42.
Figures 44A, 44B:
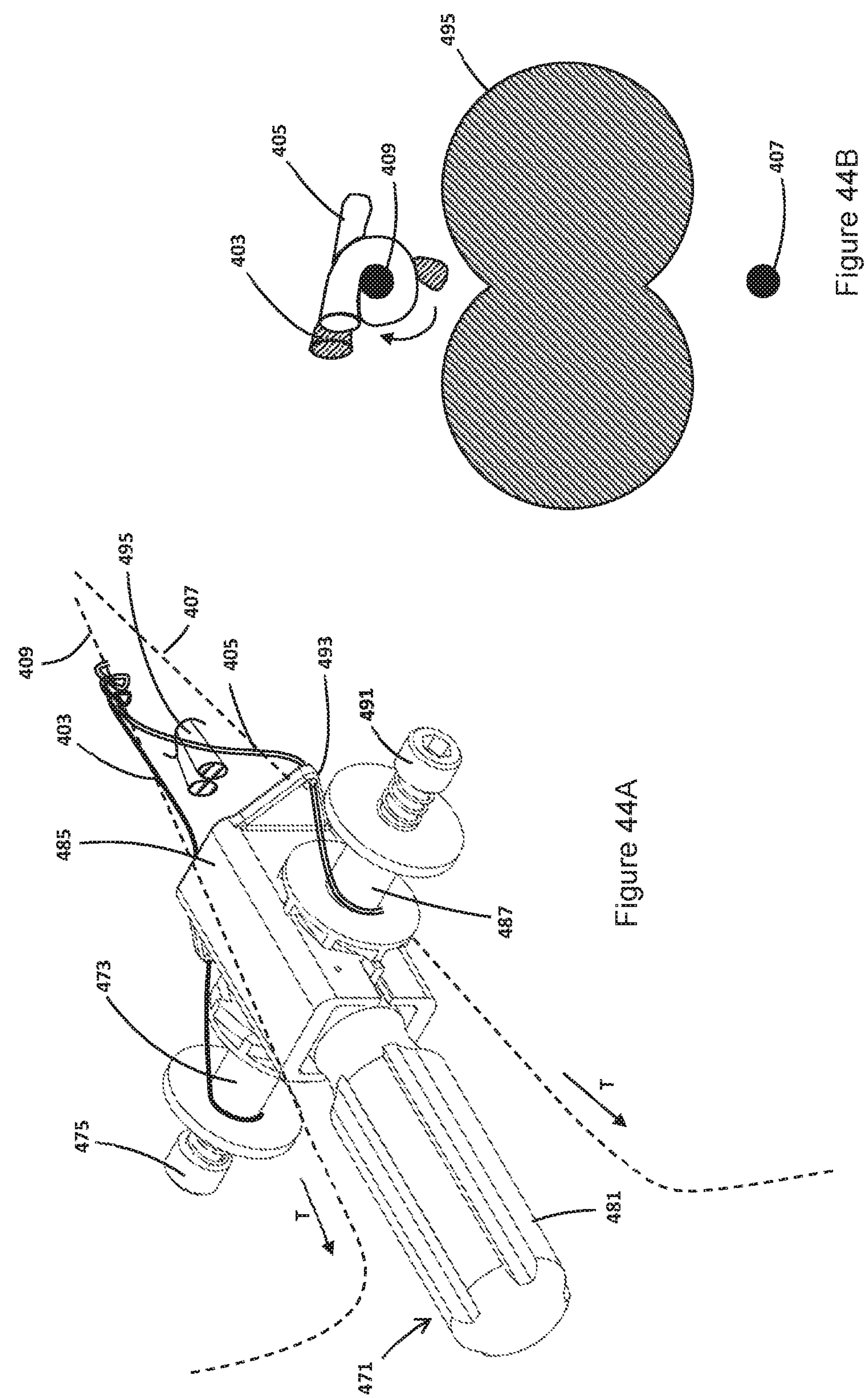
FIGS. 44A and 44B illustrate use of the manufacturing apparatus of FIGS. 40 to 43 in a first step in fabricating the embodiment of FIGS. 31 to 35, where
Figures 45A, 45B:
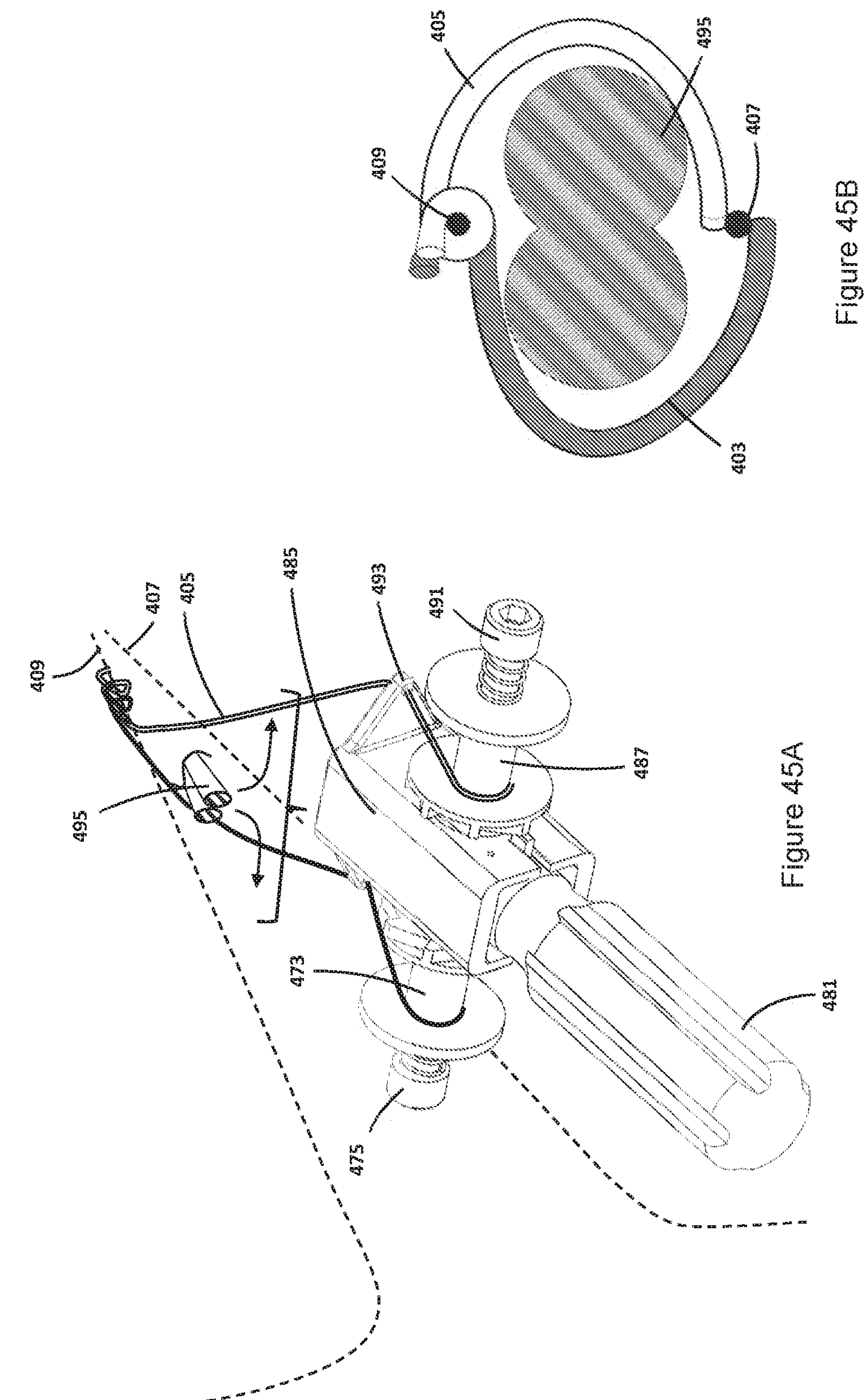
FIGS. 45A and 45B illustrate use of the manufacturing apparatus of FIGS. 40 to 43 in a second step in fabricating the embodiment of FIGS. 31 to 35, where
Figures 46A, 46B:
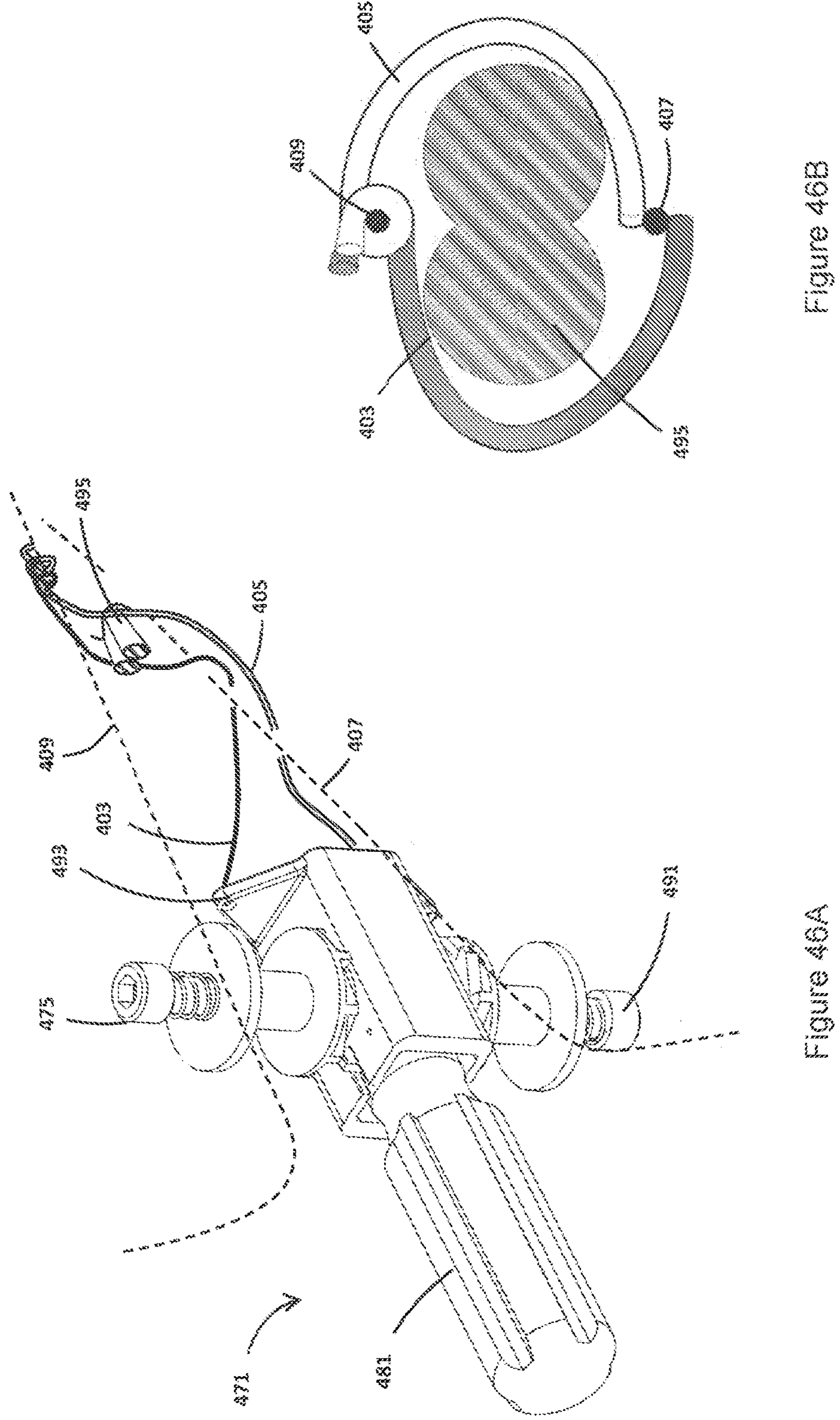
FIGS. 46A and 46B illustrate use of the manufacturing apparatus of FIGS. 40 to 43 in a third step in fabricating the embodiment of FIGS. 31 to 35, where
Figures 47A, 47B, 47C:
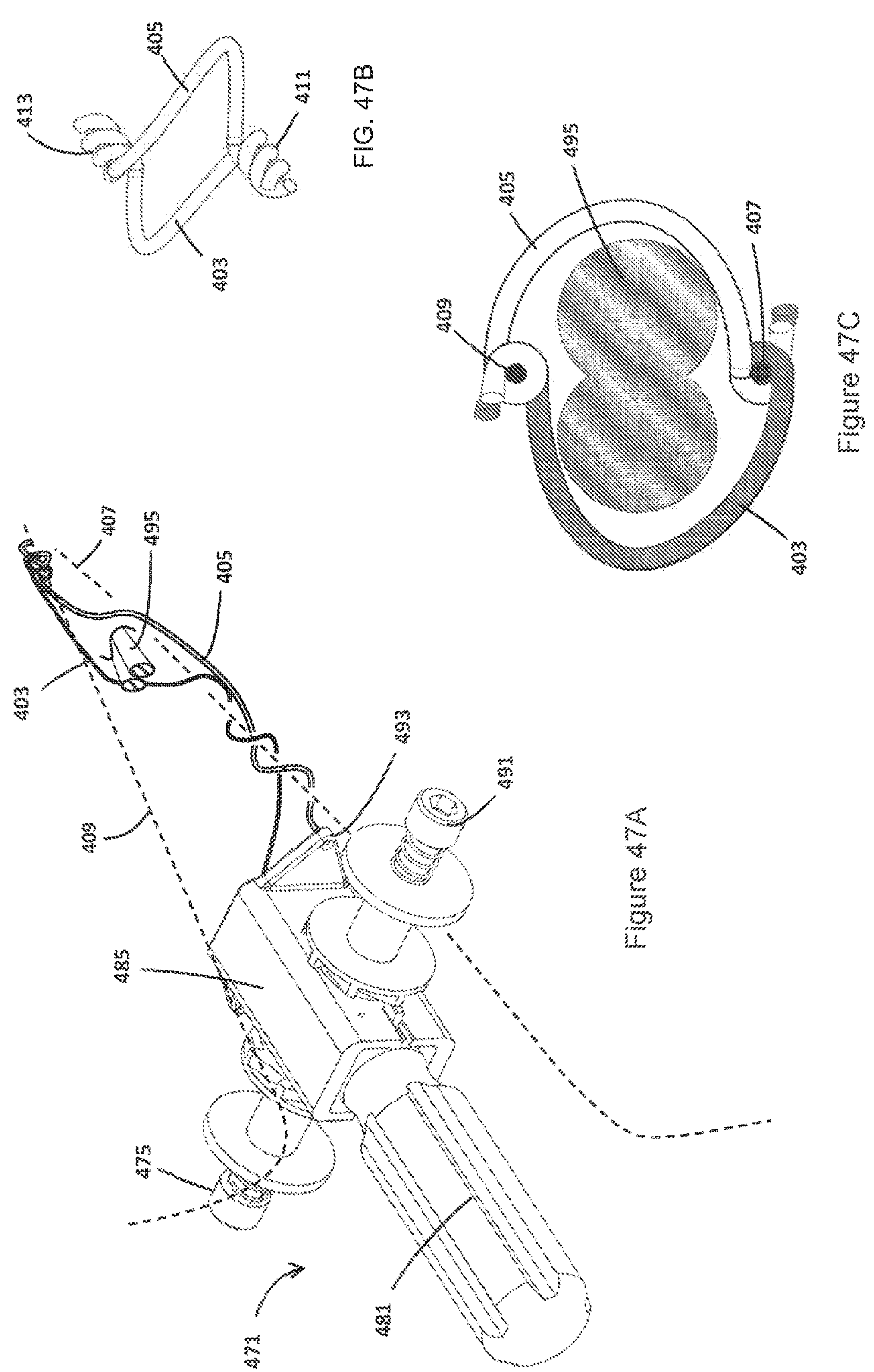
FIGS. 47A to 47C illustrate use of the manufacturing apparatus of FIGS. 40 to 43 in a fourth step in fabricating the embodiment of FIGS. 31 to 35, where
Figures 48A, 48B, 48C:
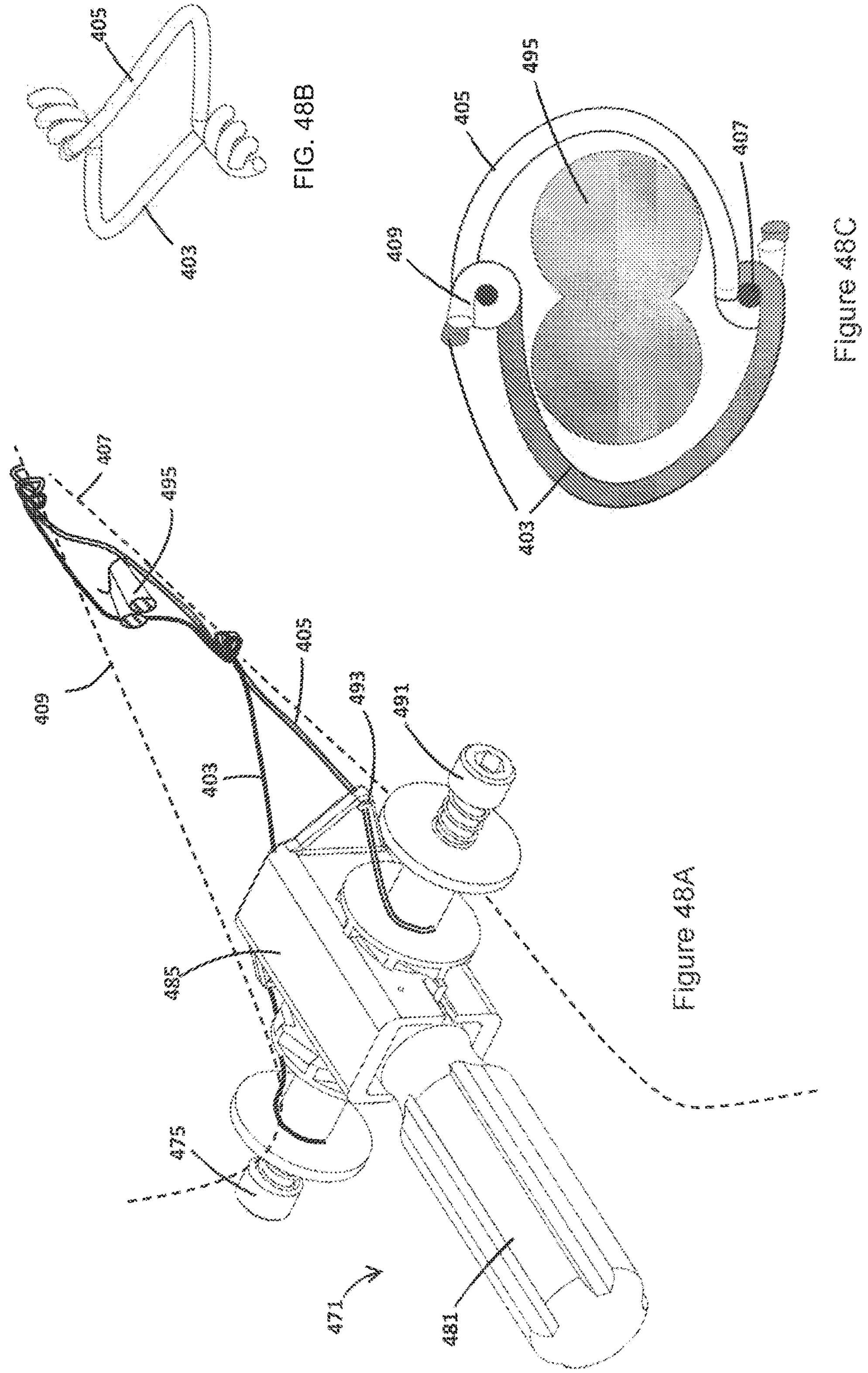
FIGS. 48A to 48C illustrate use of the manufacturing apparatus of FIGS. 40 to 43 in a fifth step in fabricating the embodiment of FIGS. 31 to 35, where
Figure 49:
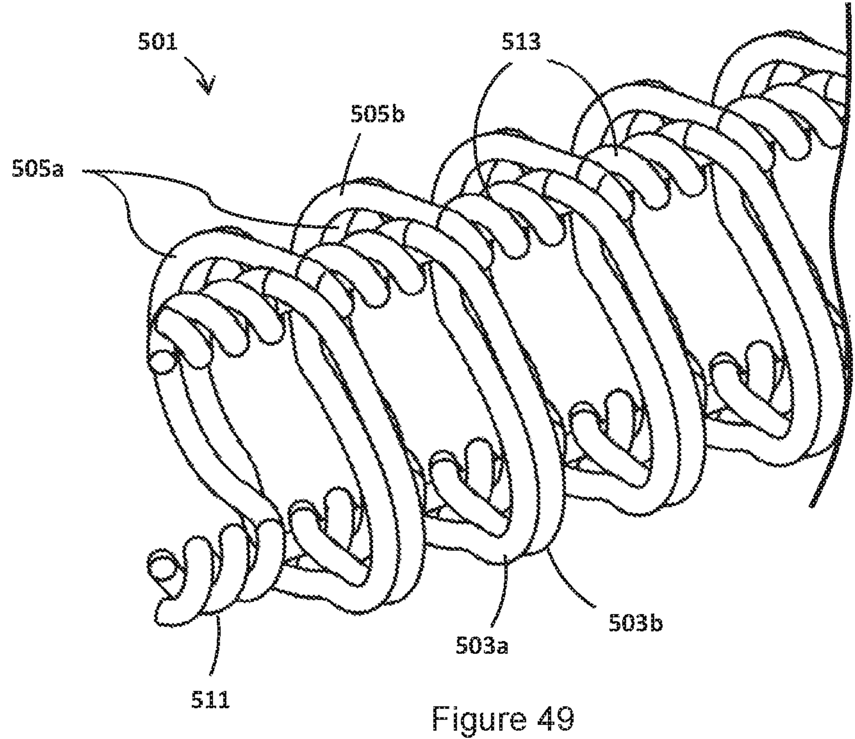
FIG. 49 is a left side perspective view of a sixth embodiment truss structure having an indeterminate length.
Figure 50:
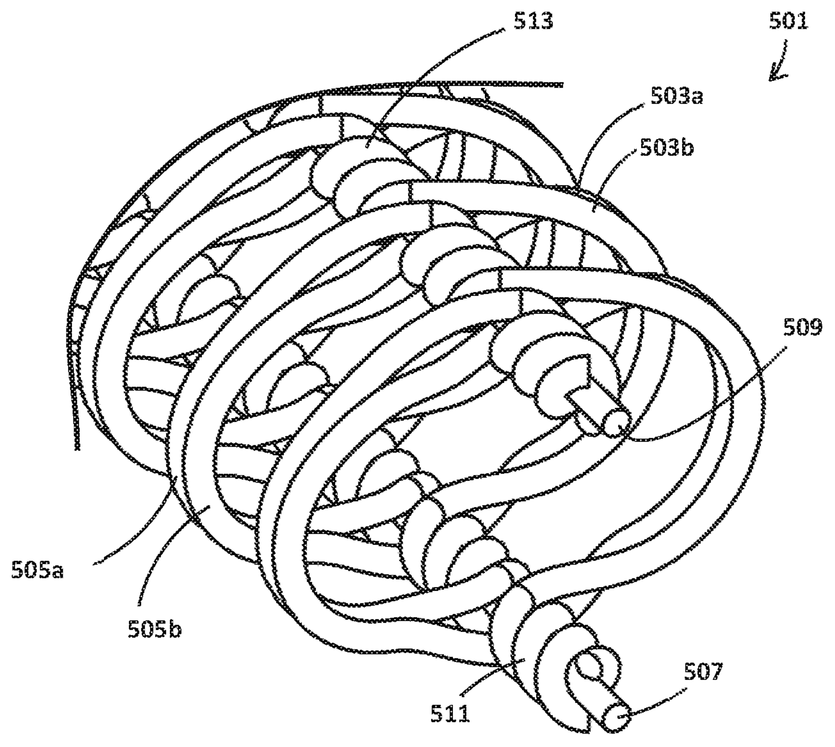
FIG. 50 is a front right-side perspective view of the truss of FIG. 49.
Figure 51:
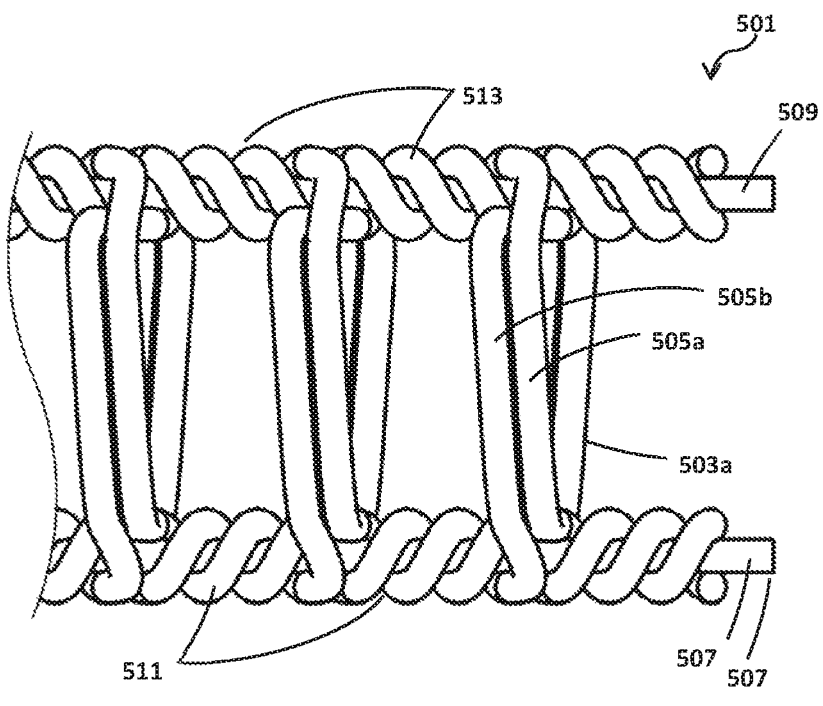
FIG. 51 is a side elevation view of a portion of the truss of FIGS. 49 and 50, illustrating the winding of the side truss wall members.
Figure 52:
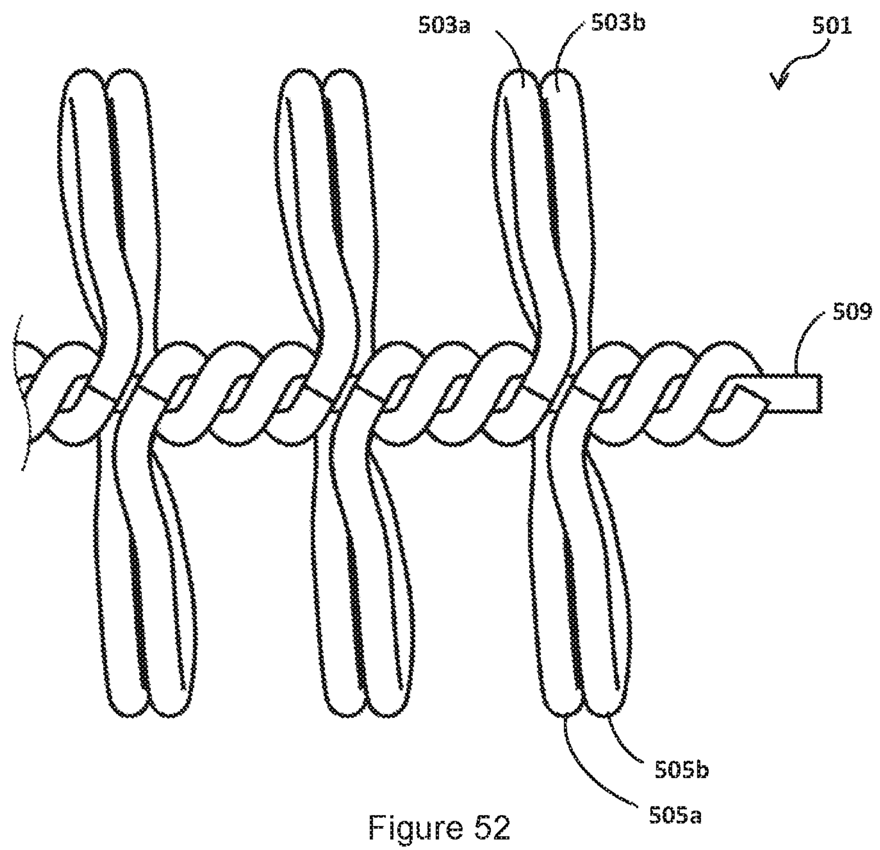
FIG. 52 is a top view of a portion of the truss of FIGS. 49 to 51.
Figures 53, 54:
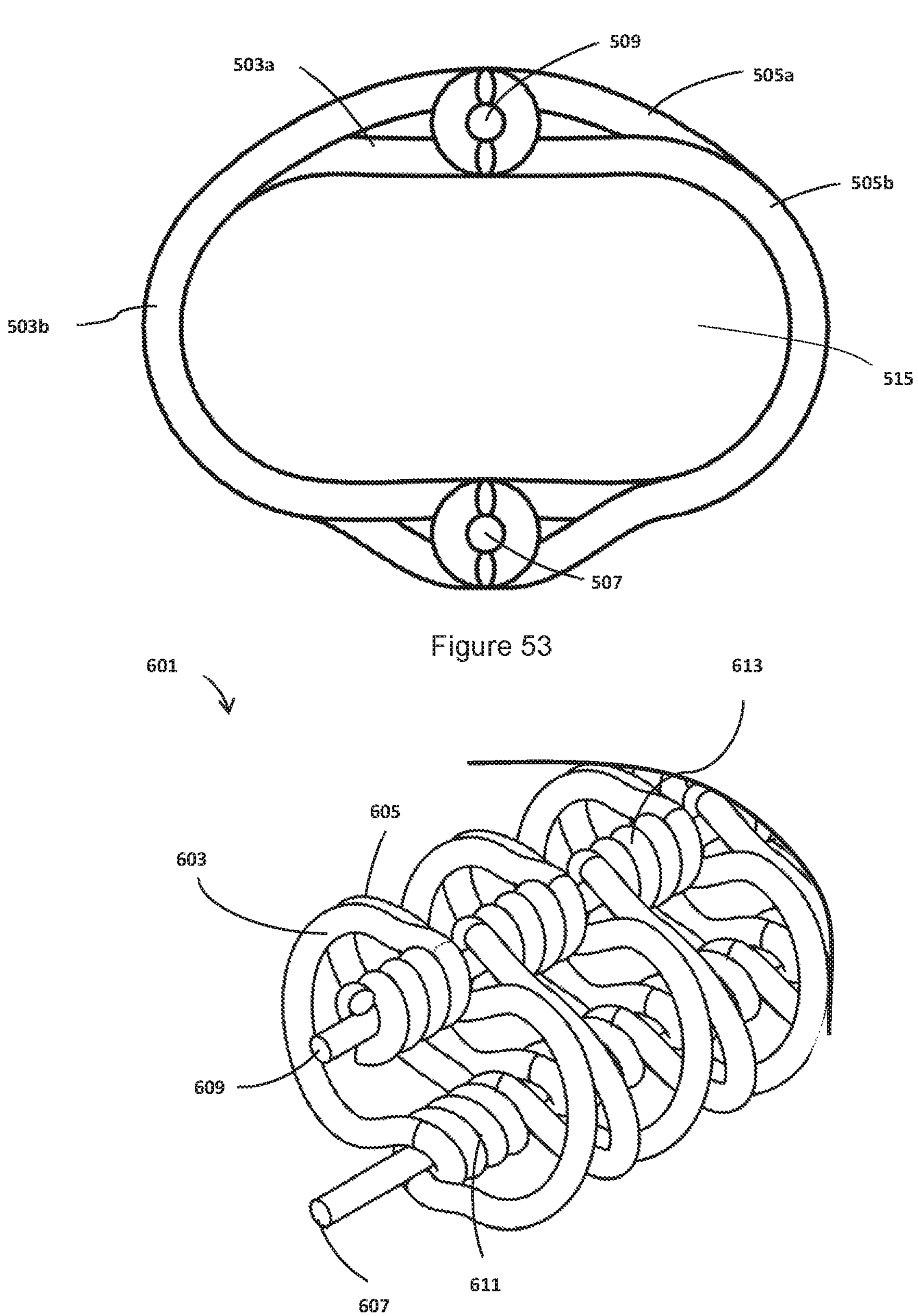
FIG. 53 is an end view (or a transverse section view) of the truss of FIGS. 49 to 52.
FIG. 54 is a left side perspective view of a further embodiment truss structure having an indeterminate length.
Figure 55:
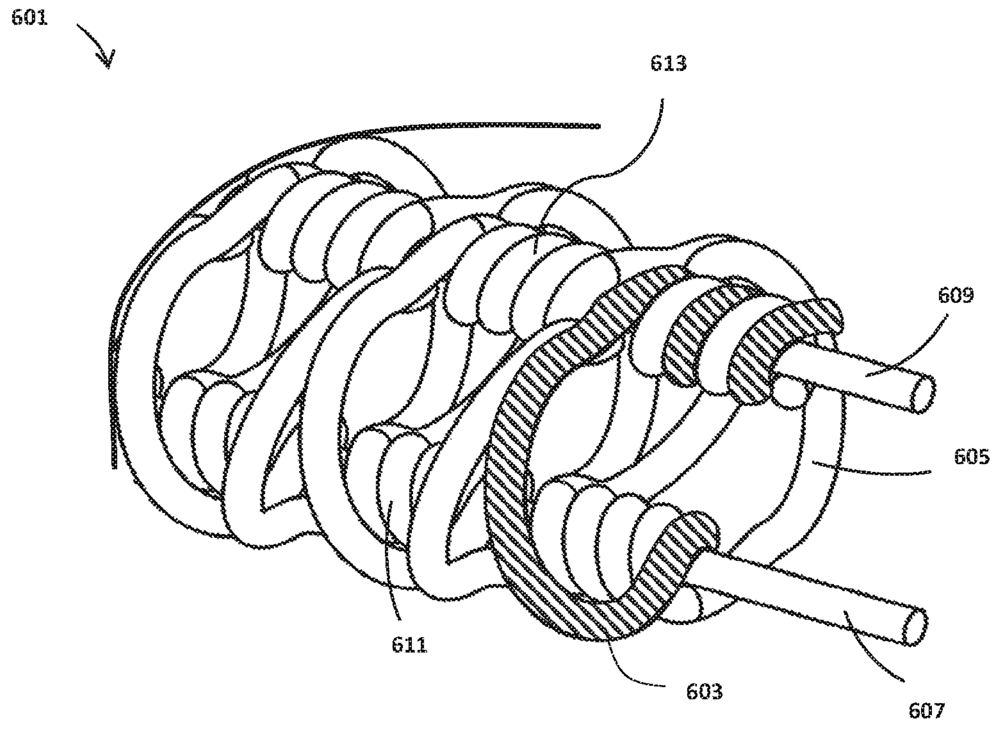
FIG. 55 is a right side perspective view of the truss structure of FIG. 54, with a portion of one of the truss members hatched.
Figure 56:
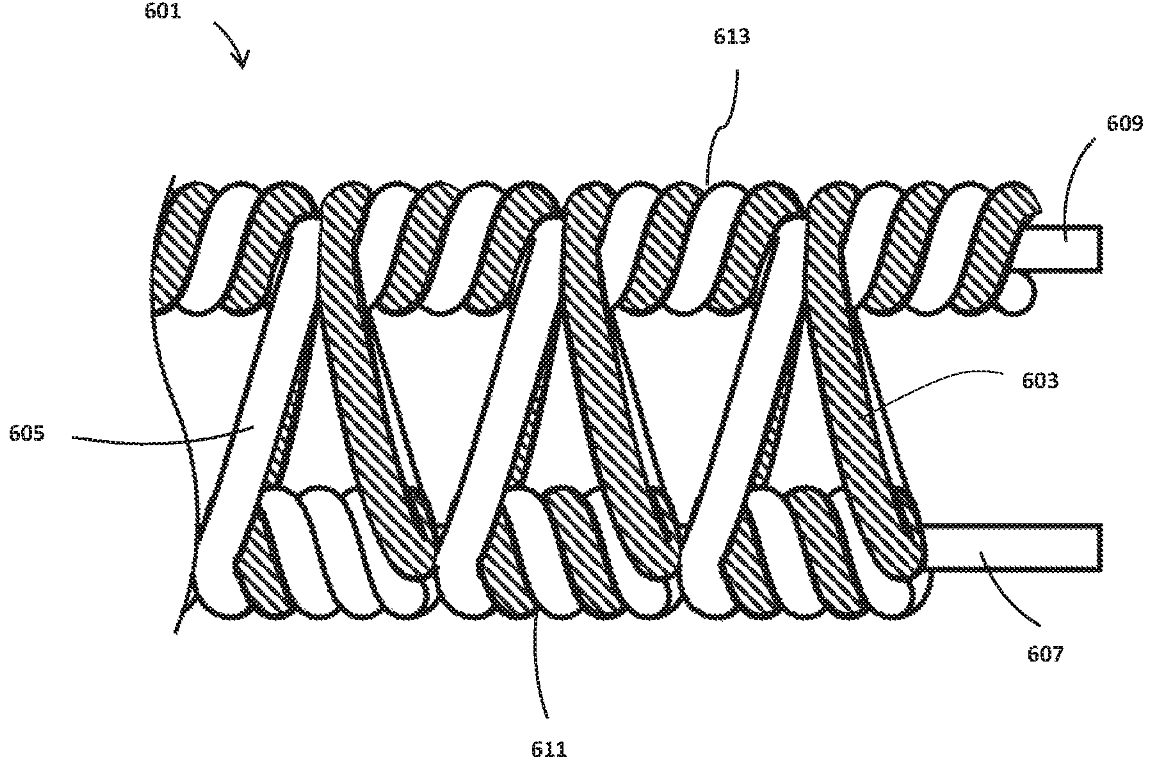
FIG. 56 is a side view of the truss structure of FIGS. 54 and 55, with one of the truss members hatched.
Figure 57:
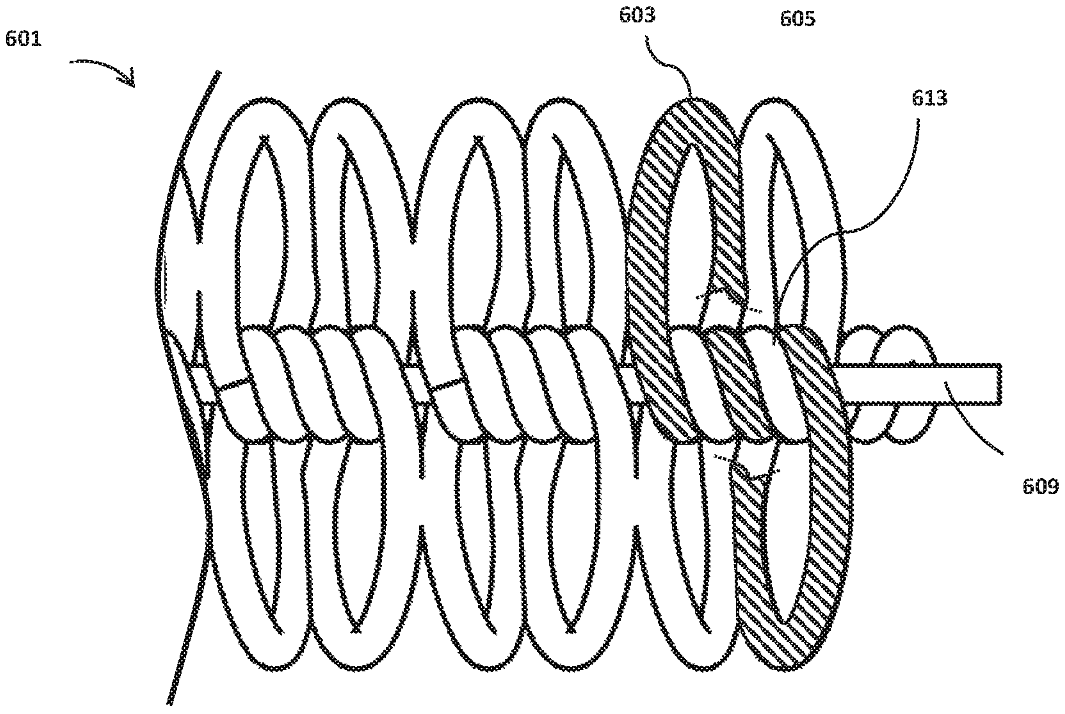
FIG. 57 is a top view of the truss structure of FIGS. 54 to 56, with a portion of one of the truss members hatched.

As best illustrated in FIG. 38(*iii*), the first wall member 403 exits the first node 413*a* at a bottom of the top bracing member 409 and enters the subsequent node 411, on the lower bracing member 407, from a bottom of that lower bracing member 407. Conversely, the second wall member 405 exits the first node 413*a* at a top of the top bracing member 409 and enters the subsequent node 411, on the lower bracing member 407, from a top of that lower bracing member 407.

In a fourth step, the first and second wall members 403, 405 are then drawn upwards again to the top bracing member 409, to a point approximately directly above their exit from the previous node 411. The wall members 403, 405 are twisted together about the upper bracing member 409 at a new node 413*b*, in an opposite direction to the twisting about the lower bracing member 407. As the wall members traverse from the lower bracing member 407 to the upper bracing member 409, they may overlap with and/or contact themselves.

FIGS. 40 to 43 illustrate a hand-held apparatus 471 for use in manufacturing the fifth embodiment truss 401. The apparatus may also be utilised in the manufacture of other embodiments having two twisted wall members, for example, the trusses 1, 501 of FIGS. 1-5 and 49-53 respectively. The apparatus 471 comprises a body 485, handle 481, retractable latches 479, 483, and first and second filament bobbins 473, 487. The bobbins 473, 487 are rotatably held on opposite sides of the body 485 on a respective shaft 475, 491, and biased into contact with the body 485 with a spring 477, 488. The springs 477, 489 act between a head of the respective shaft 475, 491 and an end of the bobbin 473, 487.

A base of each bobbin 473, 487 comprises a ratchet surface 474, 488. A respective latch 479, 483 extends from the body for engaging the ratchet surface of each bobbin. The latches 479, 483 extend through the body 485 to engage the ratchet surfaces and are configured be selectively retract out of engagement with the ratchet surfaces to allow the bobbins 487 to turn freely, for example by being retracted into the body 485, upon rotating the handle 481 about a longitudinal axis. Filament from each bobbin extends through a respective guide aperture 493 provided at a front of the body of the apparatus.

FIGS. 44A to 48C illustrate a method of using the apparatus 471 to manufacture the fifth embodiment truss 401. In a first step, top and bottom filaments 407, 409 are secured and tensioned in a tension direction T, alongside the apparatus, on either side of a mandrel 495, for forming the first and second bracing members. The mandrel 495 is a dual mandrel formed from two side-by-side cylindrical rods.

With the handle 481 rotated handle to 'free' the bobbins 473, 487, first and second filaments from the bobbins 473, 487 are then free to rotate to pay out filament to form the wall members 403, 405. Once enough filament is paid out the handle 481 is rotated to engage the latches 479, 483 with the bobbin ratchet surfaces to enable tensioning. First, the first and second filaments are twisted in tandem about one of the bracing members (the top bracing member 409 in FIG. 44B) for one and a half loops by rotating the apparatus 471 about an axis that is parallel with the respective bracing member 409. The two filaments are then parted by manipulating the apparatus 471 to cause the filaments to be positioned on opposite sides of the mandrel 495, ready to be linked to the lower bracing member 407. With the apparatus 471 positioned below the tensioned lower bracing member 407, the handle 481 is rotated in an opposite direction to in the first step, twisting the first and second filaments in tandem about the other one of the bracing members (the lower bracing member 407 in FIGS. 47A and 47B) to complete a first 'wind' of the truss 401. Through this fabrication process, the tool 471 generally follows a planetary orbit about the longitudinal axis of the mandrel, with the underside of the apparatus 471 facing the mandrel and keeping the orientation of the filament consistent.

The twisted loops are then pushed along the lower bracing member 407 until they are partly under the previous loops on the upper bracing member 409 and/or abutting the previous wind on the lower bracing member 407 allowing filament to run off the bobbins 473, 487. The bobbins 473, 487 are subsequently locked relative to the apparatus body 485, by engaging the latches 479, 483 with the base 474, 484 of the respective bobbins, and the process repeated. The apparatus 471 is manipulated to separate the filaments over the mandrel 495 before they are again twisted about the upper bracing member 409 to form a second 'wind' of the truss 401. While the filament is paying out, means are provided to prevent a loss of tension in any formed truss structure on the mandrel.

While the process illustrated utilises a hand-held apparatus 471, this process may be automated.

Embodiment 501

FIGS. 49 to 53 show a truss 501 according to a sixth embodiment. The truss 501 is substantially as described above for the fifth embodiment truss 401, but comprises two first wall members 503*a*, 503*b*, and two second wall members 505*a*, 505*b*.

This embodiment may be fabricated in a similar manner to the process describe above but utilising two handheld manufacturing devices. A first apparatus 471 has bobbins holding one first wall member 503*a* and one second wall member 505*a*, and a second apparatus 471 has bobbins holding the other first wall member 503*b* and the other second wall member 505*b*.

The two apparatuses operate simultaneously, twisting wall members about the first and second bracing members 507, 509 simultaneously.

The opposing wall members 503*a* and 505*a*, and 503*b* and 505*b* overlap at a point between the upper and lower reinforcing members 507, 509. This overlap is created during fabrication when the apparatus 471 is transitioned from one reinforcing member to the other 509 to 507.

Embodiment 601

FIGS. 54 to 58 show a truss 601 according to a seventh embodiment. The truss 601 is substantially as described above for the fifth embodiment truss 401, but at each node 611, 613 the truss members 603, 605 are wrapped around the respective wall member 607, 609 for two full loops (as opposed to one and a half loops for embodiment 401). Shading is utilised to visually distinguish the first truss member 603 from the second truss member 605 in some of the Figures.

Each of the first and second truss members 603, 605 alternates from being on a left side of the wall members 607, 609 to being on the right side of the wall members (as opposed to remaining on one side of the wall member 607, 609 for embodiment 401). This may result in a more robust truss structure.

In this embodiment, twisted portions of the truss members 603, 605 cover substantially the whole length of each wall member 607, 609. There is substantially no exposed wall member between adjacent first nodes 611, or adjacent second nodes 613.

This embodiment 601 may be fabricated in a similar manner to the process describe above in relation to 401 but twisting the truss members about the wall members for two full turns at each node.

Device

The truss described above may be used as the structure in bioresorbable devices such as those described in PCT application PCT/NZ2018/050134, which is hereby incorporated in full by way of reference.

Such a device may comprise a flexible bioresorbable sheet that at least partly forms the walls of the channel. In some embodiments, the flexible sheet or sheets may only partly form the channel wall, with the remaining part of the channel wall formed by the tissue surface when the device is in use. That is, the channel may be formed between a surface of a flexible sheet and a surface of tissue or bone at the treatment site. Alternatively, the flexible sheet or sheets may form a major part or substantially the whole of the channel wall. Such an embodiment may either comprise two or more bioresorbable flexible sheets with the truss holding the sheets apart such that one or more channels are defined between facing surfaces of the sheets, or a single flexible bioresorbable sheet may be wrapped around the truss 1 to form the wall of the channel.

To secure the flexible sheet or sheets over or around the truss, the sheet or sheets may be stitched together along a seam at a side of the channel, or otherwise joined. To facilitate fluid flow into the channel, apertures may be provided in the sheet, the distribution, size, and shape of the apertures being selected according to the application and the characteristics of the flexible sheet and truss.

In some embodiments of the invention, the flexible sheet(s) are formed from ECM. The ECM sheets are typically collagen-based biodegradable sheets comprising highly conserved collagens, glycoproteins, proteoglycans and glycosaminoglycans in their natural configuration and natural concentration. ECM can be obtained from various sources, for example, dermis pericardial or intestinal tissue harvested from animals raised for meat production, including pigs, cattle and sheep or other warm-blooded vertebrates.

The ECM tissue suitable for use in the invention comprises naturally associated ECM proteins, glycoproteins and other factors that are found naturally within the ECM depending upon the source of the ECM. One source of ECM tissue is the forestomach tissue of a warm-blooded vertebrate. The ECM suitable for use in the invention may be in the form of sheets of mesh or sponge.

Forestomach tissue is a preferred source of ECM tissue for use in this invention. Suitable forestomach ECM typically comprises the propria-submucosa of the forestomach of a ruminant. In particular embodiments of the invention, the propria-submucosa is from the rumen, the reticulum or the omasum of the forestomach. These tissue scaffolds typically have a contoured luminal surface. In one embodiment, the ECM tissue contains decellularised tissue, including portions of the epithelium, basement membrane or tunica muscularis, and combinations thereof. The tissue may also comprise one or more fibrillar proteins, including but not limited to collagen I, collagen III or elastin, and combinations thereof. These sheets are known to vary in thickness and in definition depending upon the source of vertebrate species.

The method of preparing ECM tissues for use in accordance with this invention is described in U.S. Pat. No. 8,415,159.

In some embodiments of the invention, sheets of polymeric material may be used. The polymeric material may be in the form of sheet or mesh. Synthetic materials such as polyglycolic acid, polylactic acid and poliglecaprone-25 will provide additional strength in the short-term, but will resorb in the long term. Alternatively, the polymeric material may be a natural material, or derived from a natural material, such as a proteins (e.g. collagen), a polysaccharides (e.g. alginate), and a glycoprotein (e.g. fibronectins).

Any desirable bioactive molecules can be incorporated into the ECM or polymeric material or the truss member material itself. Suitable molecules include for example, small molecules, peptides or proteins, or mixtures thereof. The bioactive materials may be endogenous to ECM or maybe materials that are incorporated into the ECM and/or polymeric material during or after the grafts manufacturing process. In some embodiments, two or more distinct bioactive molecules can be non-covalently incorporated into ECM or polymer. Bioactive molecules can be non-covalently incorporated into material either as suspensions, encapsulated particles, micro particles, and/or colloids, or as a mixture thereof. Bioactive molecules can be distributed between the layers of ECM/polymeric material. Bioactive materials can include, but are not limited to, proteins, growth factors, antimicrobials, and anti-inflammatories including doxycycline, tetracyclines, silver, FGF-2, TGF-B, TGF-B2, BMR7, BMP-12, PDGF, IGF, collagen, elastin, fibronectin, and hyaluronan. In some embodiments, the truss members may be coated with one or more drugs or compounds, for example for elution. One example may be the use of a chlorhexidine coating as an antimicrobial agent to prevent biofilm formation.

The fabrication of truss structures without relying on the use of head bonding to join truss members may also advantageously help to preserve the integrity of any antimicrobial coating on the truss filaments. In contrast these coatings may be affected in structures that rely on heat bonding of truss members.

The truss 1 may define a single channel or a plurality of interconnected channels, for example as a branched structure. It will be appreciated that some devices of the invention will comprise many channels for fluid flow, whereas some devices of the invention may comprise only 1 or 2 channels.

The device has a port in fluid communication with the channel or channels of the device, so that fluid that drains into any one of the channels will flow towards and out of the port. The port may be configured for location internally in a patient or for location externally, for example on the exterior surface of the patient's skin or otherwise the exterior of the patient's body close to a surgical opening in the body. The port may merely consist of an opening at the end of the truss or channel, for communication with a conduit from the negative or positive pressure source.

The port may comprise features to enhance the coupling between the conduit and the device. For example, the shape, diameter, and/or the construction of the device truss may alter adjacent to the port. The truss may be coupled to an inlet or outlet conduit by way of an internal or external coupling. The truss may include a length adjacent to the port, having an increased diameter or with modified properties to form a releasable connection with the supply conduit or lumen. The truss pitch may change in this region to ensure the connection has the appropriate mechanical properties, for example, the required increase in strength and rigidity. This change in pitch and change in diameter is preferably occurs gradually across a transition region.

Figures 59, 59I:
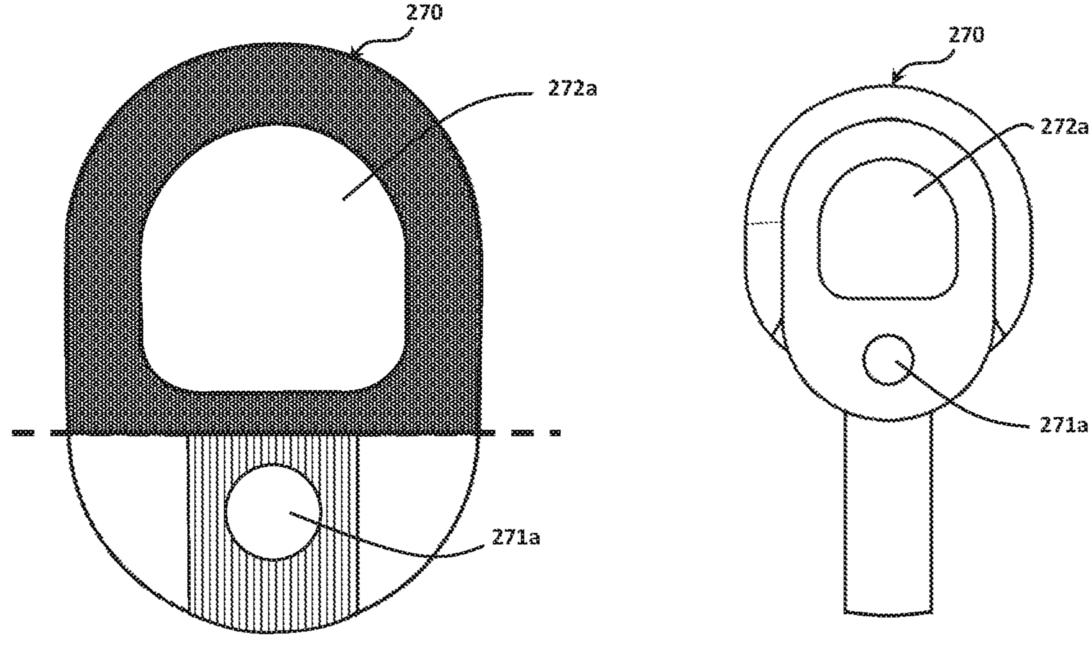
FIGS. 59(*i*) and 59(*ii*) illustrate a multi-lumen conduit that is split to couple to a truss as illustrated in FIGS. 27 to 30, where FIG. 59(*i*) illustrates a cut line for separating the first and second lumens, and FIG. 59(*ii*) is an end view illustrating the dual-lumen conduit of FIGS. 27-30, with the truss hidden.
Figure 60:
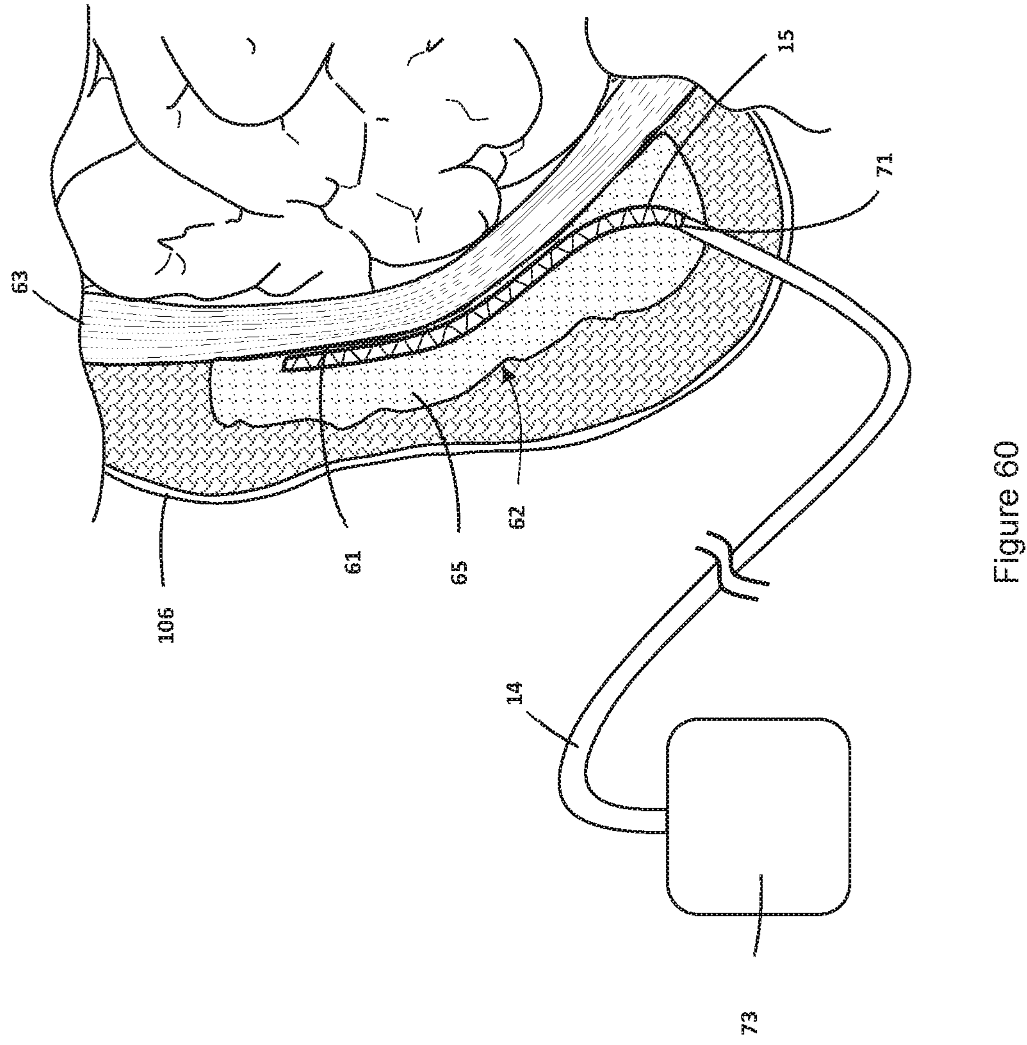
FIG. 60 shows a bioresorbable device having a truss placed within a body of a patient where a dead space exists, with a connected to a source of negative pressure.
Figure 61:
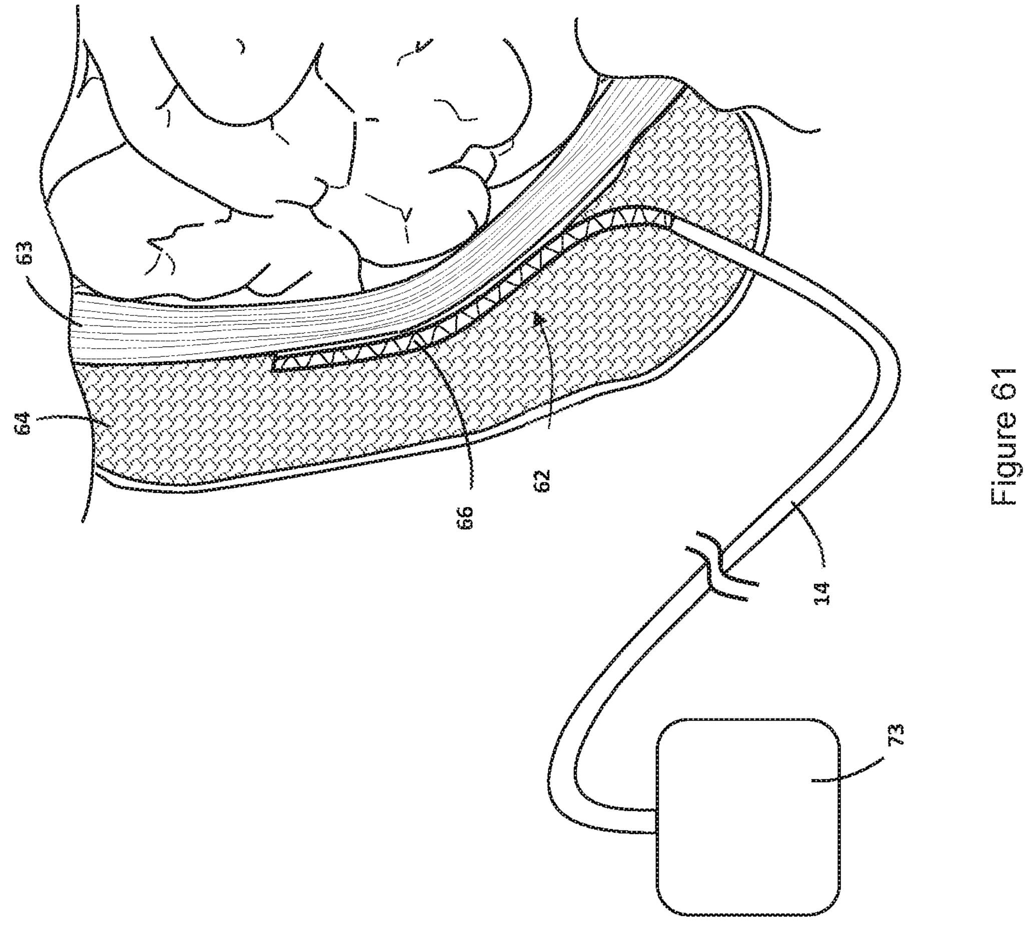
FIG. 61 corresponds to FIG. 60, after the applied negative pressure has successfully closed the dead space at the treatment site.
Figure 63:
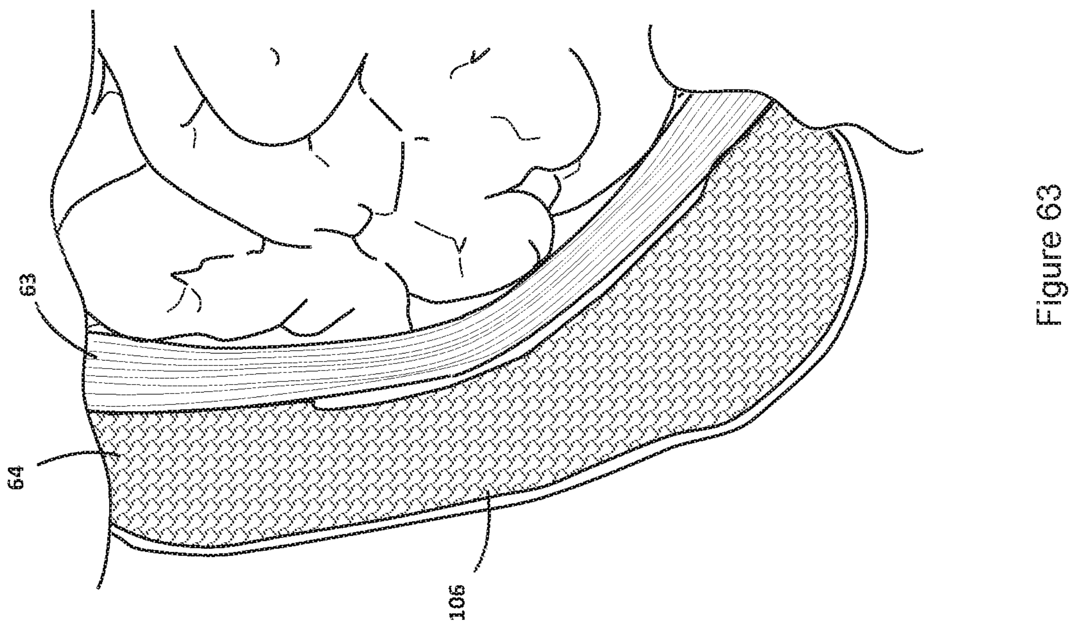
FIG. 63 shows the treatment site of FIGS. 60-62 once the bioresorbable device has resorbed following the successful completion of treatment.
Figure 62:
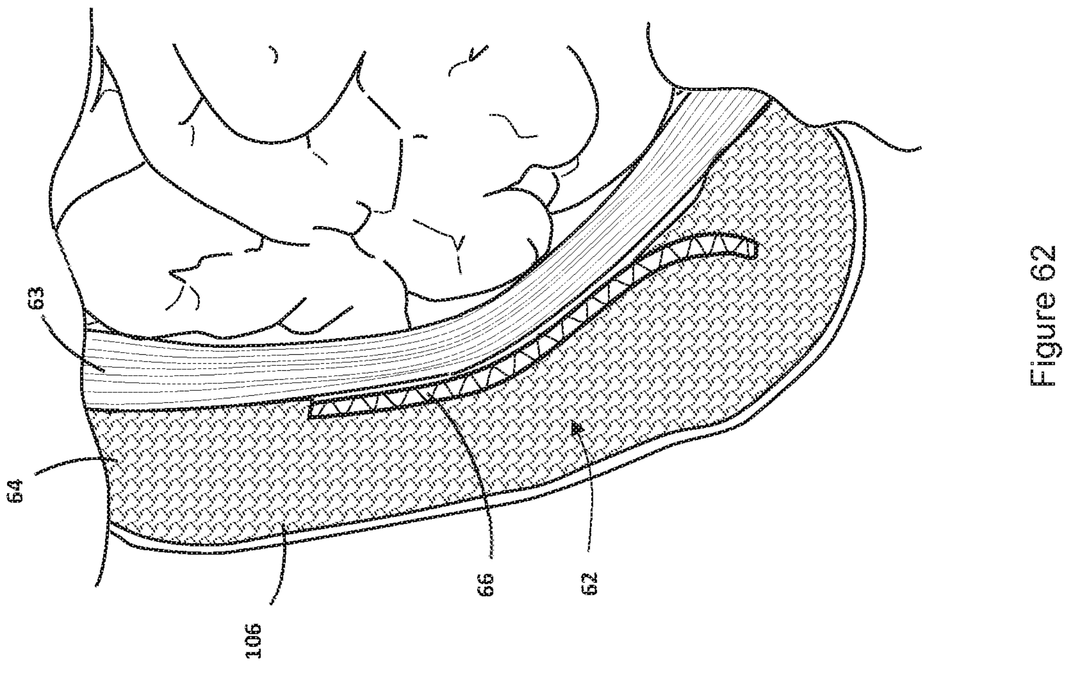
FIG. 62 shows the installed bioresorbable device of FIGS. 60 and 61 once the conduit coupling the device to the source of negative pressure is removed following treatment.

FIGS. 27 to 30 illustrate one method of connecting an exemplary truss 301 with inlet and outlet lumens 271 and 272 of a dual lumen conduit 270 for use in a wound treatment system. In this embodiment, the inlet and outlet conduits are provided by a dual lumen conduit 270, also illustrated in FIGS. 59(*i*) and 59(*ii*), having a major lumen and a minor lumen. The dual lumen conduit splits along a length of the conduit 270 adjacent the coupling with the truss, into a supply conduit 271 having the smaller, minor lumen and an outlet conduit 272 containing the larger major lumen.

Figure 27:
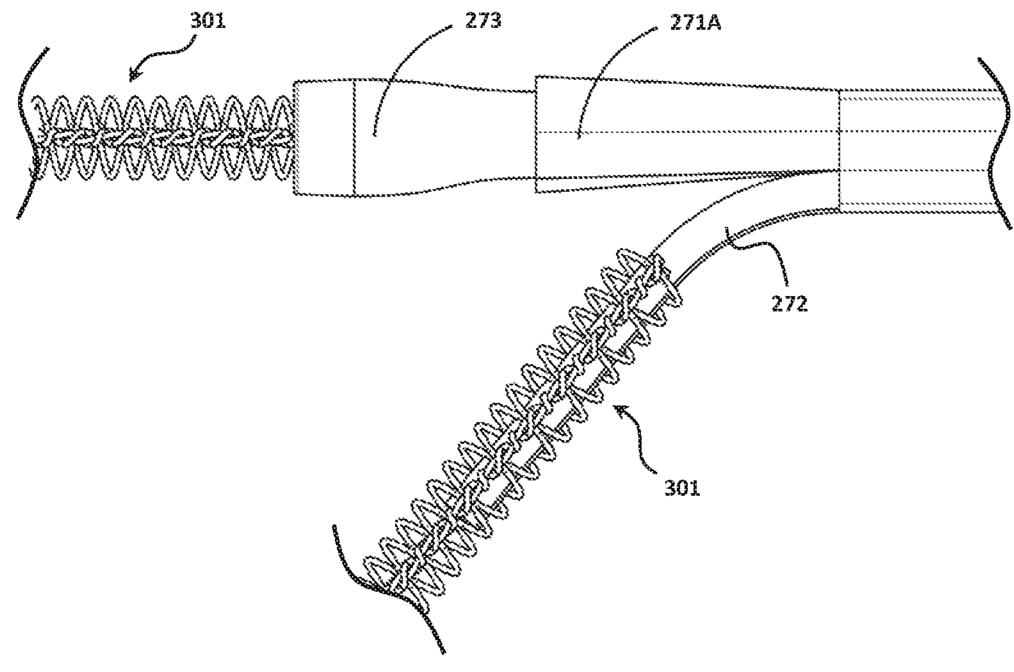
FIG. 27 is a plan view illustrating connection of an exemplary truss with inlet and outlet conduits for use in a wound treatment system.
Figure 28:
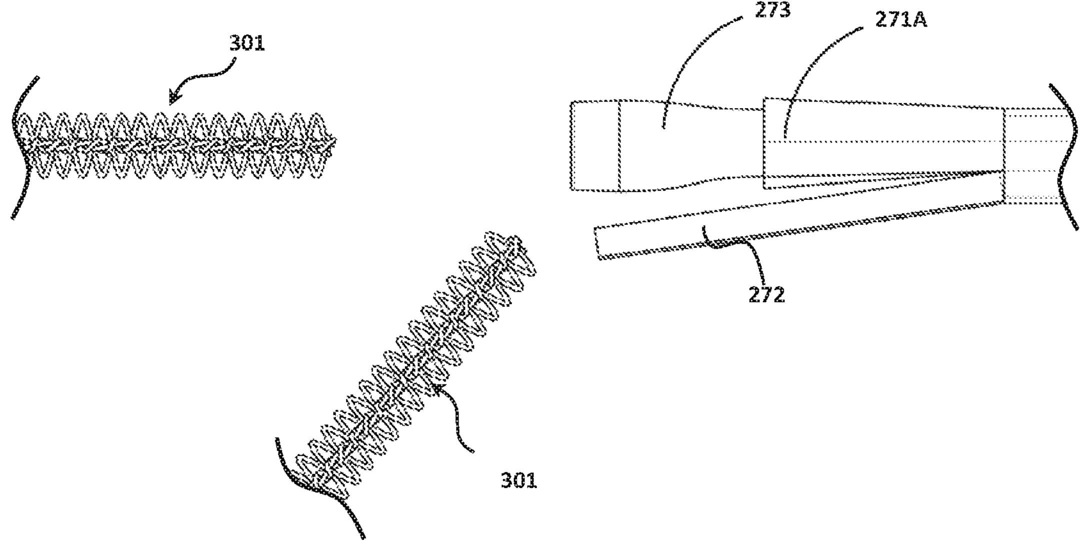
FIG. 28 is a view corresponding to FIG. 27 but showing the truss disconnected from the conduits.
Figure 29:
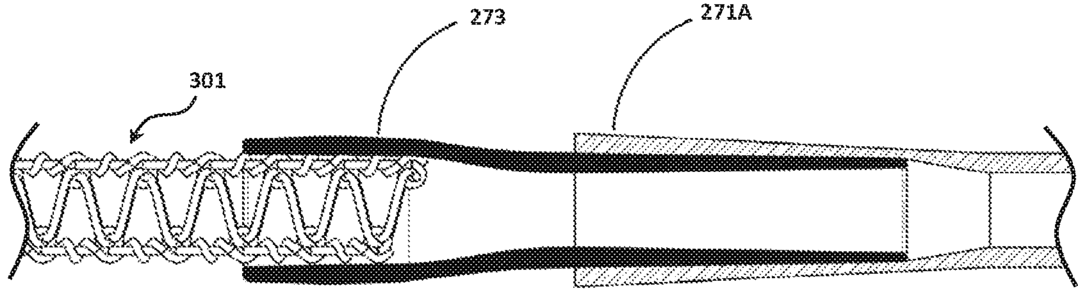
FIG. 29 is a side view illustrating one method for coupling an exemplary truss to a conduit, with the conduit and coupling sleeve shown in section view for clarity.
Figure 30:
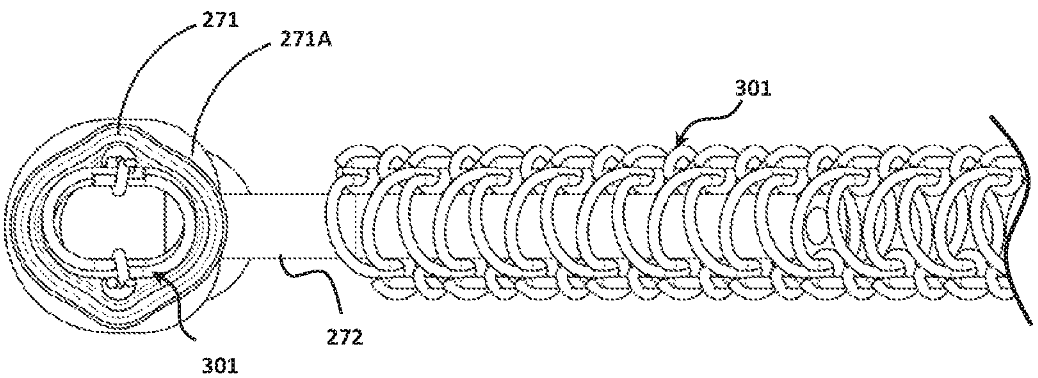
FIG. 30 is a side view of the truss and conduit connection of FIG. 27.
Figure 31:
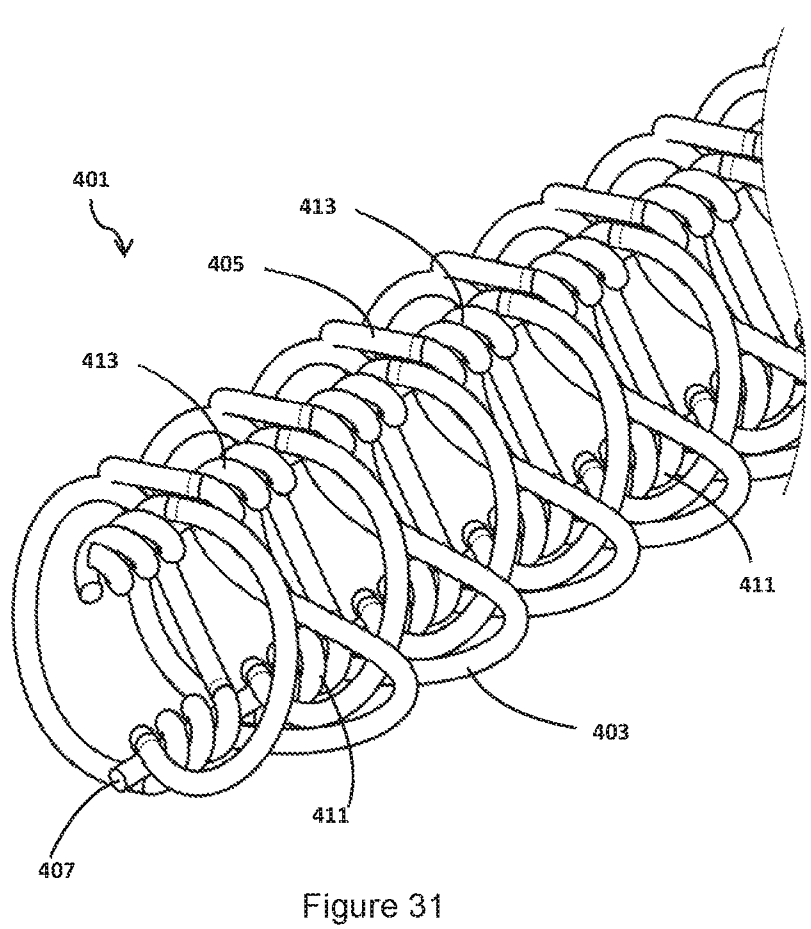
FIG. 31 is a left side perspective view of a fifth embodiment truss structure having an indeterminate length.
Figure 32:
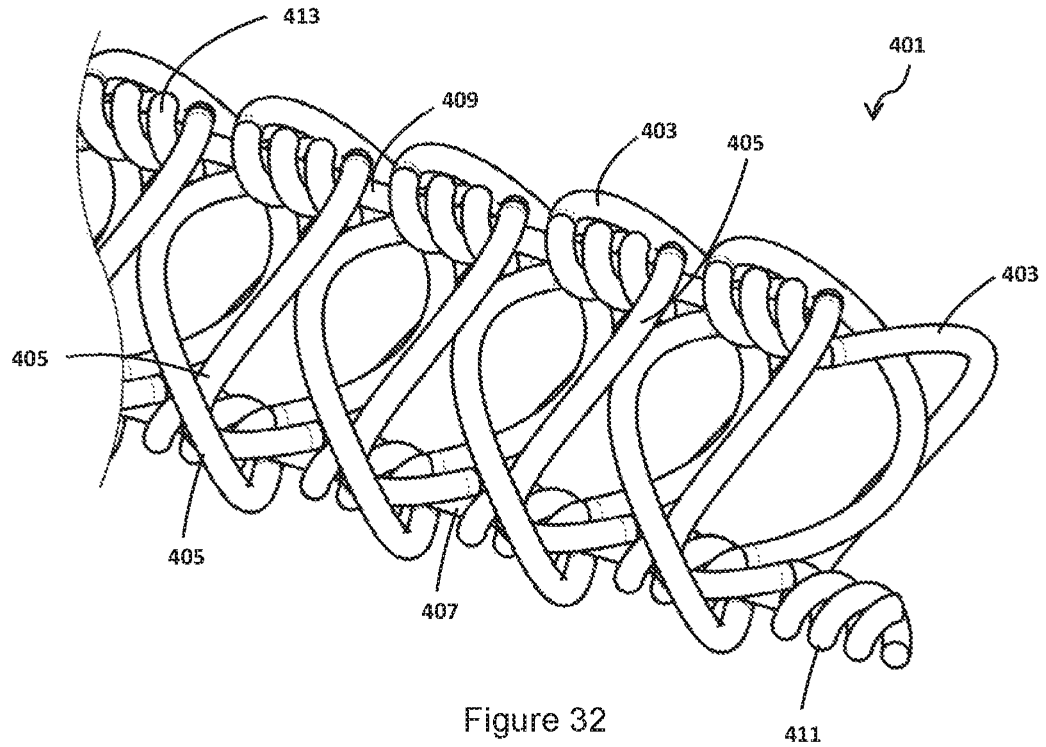
FIG. 32 is a right side perspective view of the embodiment of FIG. 31.

The supply conduit 271 is coupled to a first end of the truss 301 by inserting the supply conduit 271 into the truss 301, as illustrated in FIGS. 27 and 30. The outlet conduit 272 is coupled to the other end of the truss 301 with a connector 273. The connector 273 is a moulded component that forms an internal push-fit connection with the outlet conduit 272 and slides over the outside of the truss 301, as illustrated in FIG. 29. The connector 273 comprises a tapered outer surface for engagement with the inner surface of the conduit 272 to ensure a secure fit between the two components. A secure fit is important to ensure the connector 273 is removed along with the conduit 270/272 once treatment is concluded.

The inlet and outlet ports of the truss 301 are spaced apart to ensure fluids supplied by the supply lumen 271 lumen do not flow directly between lumens to the outlet lumen 272 and instead are supplied to the wound.

It will be appreciated that other methods of coupling the device to the supply conduit are appreciated and envisaged, including additional retention features. For example, an exterior surface of the conduit may be threaded or have protrusions/detents for additional engagement with the truss to prevent unintended disconnection; or a connector for coupling a conduit to a truss may comprise a detent, barb, thread or other feature to engage with the truss and/or with a conduit. In one embodiment, interfacing barbed features may be provided on the tapered section of the connector 273 to increase the force required to separate the connector from the truss and/or the removal conduit 272.

The device described herein may advantageously be customised to adjust the duration for which the device is functional in-situ for any given application. For example, by adjusting channel size, wall thicknesses, or the thickness or density of truss members, or the number and type of bracing members.

System and Method for Use

FIGS. 60 to 63 illustrate the placement and use of a bioresorbable device 61 comprising the above-described truss 1, implanted at a treatment site 62 in the body of a patient, for the purpose of draining fluid from the treatment site or delivering fluid to the treatment site. The treatment site 62 may be a space between surfaces of muscle tissue 63, adipose tissue 64 or skin tissue that have been separated during surgery or as a result of trauma. The treatment site may be a dead space 65 resulting from a seroma or hematoma that has been resected away, or maybe used as a prophylactic following surgical excision of tissue. Alternatively, the treatment site may be an open wound such as following trauma, injury or surgical excision of necrotic or infected tissue, with an occlusive drape or cover placed over the wound to create a sealed environment. Although the system is illustrated with the first embodiment truss 1, any embodiment truss 1, 101, 201, 301 described above may be substituted.

The bioresorbable device 61 is used as part of a system for draining fluid from the treatment site 62 or delivering fluid to a treatment site. The bioresorbable resilient truss 1 of the device holds the two tissue surfaces 63, 64 spaced apart, thereby defining a channel 66 into which fluid from the treatment site can drain or from which fluid can be delivered to the treatment site. The two tissue surfaces 63, 64 need to be held apart because they would otherwise collapse together, particularly under application of negative or reduced pressure (vacuum) to assist with fluid drainage.

A port 71 in the form or an opening at one end of the truss 1 is in fluid communication with the channel 15 and allows for connection of the channel with a source of negative pressure or positive pressure 73 and provides fluid communication between the treatment site 62 and the port 71 of the device 61. A conduit 14 is releasably coupled to either the port 71 of the device 61 or to a fluid impermeable dressing such that it's in fluid communication with the device 61. In the use of the device illustrated, the port 71 is located within the body, with the inlet and outlet conduits passing through the skin. This arrangement is desirable as the body will create a seal around the coupling of the conduit to the port.

In alternative embodiments, the port 71 may be coupled to an impermeable dressing located on the exterior surface of the patient's skin 106 which provides an airtight hermetic seal around the incision of the skin and an alternative means to which a conduit is releasably coupled to the dressing.

A reservoir (described further below) is located external to the body of the patient, and arranged in fluid communication with the conduit for receiving fluid from the conduit or for holding a treatment fluid for delivering fluid to the conduit 14. The source of pressure 73 may be capable of delivering negative pressure to the device 61 so that fluid is drained from the treatment site 62 into the device 61 and transferred through the conduit 14 to the reservoir, or may be capable of delivering positive pressure to the device so that fluid in the reservoir is transferred through the conduit into the device and to the treatment site. In preferred embodiments, treatment fluid is delivered to the wound by applying vacuum pressure downstream of device simultaneously while fluid is supplied to the device from an ambient pressure upstream source.

The source of pressure 73 will typically be a vacuum pump for applying negative pressure to drain fluid from the treatment site and/or draw treatment fluid from the site, alternatively the source of pressure may be a pump for pumping fluid from the reservoir into the device 61 for delivery to the treatment site. The pump may be manually operated, for example using a squeeze bulb, or may be electronically controlled for more precise delivery of fluid to the site.

FIGS. 64 to 68 show exemplary embodiments of negative pressure treatment systems 2100, 2200, 2300 (herein treatment systems) for the removal of fluid from a wound treatment site 62 or for supplying treatment fluid to and removing fluid from a wound treatment site 62 using a wound treatment device 61. The wound treatment device 61 of the system may be any one of the devices described herein.

In relation to the exemplary embodiment systems 2100, 2200, 2300, like reference numbers are used for different embodiments to indicate like features.

Figure 64:
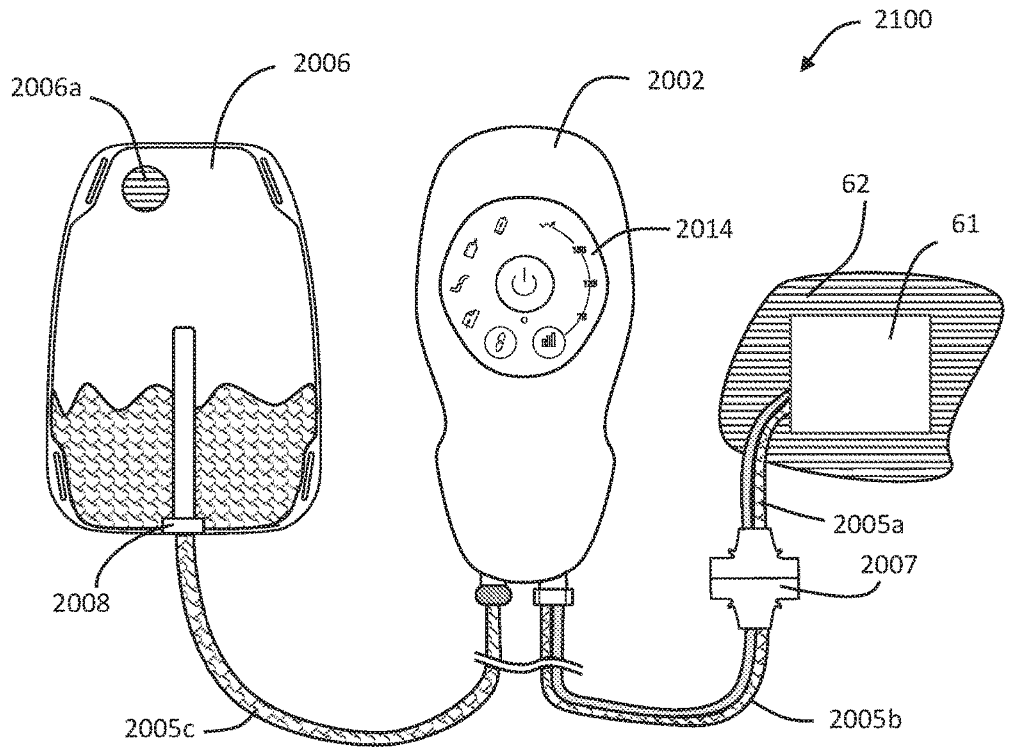
FIG. 64 provides a high-level schematic representation of a negative pressure treatment (NPT) system according to at least one embodiment described herein.
Figure 65:
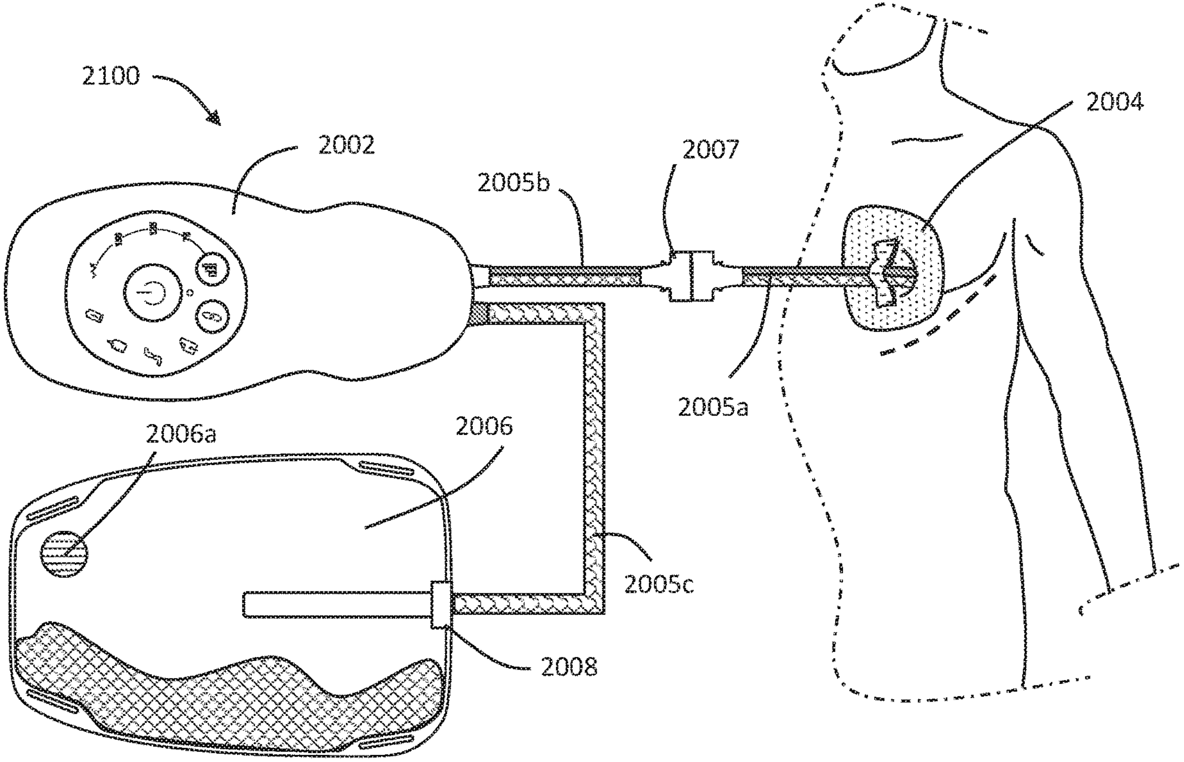
FIG. 65 illustrates the system of FIG. 60 applied to an internal wound.

Referring to FIG. 64, at a general level the treatment system 2100 comprises a wound treatment device 61 to be located at a wound treatment site 62 ('wound'), a vacuum pressure unit 2002 comprising a vacuum pump assembly for applying negative pressure to the wound 62 via the treatment device 61, and a fluid collection reservoir 2006 for collecting fluid returned from the wound 62. FIG. 65 illustrates an internal wound site located at a chest area of a patient; however, the system may be used to treat internal wounds located at other sites for example to treat an abdominal wound.

The vacuum pressure unit (or vacuum unit) 2002 is configured to position the pump assembly 2015 upstream of the fluid collection reservoir 2006 and downstream of the wound treatment device 61. The wound treatment device 61 may comprise a topically applied wound dressing, an implanted treatment device or a combination of both in a coupled configuration. The fluid collection reservoir 2006 is configured to include one or more air permeable filters or vents **2006*a* to maintain the fluid collection reservoir 2006 and connected conduit 2005*c*** at an ambient pressure level.

The vacuum unit 2002 fluidly couples to the wound treatment device 61 via at least one conduit. The conduit from the vacuum unit 2002 to the wound treatment device 61 may comprise a two-part conduit, with a first conduit **2005*b* extending from the vacuum unit 2002, and a second conduit 2005*a* extending from the wound treatment device 61. The second conduit may be part of the wound treatment device 61 or may be connected to the treatment device 61 by a connector (not shown). A connector 2007 is provided to fluidly couple the first and second conduits 2005*a*, 2005*b*. Alternatively, a continuous conduit may extend between the vacuum unit 2002 and the treatment device 61**.

The connector 2007 may comprise a one-way valve oriented to allow fluid flow in a direction from the wound 62 towards the vacuum unit 2002 and prevent a backflow of fluid from the pump to the wound. In alternative embodiments, a one-way valve may instead be provided within the vacuum unit 2002, elsewhere on the conduit **2005*a*, 2005*b*, or as part of the treatment device 61. In a further alternative, the treatment system 2100 may be without a one-way valve between the treatment device 61** and the vacuum unit.

In some embodiments, the conduit(s) between the vacuum unit 2002 and the treatment device 61 may comprise a dual lumen conduit with a primary lumen for the passage of fluid flowing from the wound to the pump assembly 2015, and a secondary lumen. The secondary lumen may allow for measurement of pressure at the wound site. The secondary lumen provides for the delivery of air and/or treatment fluids to the wound 62. However, in alternative embodiments multiple conduit(s) may be provided between the vacuum unit 2002 and the treatment device 61 each with a single lumen.

A further conduit 2005*c* is provided between the vacuum unit 2002 and the reservoir 2006 to fluidly couple the pump assembly 2015 to the reservoir 2006. A connector 2008 may be provided to fluidly couple the conduit 2005*c* to the reservoir 2006.

In preferred embodiments, the vacuum unit 2002 is a portable hand-held unit. The vacuum unit 2002 may be a single use unit that is intended to be used for a single patient. In an alternative embodiment the vacuum unit 2002 could be configured for multi-patient use. The vacuum unit 2002 comprises a (plastic) shell or enclosure to house the pump assembly 2015 and other components. The vacuum unit 2002 comprises a user interface 2014 for operating the vacuum unit 2002. The user interface may include controls to turn the pump assembly 2015 of the system 2100 on and off, and may allow an operator to control parameters of a pressure treatment being applied to the wound 62 such as the level of vacuum pressure being applied or the length, size and frequency of pressure oscillations between upper and lower set points.

In alternative embodiments the user interface 2014 may also include controls to remotely connect a monitoring device to the vacuum unit to enable the transmission of data to an operator or user of the system to aid in the monitoring of treatment.

Figure 66:
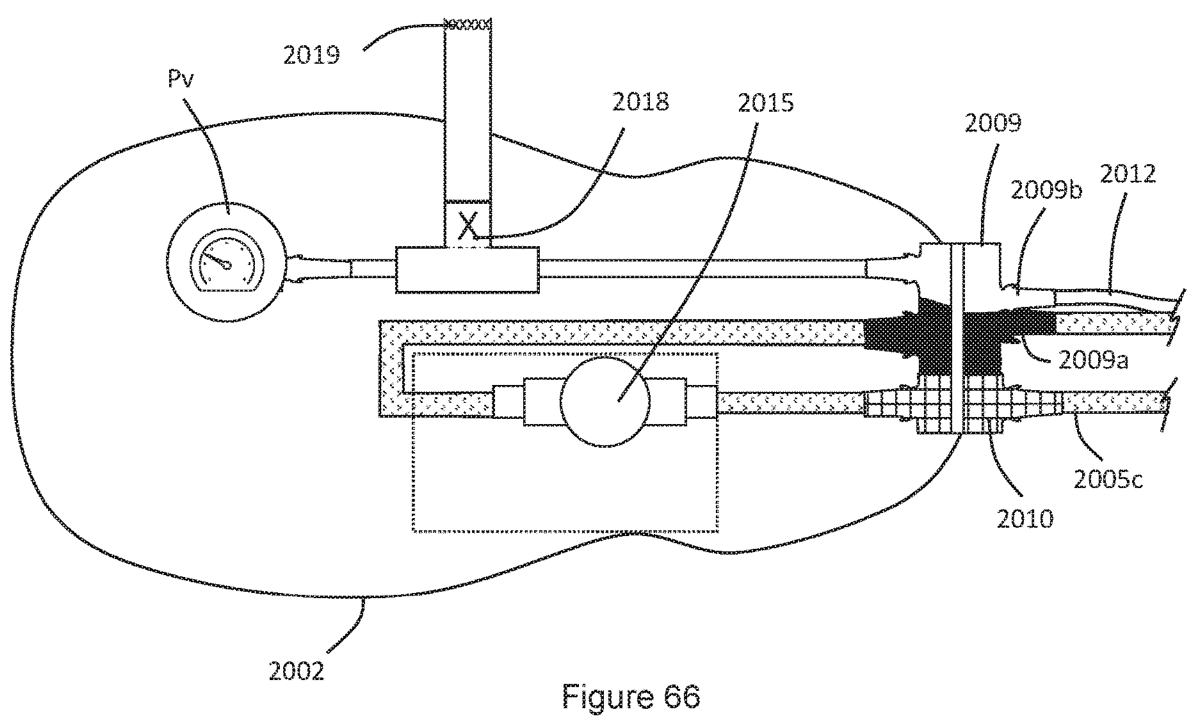
FIG. 66 is a schematic representation of a vacuum unit of the system of FIG. 60.

Referring now to FIG. 66 together with FIG. 64, the vacuum unit 2002 comprises a housing or enclosure that houses a vacuum pump assembly 2015 described in more detail below, batteries or other power supply, a vacuum unit connector 2009 in fluid communication with the conduit(s) 2005*b*, 2005*a* to deliver and receive fluid from the wound treatment site 62, and a vacuum unit outlet connector 2010 in fluid communication with the conduit 2005*c* to the reservoir 2006, for the fluid flow from the pump assembly 2015 to the reservoir 2006. The connectors 2009, 2010 are configured to couple with ends of respective conduits 2005*b*, 5*c* and may be of any suitable form, for example, they may comprise luer-type connectors.

In one embodiment the vacuum unit connector 2009 may comprise two one-way valves such that a one-way valve within the secondary connector 2009*b* is oriented to allow the flow of fluids from an upstream source, such as ambient air that has been passed through a sterile filter (filter 2019 in FIGS. 68 and 69) or from a treatment fluid reservoir (reservoir 2026 in FIGS. 68 and 69), to the wound 62. The corresponding one-way valve within the primary connector 2009*a* is oriented to allow the flow of fluid in a direction from the wound 62 towards the vacuum unit 2002. In some embodiments the one-way valves within the primary 2009*a* and secondary 2009*b* connector may be configured to be closed when the vacuum unit connector 2009 is disconnected from the vacuum unit 2002. These valves are then subsequently opened to allow the passage of fluids when the vacuum unit connected 2009 re-connected to the vacuum unit 2002. Examples of known prior art connectors that possess such features include needle-free or needless connectors for use within IV applications, such as the BD® MaxPlus™ needle-free connectors, which only allow a passage of fluid once engaged with an appropriate luer-lock connector.

The conduit 2005*b* for fluid flow into and out of the vacuum unit connector 2009 is a dual lumen conduit with a primary lumen 2011 and a secondary lumen 2012. The connector 2009 includes a primary connector 2009*a* providing a fluid inlet to connect to the primary lumen 2011, and a secondary connector 2009*b* providing a fluid outlet to connect to the secondary lumen 2012 while keeping the flow from these lumens separated. The larger primary lumen 2011 allows the passage of fluid flowing from the wound, through the primary connector, to the vacuum pump assembly 2015. The secondary or supply connector 2009*b* may be separate from the primary or removal connector 2009*a*.

The primary and secondary lumens 2011, 2012 are preferably provided as adjacent passages in a single body/conduit along most of their length. However, adjacent the vacuum unit 2002 and/or adjacent the wound treatment device 61, the dual lumen conduit 2005*a*, 2005*b* may be split or separated into two separate limbs or conduits, a supply conduit comprising the secondary lumen 2012 and a removal or exudate conduit comprising the primary lumen 2011, for ease of coupling to the vacuum unit 2002 and/or to allow the supply conduit to enter the wound or wound treatment device 61 at a different location to the removal conduit. The primary or removal conduit and lumen may be referred to interchangeably and referenced by reference numeral 2011 and the secondary or supply conduit and lumen may be referred to interchangeably and referenced by reference numeral 2012.

The supply conduit 2012 is in fluid communication with a pressure sensor Pv to allow for measurement of pressure on an upstream side of the wound treatment device 61.

The vacuum unit 2002 comprises an air inlet valve 2018 in fluid communication with the supply conduit 2012. The air inlet valve 18 is controlled in a manner to introduce air into the treatment system 2100 to assist with lifting fluid from the wound site 62, as described in more detail below.

As shown in FIG. 66, the air inlet valve 2018 may have an inlet to draw ambient air to the system from outside the vacuum unit 2002 enclosure. Alternatively, the inlet for the air inlet valve may take air from inside the vacuum unit housing/enclosure.

A sterile filter 2019 is provided to prevent the ingress of bioburden and non-sterile air into the system 2100 and wound site 62. In FIG. 66, the filter 2019 is provided on an inlet of the air inlet valve 2018, however a filter may be placed at another location between the air inlet valve 2018 and the vacuum unit fluid supply connector 2009*b*, or between the air inlet valve 2018 and the wound site 62.

Figure 67:
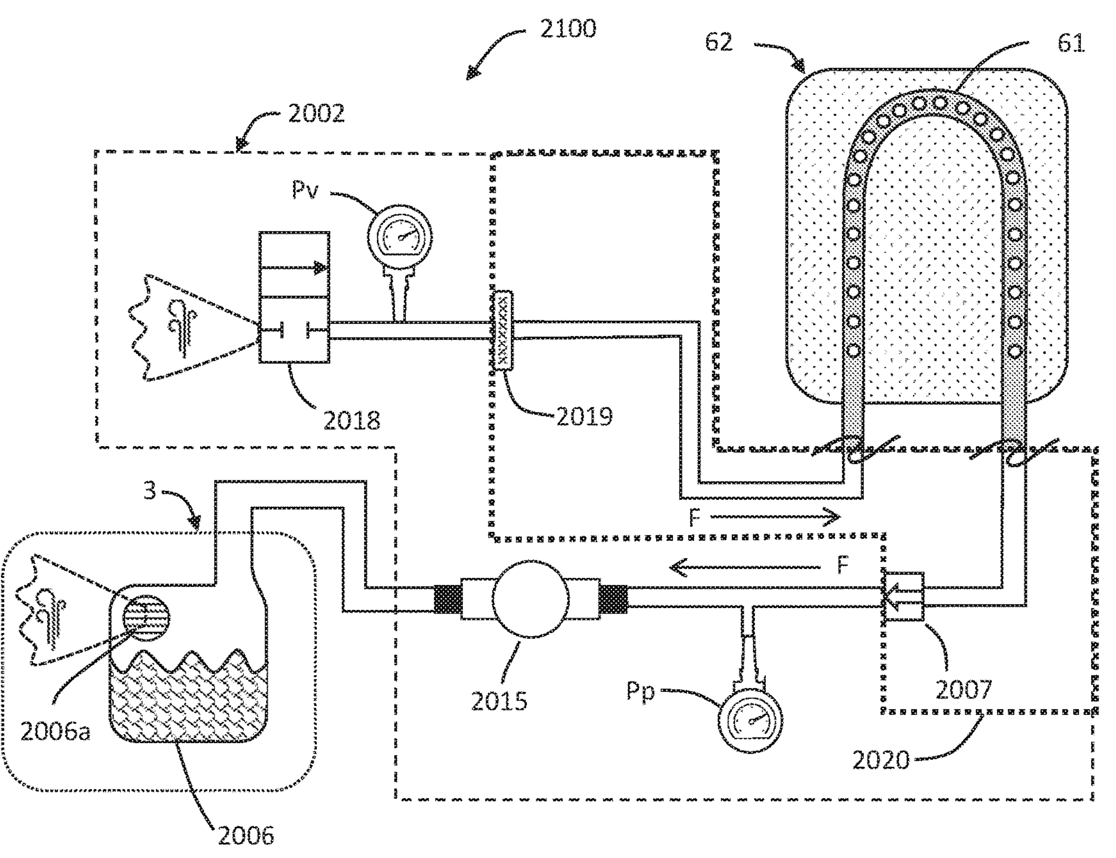
FIG. 67 is a schematic representation of the system of FIG. 64.

FIG. 67 illustrates the treatment system 2100 schematically in more detail. The boundary or outer enclosure of the vacuum unit 2002 is illustrated by the dashed line in FIG. 67. On an upstream side of the treatment device 61 the vacuum unit 2002 comprises the air inlet valve 2018, optionally the pressure sensor Pv and the sterile filter 2019, and on a downstream side of the treatment device 61 the vacuum unit 2002 comprises the pump assembly 2015 and optionally a pressure sensor Pp between the pump assembly 2015 and treatment device 61. The vacuum unit 2002 may also comprise a connection manifold 2020 providing a connection interface between the conduit 2005*a*, 2005*b* to the treatment device 61 and the vacuum unit 2002. The connection manifold 2020 is illustrated by the dotted line in FIG. 67 and replaces connector 2009 shown in FIG. 66.

Figure 69:
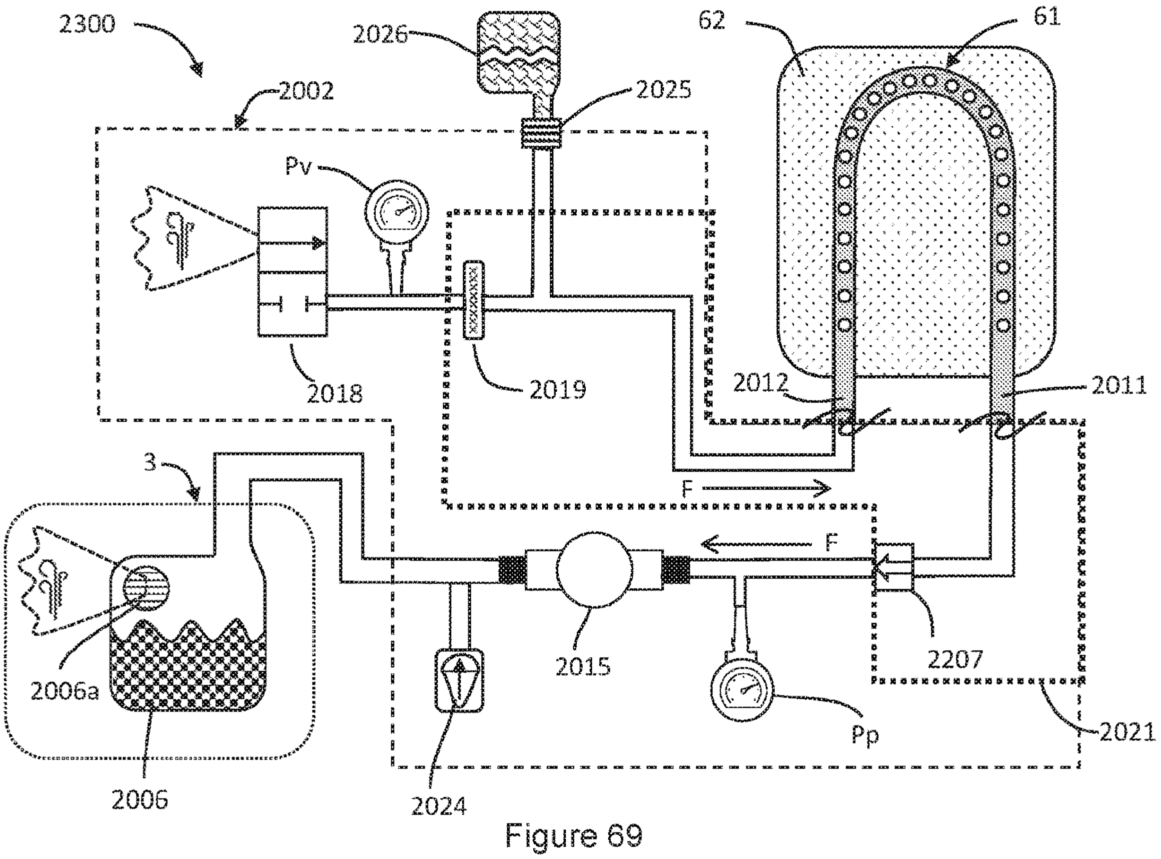
FIG. 69 is a schematic representation of a further alternative embodiment of a negative pressure treatment (NPT) system.

In the embodiment system 2300 of FIG. 69 the vacuum unit 2002 additionally includes a colour sensor 2024 that is electronically connected to the vacuum unit controller 2017. In this embodiment 2300, the colour sensor 2024 is positioned along the fluid flow path positioned between the outlet of the pump 2015 and the outlet connector 2010.

However, the colour sensor could alternatively be positioned along the fluid pathway in any suitable position upstream of the inlet of the pump 2015.

The colour sensor 2024 may be beneficial to detect a colour change of wound exudate fluid flowing through the system from the treatment device 2003 at the wound site 2004. For example, a natural change in colour from a first blood rich wound exudate immediately following surgery, to a pink colour of serosanguinous drainage (blood and serum), and/or to a clear serous (serum only) drainage. This operation of the colour sensor 2024 may be enhanced by the supply of filtered air from upstream of the treatment device 2003. The filtered air displaces the fluid for a short to time frame to produce a readable sample of fluid within that short time frame, similar to that of a direct aspiration of fluid from the treatment site 2004 via a needle.

The inclusion of a colour sensor within various embodiment systems that supply treatment fluid to, and remove treatment fluid from, the wound may offer further benefits. For example, the colour sensor 2024 could be configured to detect the passage of treatment fluid being supplied from the treatment fluid reservoir 2026 and passing through the upstream fluid pathway, removal conduit 2011, wound treatment device 3 and supply conduit 2012, to the vacuum unit 2002 denoting the complete saturation of treatment fluid through the connected system. In other embodiments the treatment fluid could be combined with a colour based indicator for the detection of changes at the wound in response to the presence of infection, biofilm or other wound based pathologies.

Figure 68:
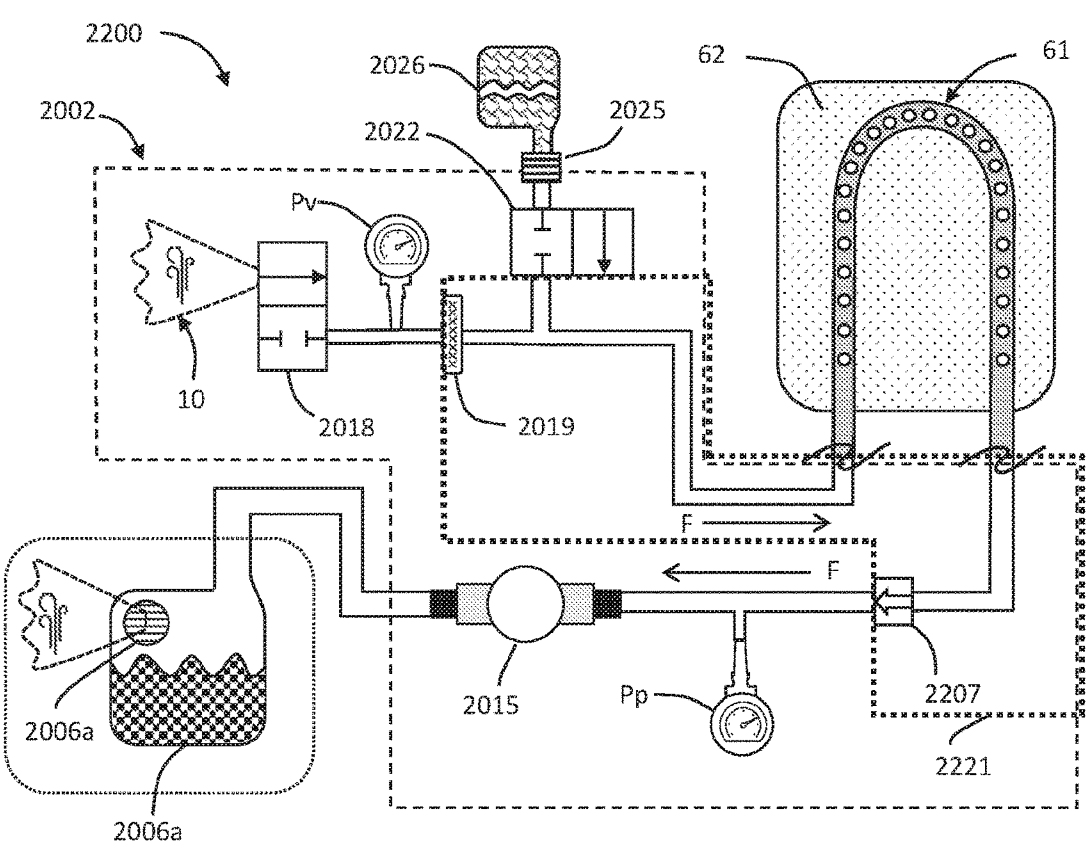
FIG. 68 is a schematic representation of the system of a further embodiment negative pressure treatment (NPT) system.

FIGS. 68 and 69 illustrate further embodiment treatment systems 2200, 2300 for supplying fluid to and removing fluid from a wound. The embodiments of FIGS. 68 and 69 include the same or similar features of the system 2100 described above with reference to FIGS. 64 to 67, however are additionally configured to provide a treatment fluid to the wound treatment device 61.

With reference to FIGS. 68 and 69, the vacuum unit 2002 may comprise one or more ports 2025 to receive therapeutic fluids for delivery to the wound site. The port 2025 is preferably configured to be nominally closed to the passage of liquids when disconnected from the treatment fluid reservoir 2026 which subsequently opens when engaged with a luer connector. The B. Braun Medical® CARESITE™ needless connector provides an example of such a port.

A therapeutic agent in the form of a treatment fluid may be selectively delivered to the wound treatment device 61 via the supply conduit 2012. A fluid source or treatment fluid reservoir 2026 may be coupled to the fluid port 2025 of the vacuum unit 2002, for example via a conduit or connection to an intravenous (IV) fluid giving set such as a Baxter® EMC 9608 Admin Set, B. Braun Medical® Single Chamber IV Infusion Set or similar sterile IV infusion therapy set. The treatment fluid reservoir is preferably at atmospheric pressure whilst connected to the treatment system. This can be achieved by using a non-vented IV infusion therapy set in combination with a flexible fluid bag such as Baxter® Sodium Lactate (Hartmanns or compound sodium lactate) IV Bag or similar, or it may also be achieved by connecting a vented IV infusion therapy set to a rigid or semi-rigid container of treatment fluid, such as Prontosan® Wound Irrigation Solution by B. Braun Medical®.

Example therapeutic fluids include, but are not limited to, compound sodium lactate, physiological saline (0.9% NaCL—Sodium Chloride) and 0.45% normal saline (0.45NaCL). Antimicrobial agents and solutions could also be applied for the treatment of infections and may contain agents such as polyhexanide (PHMB), silver nitrate, hypochlorous acid (HOCI), sodium hypochloride, betaine, sodium hypochlorite, super-oxidized water with neutral pH or any other antimicrobial wound irrigation solutions.

Other treatment fluids may also include cell-suspensions and cell-based fluids for promoting wound healing. The fluid to be delivered may contain one or more nutrients, ‘flowable fluids’ such as Thixotropic gels or highly viscous fluids that can still be transported via a conduit, cell-suspensions therapeutic agents for promoting wound healing. The fluid may comprise flowable gels derived from ECM, hyaluronic acid, growth factors to aid healing, to antimicrobial drugs for the treatment of infection, analgesic drugs such as fentanyl or morphine for pain relief and anti-inflammatory drugs such as ketorolac or diclofenac, for example, although other fluids are envisaged and will be apparent to a skilled person.

Instillation of autologous or allogenic cell-based therapies containing either platelet rich plasma, stem cells, stromal cells, keratinocytes, lymphocytes, bone marrow aspirate, serum and dendritic cells could aid in the repair and healing of wounds. The instillation of chemotherapeutic drugs could also aid in the localised treatment of cancerous cells that may not be operable, or could be used as an overall treatment plan following excision of cancerous tissue.

With reference to the embodiment 2200 of FIG. 68, a treatment fluid inlet valve 2022 is selectively operable to allow fluid to flow from the treatment fluid reservoir 2026 and into the supply conduit 2012 leading to the wound. The reservoir of fluid is at atmospheric pressure. When the treatment fluid inlet valve 2022 is selectively opened, negative pressure from the pump assembly 2015 applied to the wound 62 via the removal conduit 2011 acts to draw fluid from the treatment fluid reservoir 2026 towards the dressing or wound treatment device 61. Upon activation of the treatment fluid inlet valve 2022 the controller (not shown in this figure) within the vacuum unit 2002 detects a subsequent drop in the vacuum pressure level at the Pv and/or Pp pressure sensor(s) and activates the pump assembly 2015 to maintain the vacuum pressure at a target level of vacuum pressure. A control algorithm is described in more detail below. In the illustrated embodiment, the air inlet valve 2018 and sterile filter 2019 is provided upstream of the therapeutic fluid valve 2022.

In the embodiment 2300 of FIG. 69, the system is without a treatment fluid inlet valve 2022. The system 2300 may include an orifice or other flow restriction to control an amount of treatment fluid introduced to the system during negative pressure treatment. In one embodiment the administration of treatment fluids is controlled via the use of an intravenous (IV) fluid giving set such as a Baxter® EMC 9608 Admin Set, B. Braun Medical® Single Chamber IV Infusion Set or similar sterile IV infusion therapy set which is connected to the unit 2002 via the fluid port 2025. The fluid flow rate of treatment fluid being introduced to the supply conduit 2012 is controlled via a roller clamp in the set, which is adjusted to vary the flow restriction within the section of tube that interfaces with the roller clamp component. In this embodiment the rate of fluid instillation can be visually checked via the drip chamber of the IV infusion set when the chamber is orientated upright, with any further flow adjustments made via the roller clamp adjustment. This embodiment provides a manual means to introduce a treatment fluid to the wound 62 via the wound treatment device 61.

In an alternative embodiment the vacuum unit 2002 may be connected to an infusion pump via the fluid port 2025 to allow fluids to be supplied to the wound treatment device 61 in a selectable and controllable manner. Such infusion pump systems could include the B. Braun Medical® Vista® basic large volume infusion pump or the BD® Alaris® Syringe Module for example, which can controllably deliver from 0.1 ml/hour to 1200 ml/hour of treatment fluid on either an intermittent or constant fluid delivery basis. These systems typically offer the means to select the amount, flow rate and frequency of which treatment fluid is dispensed. When treatment fluid is introduced into the vacuum unit 2 the system detects the subsequent drop in the set vacuum pressure level at the Pv and/or Pp pressure sensor(s) and activates the pump assembly 2015 to maintain the systems target level of vacuum pressure. A control algorithm is described in more detail below.

In the embodiments of FIGS. 68 and 69, the vacuum unit 2 comprises a connection manifold 2021 providing a connection interface between the conduit 2005*a*, 2005*b* to the treatment device 61 and the vacuum unit 2002 and between the vacuum unit 2002 and the treatment fluid reservoir 2026 via the fluid port 2025. The connection manifold 21 is illustrated by the dotted line in FIGS. 68 and 69 and replaces connector 2009 shown in FIG. 66. The manifold is described in more detail below.

As described, the treatment system 2100, 2200, 2300 comprises a reservoir 2006 for collecting liquids removed from the wound site 62, for example, wound exudate. In a preferred embodiment, the reservoir 2006 is positioned at the furthermost position away from the wound and therefore is downstream of the pump assembly 2015, for collecting fluids removed from the wound after they have passed through the pump assembly 2015. In the embodiments shown, the reservoir 2006 comprises a flexible bag. Alternatively, a rigid reservoir could be provided.

The reservoir 2006 comprises one or more air permeable filters or vents 2006*a* provided in a wall of the reservoir, for example a hydrophobic venting membrane provided over an aperture in the impermeable membrane. The air-permeable filter(s) or vents(s) allow the venting of gases and thereby prevent pressure build-up in the reservoir preventing effective pumping. An example reservoir has eight vents 2006*a* each having an 8 mm diameter and a pore size of 3 micron to sustain a high level of airflow passing through the system.

Blood clots, fibrin and other solidified fluids or tissue debris may block the venting membranes which causes the bag to inflate with air introduced to the fluid path. This inflation can cause the bag to pop and leak fluid or can prohibit the pump from generating vacuum pressure required by forcing the outlet valves from opening under excess positive pressure.

To avoid these issues a high salt compatible sodium polyacrylate polymer, or other equivalent blood compatible superabsorbent polymers may be added to the reservoir to solidify the blood and wound fluid in the bag. These polymers are available either as loose particles, particles suspended within a dissolvable PVA film pouch or polymer suspended within a textile/fabric like medium. The use of this polymer in tandem with one or more vents on the bag avoids bag inflation and allows the fluid path of the treatment system to cope with much more air as it is introduced into the system.

The pump assembly 2015 includes an inlet and outlet and is driven by a motor. In one embodiment, the pump assembly 2015 may be substantially as described in PCT/NZ2021/050205, comprising a swash plate a plurality of flexible chambers (diaphragms), a plurality of pairs of flexible valves, each pair of valves being in fluid communication with a respective flexible chamber, and a pump inlet and outlet.

The pump assembly 2015 comprises a fluid flow path through the pump from the pump inlet to the pump outlet. In a preferred embodiment the exudate reservoir 2006 is downstream of the pump assembly 2015. This means fluid from the wound passes through the pump assembly 2015.

The pump assembly 2015 preferably comprises a high-capacity pump configured to maintain a negative pressure while introducing significant volumes of air to the treatment system 2100, 2200, 2300 with the air inlet valve 2018 open for a significant time portion of a valve open and close cycle time. A large capacity pump assembly 2015 is required to move the increased amount of air and lift fluid from the wound 62 to the exudate reservoir 2006 while continuing to maintain a negative pressure at the wound 62 at an effective negative treatment pressure level.

The air inlet valve 2018 may include an actuator such as a solenoid in electrical communication with the controller to drive the valve between open and closed positions. The air inlet valve 2018 does not operate as a pressure relief valve, i.e. the air inlet valve is not controlled to 'crack open' to limit a pressure at the wound. The air inlet valve is opened and closed based on a predetermined time period, i.e. the control of the air inlet valve is temporal control, not pressure control, as explained in more detail below.

The fluid inlet valve 2022 may include an actuator such as a solenoid in electrical communication with the controller to drive the valve between open and closed positions.

Dual lumen conduits may be provided for connecting between the vacuum unit 2002 and the treatment device 61. The conduit may have a circular outer wall. This conduit is preferred for wounds treatments where the conduit must be subsequently removed without opening the wound. The round or circular outer wall allows the conduit to be rotated upon removal to gently release tissue adhered to the side of the conduit which can cause discomfort to the patient.

In some alternative embodiments the device 61 could be operably connected to one or more other devices, implanted at different respective sites for treating the respective sites with the same pressure source.

System Operation

Operation of the treatment system 2100 described above with reference to FIGS. 66 and 67 is now described with reference to FIGS. 70 to 80. The system 2100 comprises the user interface 2014 to allow a user to operate the system. The user interface 2014 may provide visual (e.g. LEDs) and audio indication to the user of system settings and allows inputs, for example one or more buttons, for example to turn the unit on/off, operate the pump or select operation modes. The controller provides system logic and control algorithms in electrical communication with the air valve actuator, pump motor and pressure sensor(s) Pv, Pp to control the air inlet valve 2018 and the pump assembly 2015. The controller may also communicate with power management and sensor circuits to manage the power supply, for example to provide a battery charge indication to the user via the user interface.

The controller is configured to operate the pump assembly 2015 to maintain a negative pressure at the wound 62 via the wound treatment device 61 while opening and closing the air inlet valve. The air inlet valve 2018 is opened to introduce air to the wound site while the pump assembly continues to run to maintain a negative pressure at the wound.

Negative pressure treatment can result in a stagnant system, even when the wound continues to produce exudate.

In a stagnant system, the system is effectively sealed from the ambient environment and no fluid transfer or flow is achieved from the wound to the exudate reservoir 2006. This can exacerbate system blockages due to coagulation of blood, fibrin etc at the wound and/or elsewhere in the system. A blockage ultimately results in failure to provide negative pressure at the wound, defeating the negative pressure treatment.

In order to avoid a stagnated system, the controller opens and closes the air inlet valve 2018 while continuing to run the pump assembly 2015 to maintain a negative pressure at the wound.

For example, the treatment system 2100 is configured to open the air inlet valve 2018 to introduce air to the wound site while maintaining a vacuum pressure (a first vacuum pressure) at the wound site 62 wound treatment device 61 of at least 40 mmHg, and preferably at least 50 mmHg. In an example embodiment the treatment system is capable of maintaining vacuum pressure at the wound site/wound treatment device of approximately 50 mmHg to 100 mmHg, or approximately, 60 mmHg to 100 mmHg, or 70 mmHg to 100 mmHg, or 80 mmHg to 100 mmHg, with the air inlet valve open introducing air to the wound. When the controller closes the air inlet valve, the pump continues to operate to maintain negative pressure at the wound. With the air valve closed the vacuum pressure at the wound site 62 may be around 100 mmHg to 150 mmHg (a second vacuum pressure).

Preferably the vacuum pressure maintained at the wound treatment device when the air inlet valve is open is at least a substantial portion of the vacuum pressure maintained at the wound when the air inlet valve is closed, or may be equal to the vacuum pressure maintained at the wound when the air inlet valve is closed. For example, the vacuum pressure maintained at the wound with the air valve open may be approximately 30% to 100% of the vacuum pressure maintained at the wound with the air valve closed, or approximately 50% to 100%, or 70% to 100%, or about 80% of the vacuum pressure maintained at the wound with the air valve closed.

With the air inlet valve closed, the vacuum pressure at the wound may be about 20 to higher than the vacuum pressure at the wound when the air inlet valve is open, or may be equal to the vacuum pressure at the wound when the air inlet valve is open.

In a preferred embodiment the system is configured to cycle the air inlet valve between the open and closed positions while continuing to maintain a negative pressure at the wound. When the air inlet valve is closed the system reverts quickly to a stagnant state. To avoid remaining in a stagnant state that could lead to blockages forming, the controller is configured to again open the air inlet valve while maintaining a negative pressure at the wound, and then again close the air inlet valve. The opening and closing of the air valve continues. The introduce air of into the system while maintaining a negative pressure at the wound promotes movement of fluid from the wound to the reservoir and reduces the risk of blockages. In some embodiments, the treatment system may be configured to continue to open and close the air inlet valve to achieve continuous operation of the pump to maintain fluid flow and avoid remaining in a no-flow or stagnant state for an extended period.

In a preferred embodiment the system is configured so that with the air inlet valve 2018 open, the system achieves an equilibrium state, with a flow rate of air into the treatment system through the air inlet valve 2018 equal to a flow rate of fluid (e.g. exudate) and air through the pump. In an equilibrium state, the vacuum pressure at the wound treatment device 61 is maintained at or reaches a steady state or constant vacuum pressure level (the first vacuum pressure). The system may achieve the constant vacuum pressure level after a short duration, for example several seconds or less, for example 5 second or less. In some embodiments, with the air valve open and in an equilibrium state, the pressure drop across the treatment device is substantially zero, with substantially all of the pressure drop between the system vacuum pressure and ambient pressure occurring across the inlet restriction, provided for example by the air inlet filter. In some embodiments, with the air inlet valve open and in an equilibrium state, the pressure drop across the treatment device is constant. Introducing air to the wound can create a pressure drop across the wound site—between an upstream side of the treatment device and a downstream side of the treatment device—allowing for the transfer of fluid from the wound 62 to the reservoir 2006, to thereby reduce the risk of coagulation and system blockage.

With the air valve closed, the pump is controlled to maintain a negative pressure at the wound and a flow rate from the wound to the pump is proportional to the patient's wound response; i.e. the flow rate is proportional to the exudate produced at the wound. With the air inlet valve closed, the pump is controlled to maintain the vacuum pressure at the wound treatment device at a steady state or constant vacuum pressure level (the second vacuum pressure). Again, the system may achieve the constant vacuum pressure level after a very short duration, for example several seconds or less, for example 5 second or less. As described above, the first vacuum pressure is less than or equal to the second vacuum pressure.

The steady state vacuum pressure at the wound treatment device 61 with the air inlet valve 2018 open may be less than the steady state vacuum pressure at the wound treatment device with the air inlet valve closed. However, the vacuum pressure at the wound treatment device 61 with the air inlet valve open is sufficient for effective negative pressure treatment. As described above, the first vacuum pressure is at least a substantial portion of the second vacuum pressure and may be equal to the second vacuum pressure. Thus, the cyclic opening and closing of the air inlet valve while running the pump to continuously achieve a negative treatment pressure not only improves removal of exudate and reduces the risk of system blockages, but also maintains the negative pressure environment at the wound for effective wound treatment.

Cycling the air inlet valve open and closed while maintaining a negative pressure at the wound achieves a reduced fluid density at the wound site by the introduction of air. Often a height differential exists at the wound site, for example when the patient is upright or in a standing position. A height differential at the wound can result in fluid remaining static in a lowermost location in the wound, with flow in only upper portions of the wound. By introducing air across the wound site, air reaching the lowermost portions of the wound can lift fluid from those lowermost portions and improve fluid movement throughout the wound.

The introduction of air essentially allows the system to operate much like an air pump to allow lower density fluid to move 'uphill' or against gravity.

Figures 70, 71:
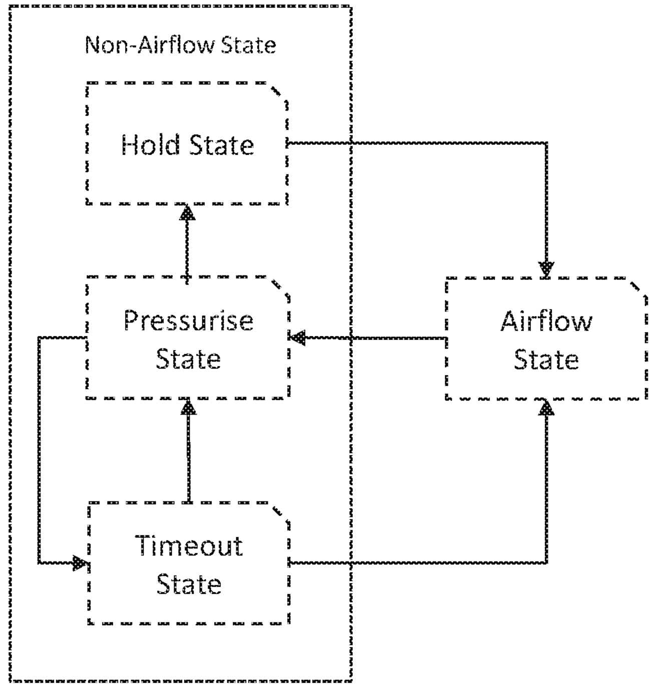
FIG. 70 illustrates various flow characteristics with air entrained in a flow of liquid.
FIG. 71 provides a high-level control flow diagram for various embodiments of negative pressure treatment (NPT) system described herein.

The inventors have additionally identified a preferred mode of operation whereby the air valve is operated between open and closed positions while maintaining a negative pressure at the wound in order to introduce a flow rate of air into the system that achieves a 'bubbly flow' or a 'slug flow' from the wound site to the reservoir. FIG. 70 illustrates a range of flow types in a fluid comprising both liquid and gas states. Introducing to much air due to leaving the air inlet valve open for too long can result in an annular type flow with exudate flowing along the inner wall of the conduit and air flowing through the middle of the conduit. This can cause the exudate to become stagnant on the wall of the conduit which can lead to the fluid solidifying. A layer of solidified fluid can increase over time leading to a blockage. By cycling the air inlet valve open and closed, liquid exudate can reform a uniform column within the flow path of the system when the air valve is closed, with subsequent opening of the air inlet valve to introduce air results in bubbles or slugs of air passing through the exudate. The air valve is again closed before an annular type flow is achieved. The inventors believe that this results in an improved removal of exudate and reduction in blockages.

An example implementation of cycling the air inlet valve between open and closed during NPT is now described with reference to FIGS. 71 to 75. As illustrated in FIG. 71, the controller is configured to implement an airflow mode or state in which the air inlet valve is opened and the pump is operated to achieve a negative pressure at the wound, and a non-airflow mode or state in which the air inlet valve is closed and the pump is operated to achieve a negative pressure at the wound. In the illustrated embodiment the non-airflow state comprises a pressurise state, a hold state and a timeout state.

Figure 72:
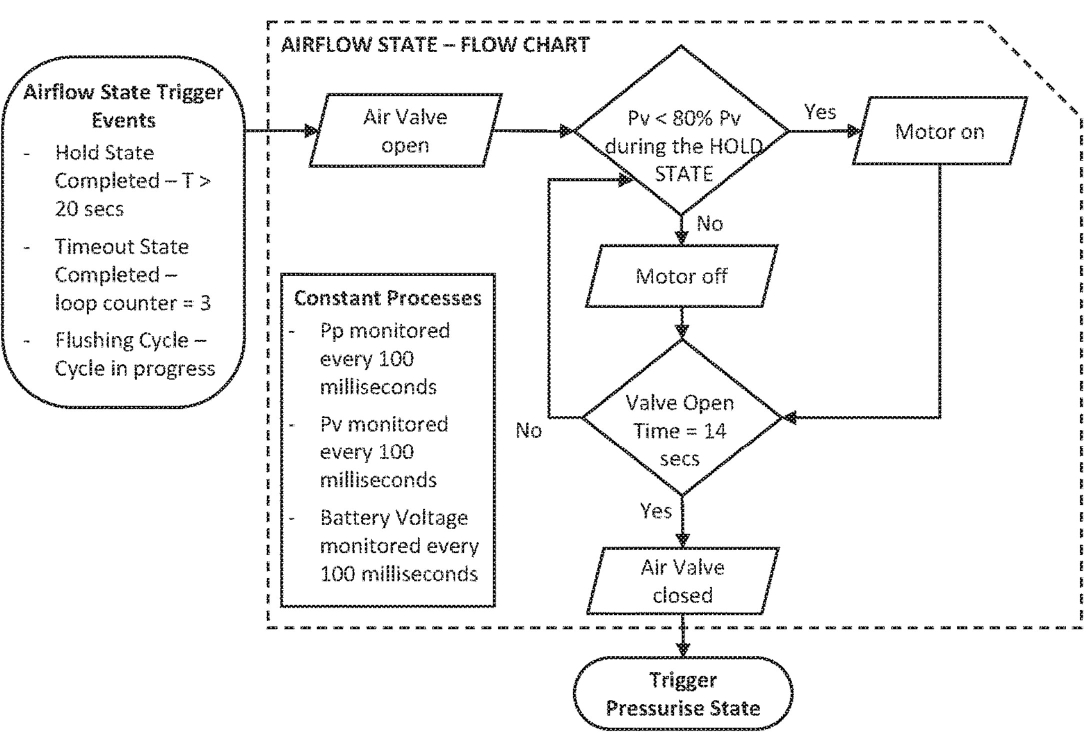
FIG. 72 provides a control flow diagram for an airflow state of the control flow diagrams of FIGS. 71 and 76.
Figure 73:
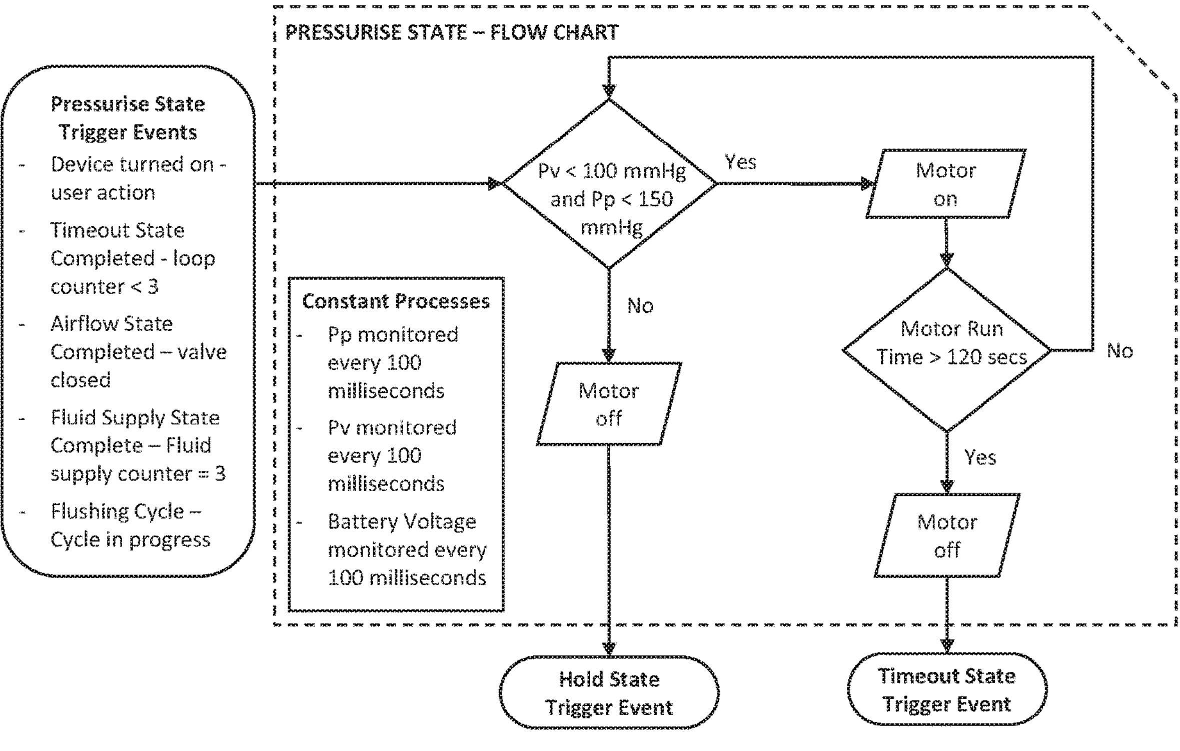
FIG. 73 provides a control flow diagram for a pressurise state of the control flow diagrams of FIGS. 71 and 76.

With reference to FIG. 72, in the airflow state the controller opens the air inlet valve to allow air to enter the system on the upstream side of the treatment device and runs the pump to achieve a pressure threshold. For example, if the pressure sensed by the pressure sensor Pp at the downstream side of the treatment device is less than a pressure threshold, the controller runs the pump (turns the pump on). In other words, if the pressure at Pp is greater than or equal to the threshold pressure, the controller turns the pump off.

In the illustrated embodiment, the pressure threshold at the downstream side of the treatment device (Pp) is a portion of a pressure threshold at the upstream side of the treatment device (Pv) when the air inlet valve is closed. In the illustrated embodiment, the pressure threshold at the downstream side of the treatment device (Pp) is 80% of a pressure threshold at the upstream side of the treatment device (Pv) when the air inlet valve is closed. For example, when the air inlet valve is closed, the pressure threshold at the upstream side of the treatment device at Pv is 100 mmHg, and in the airflow state with the air inlet valve open, the pressure threshold at Pp is 80 mmHg.

The pump may repeatedly turn on and off, e.g. under PID control by the controller, to maintain the vacuum pressure at the downstream side of the wound treatment device with the air inlet valve open. Preferably the system is configured to achieve the threshold pressure at the downstream side of the treatment device at Pp in a very short time period, i.e. within several seconds or less, for example 5 second or less. The air inlet valve remains in the open position for a time period. When the air inlet valve is open, the pressure at the wound is maintained constant. In the illustrated embodiment, the air inlet valve remains in the open position for 14 seconds. Once 14 seconds has elapsed, the controller closes the air inlet valve and the controller moves to the pressurise state of the non-airflow state.

The parameters of the above described airflow state are provided by way of example. In some embodiments, the system may be without the pressure sensor Pp on the downstream side of the treatment device. The pump may be provided with a suitable capacity such that the pump is run at a predetermined rate corresponding with a particular system performance to achieve a known or acceptable pressure level at the wound treatment device (the first vacuum pressure) with the air inlet valve open. Additionally, or alternatively, the system may include a pressure relief valve to introduce air to the system at the pump inlet to ensure the vacuum pressure generated by the pump does not increase too high. However, in the preferred embodiment the system includes pressures sensor Pp and the controller operates the pump so that the pressure does not increase beyond a predetermined pressure threshold, being 80 mmHg in the above example. Other pressure thresholds are possible depending on a desired treatment regime. Preferably the controller implements PID control to achieve accurate control of the pump and therefore control of the vacuum pressure at the wound. The controller may use a pulse-width modulation (PWM), or pulse-duration modulation, method in the control of the pump motor.

As shown in FIGS. 66 to 69, in the example embodiments the pressure sensor Pv is on an ambient side of the filter. The sterile filter 2019 presents a known pressure drop to prevent the vacuum pressure at the treatment device collapsing to ambient pressure when the air inlet valve is open. With the pressure sensor Pv on the ambient side of the filter the sensor Pv essentially measures ambient pressure when the air inlet valve is open. Thus, when the air inlet valve is open, the pressure sensed by sensor Pv is not used in the control of the pump, the pump will run until the pressure sensed by Pp increases above the pressure threshold. In some embodiments, the pressure at Pp will not reach the pressure threshold when the valve is open. The pump may run continuously when the air inlet valve is open, however this is less preferred.

Figure 77:
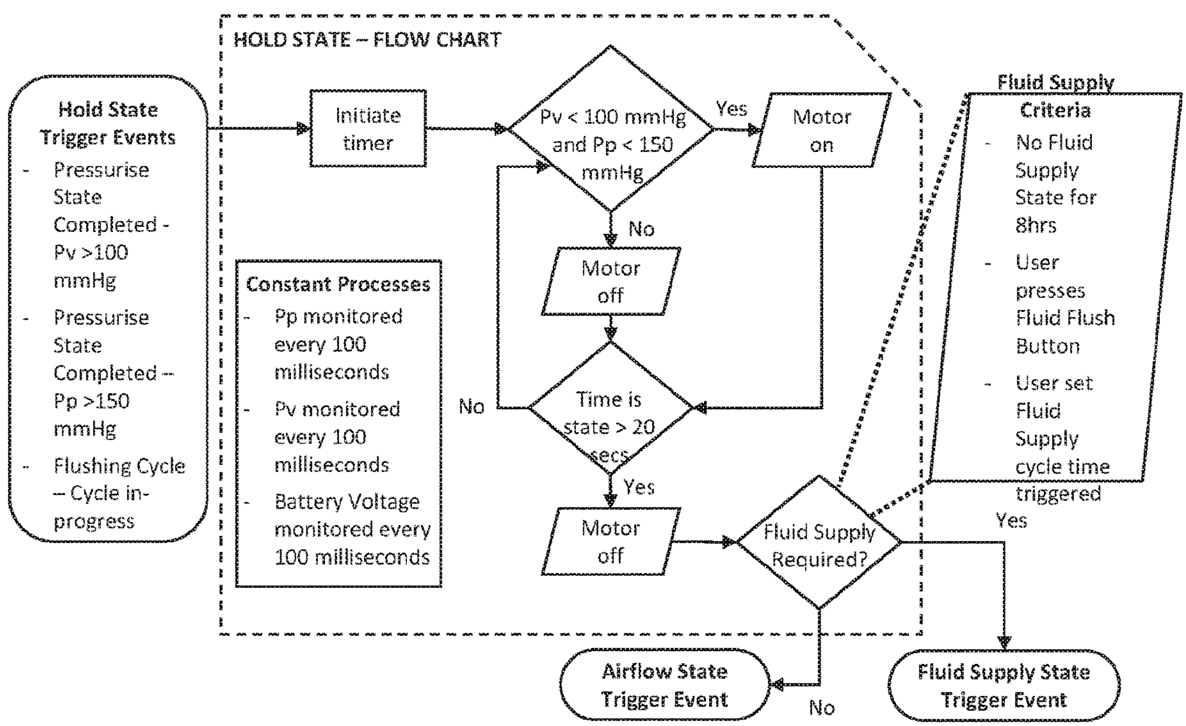
FIG. 77 provides a control flow diagram for a hold pressure state of the control flow diagram of FIG. 76.

With reference to FIG. 77, in a pressurise state, the air inlet valve is closed, and the controller runs the pump to achieve a pressure threshold to achieve a known or acceptable vacuum pressure at the wound treatment device (the second vacuum pressure). With the air valve closed the vacuum pressure at the wound treatment device may be increased compared to the vacuum pressure achieved in the airflow mode. In the illustrated embodiment, if the pressure sensed by the pressure sensor Pv at the upstream side of the treatment device is less than a 100 mmHg, and the pressure sensed by the pressure sensor Pp at the downstream side of the treatment device is less than 150 mmHg, the controller runs the pump. In other word, if the pressure Pv is greater than or equal to 100 mmHg or pressure Pp is greater than or equal to 150 mmHg, the controller turns the pump off.

The system may be configured to achieve the threshold pressure after a very short duration of closing or opening the air inlet valve, i.e. within several seconds or less, for example 5 second or less. With the air valve closed, since the system is closed or sealed, the system reaches a stagnant or no flow condition very quickly with zero pressure drop across the treatment device and therefore with the pressure at Pv=the pressure at Pp. In the illustrated embodiment, since the pressure threshold at Pv is less than the pressure threshold at Pp, the controller controls the pump based on the upstream pressure sensor Pv, the lower of the two pressure thresholds. However, a pressure drop through the system may occur when tissue debris and/or solidifying materials such as fibrin accumulate within the would treatment device and/or the pump, in which case a pressure differential may develop between the upstream and downstream sides of the treatment device as measured by sensors Pv and Pp. System restrictions may cause the system pressure to reach the higher threshold at the downstream side of the treatment device, before the lower threshold is reached at the upstream side of the treatment device, in which case the pump is controlled based on the downstream pressure sensor Pp to the higher pressure threshold at Pp.

Once the pressure threshold has been reached the controller turns the pump off and moves into a hold state. The pressurise state includes a time-out check so that if the pump has not achieved the pressure threshold (e.g. at Pp) within 120 seconds the motor is turned off and the controller moves to a time out state. This may occur for example due to a blockage within the system or other failure mode, such as a leak.

Figure 74:
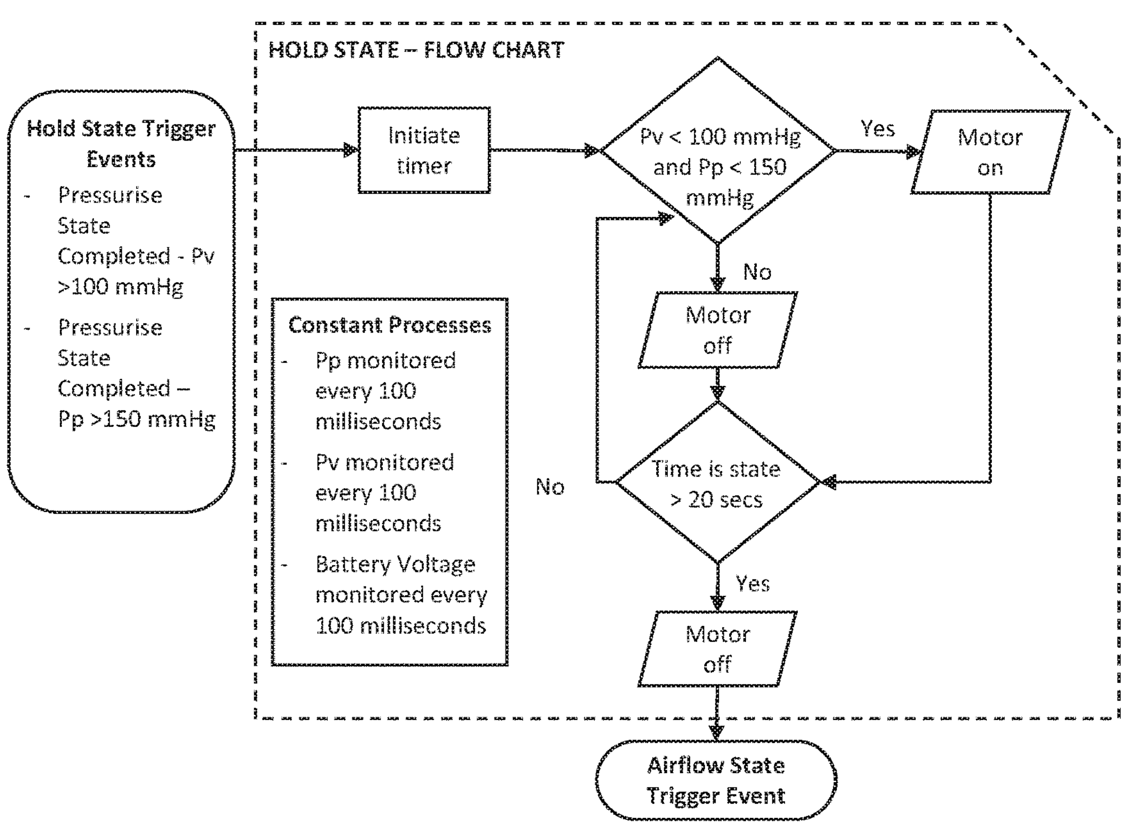
FIG. 74 provides a control flow diagram for a hold pressure state of the control flow diagram of FIG. 67.

With reference to FIG. 74, in a hold state the controller maintains the air inlet valve in the closed position and continues to operate the pump to maintain the desired or acceptable vacuum pressure at the wound treatment device, by turning the pump on and off, for example under PID control to achieve a desired pressure threshold at Pv or Pp. The controller maintains the vacuum pressure with the air inlet valve shut for a time period. In the illustrated embodiment, the air inlet valve is closed for 20 seconds. Once 20 seconds has elapsed, the controller returns to the air flow mode and the cycling of the opening and closing of the air inlet valve is repeated. The opening and closing of the air inlet valve may be cycled continuously to achieve the above described benefits.

The above example implementation provides an air inlet valve open time of 14 second and an air inlet valve close time of 20 seconds. These time periods are by way of example and alternative time periods may be implemented. However, it is to be noted that the air inlet valve is open for a substantial portion of a total open/close cycle. In this embodiment, the total open/close cycle, or the 'cycle pitch' is 34 seconds, with the air inlet valve open for 14 second of the 34 second period, or around 40% of the total cycle. In some embodiments, the air inlet valve is open for at least 10% of the cycle pitch, or at least 20% of the cycle pitch, or at least 30% of the cycle pitch, or at least 40% of the cycle pitch. For example, the air inlet valve open time period may be around the same as the close time period (50% of the cycle pitch). In some embodiments, the air inlet valve may be open for more than 50% of the total cycle.

The above example system configuration provides a cycle time of 34 seconds. However longer or shorter cycle times are possible. As described above, the opening and closing of the air inlet valve required to achieve a slug or bubbly flow from the would site to the reservoir while maintaining negative pressure at the wound is ideal. A maximum valve cycle time may be 1 minute or several minutes. However, the air inlet valve should be open for at least approximately 10 seconds at the above pressures to ensure sufficient air is introduced to the system. The air inlet valve may be open for 10 to 40 second in each air inlet valve open/close cycle.

The time periods for which the air inlet valve is open and closed is dependent on the air inlet flow restriction, the pump capacity, the treatment device configuration and the supply and exudate conduit length and diameter. The above described system components and control parameters are provided by way of example. However, the inventors believe that the system parameters should be selected to enable the air inlet valve to be open for a significant duration while maintaining the negative pressure at the wound at a level useful in the negative pressure treatment of a wound.

Figure 75:
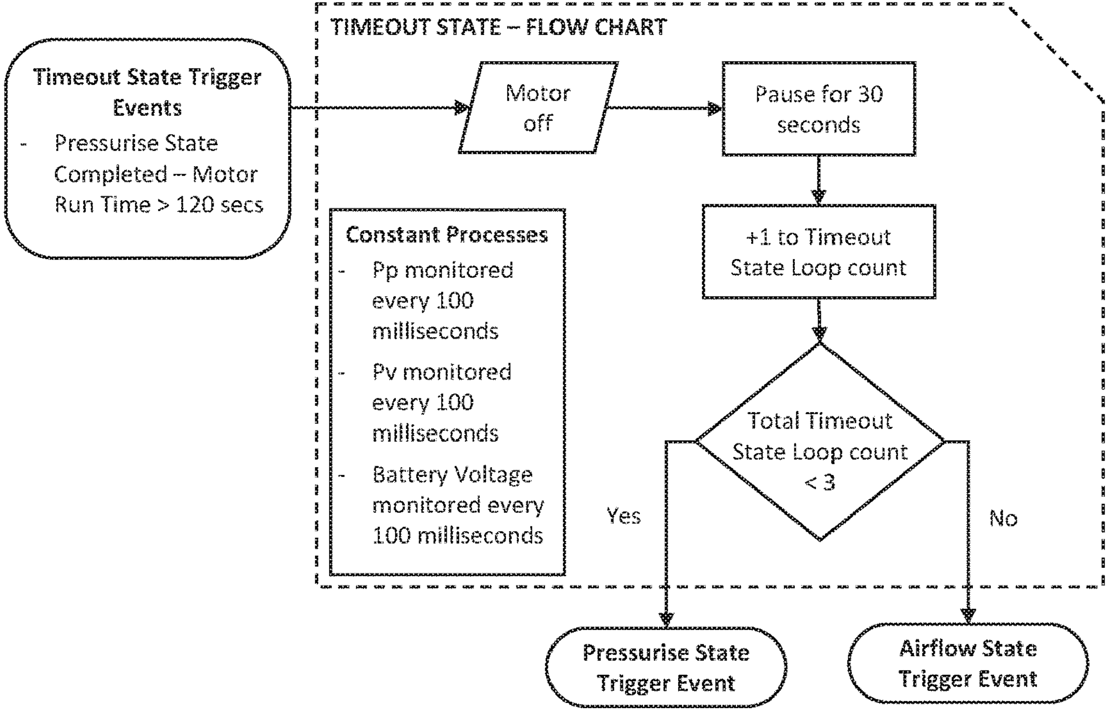
FIG. 75 provides a control flow diagram for a timeout state of the control flow diagrams of FIGS. 71 and 76.

With reference to FIG. 75, the example embodiment includes a time out state to safely manage a situation whereby the system is unable to reach an intended negative pressure level. As described above with reference to FIG. 73, if the system is unable to pressurise when the air inlet valve is closed after a predetermined time period (for example 2 minutes) the controller enters the time out state. The controller pauses the pump operation for 30 second and increments a timeout counter. If the time out counter is less than a predetermined count threshold, the controller then returns to the pressurise state to try and pressurise the wound treatment site. If the timeout counter threshold is reached, the controller returns to the air flow state. As described above, introducing air can reduce blockages. The system may have failed to pressurise due to a blockage. Returning to the air flow state may remove a blockage before returning to the pressurise state.

In some embodiments, the treatment system may implement other control parameters not presented in FIGS. 71 to 75. For example, in some embodiments, the system comprises the pressure sensor Pv on the upstream side of the treatment device and the pressure sensor Pp on the downstream side of the treatment device. The controller may operate the pump and/or air inlet valve based on a pressure differential measured between the two pressure sensors. For example, the controller may open the air inlet valve when the pressure differential increases above an upper threshold or is above an upper threshold for a predetermined time period. A system pressure differential may be indicative of a blockage in the system, especially when the air inlet valve is closed. With the air valve closed and with the system in a stagnant state, the pressure on the upstream and downstream sides of the treatment device should be substantially equal. The controller may close the air valve when the pressure differential decreases below a lower threshold or is below a lower threshold for a predetermined time period. The controller may stop the pump and/or the airflow state when the pressure differential increases above an upper or maximum threshold.

As described above with reference to FIGS. 68 and 69, in some embodiments the system is configured to introduce a treatment fluid to the wound. For the system of FIG. 68, the controller may be configured to operate the treatment fluid inlet control valve 2022 to introduce treatment fluid in a similar way to operation of the air inlet valve 2018. The treatment fluid reservoir 2026 is preferably at ambient pressure.

The controller opens the fluid inlet valve 2022 while operating the pump to maintain a negative pressure at the wound treatment device, to draw treatment fluid into the treatment device. In a preferred embodiment, the system is configured so that with the fluid inlet valve 2022 open, the system achieves an equilibrium state, with a flow rate of treatment fluid into the treatment system from the treatment fluid reservoir 2026 is equal to a flow rate of fluid (e.g. exudate and treatment fluid) through the pump. In an equilibrium state, the vacuum pressure at the wound treatment device is maintained at or reaches a steady state or constant vacuum pressure level (i.e. a third vacuum pressure). The system may achieve the constant vacuum pressure level after a very short duration, for example several seconds or less, for example 5 second or less. In a preferred embodiment, with the fluid inlet valve open and in an equilibrium state, the pressure across the treatment device is substantially zero.

When the fluid inlet valve is open, the controller may operate the pump to achieve the same pressure at the treatment device that the treatment system achieves when the air inlet valve is open.

With the fluid inlet valve closed, the pump is controlled to maintain a negative pressure at the wound. With the fluid inlet valve closed, the pump may be controlled to maintain the vacuum pressure at the wound treatment device at a steady state or constant vacuum pressure level (a fourth vacuum pressure). Again, the system may achieve the constant vacuum pressure level after a very short duration, for example several seconds or less, for example 5 second or less. When the fluid inlet valve is closed, the controller may operate the pump to achieve the same pressure at the treatment device that the treatment system achieves when the air inlet valve is closed.

The steady state vacuum pressure at the wound treatment device with the fluid inlet valve open may be less than the steady state vacuum pressure at the wound treatment device with the fluid inlet valve closed. However, the vacuum pressure at the wound treatment device with the fluid inlet valve open is sufficient for effective negative pressure treatment.

The treatment fluid is not introduced under a positive pressure. Thus, the opening and closing of the fluid inlet valve while running the pump to continuously achieve a negative treatment pressure not only maintains the negative pressure environment at the wound for effective treatment but also provides for the installation of treatment fluid to improve treatment, the removal of exudate, and reduce the risk of system blockages.

The amount of treatment fluid administered to the system can be controlled based on the time the fluid inlet valve is open. A flow restriction (such as a constricting orifice) may be placed between the treatment fluid reservoir 2026 and the Pv pressure sensor positioned upstream of the wound treatment device. The resultant pressure drop across this restriction can allow the rate of fluid to be determined from the resulting pressure drop measured by the sensor Pv and the total amount of treatment fluid administered to be calculated. Alternatively, the treatment fluid inlet valve may be open until a differential pressure threshold is achieved or achieved for a time period, or the valve may be opened for a predetermined time period. The treatment fluid inlet valve is preferably opened when the air inlet valve is closed.

With reference to the embodiment of FIG. 69, the system is without a treatment fluid inlet valve controlled by the controller. The system administers treatment fluid during negative treatment pressure since the vacuum pressure at the wound draws the ambient treatment fluid into the system. When the air valve is open, air flows to the treatment device, and the flow of air into the system tends to stop the flow of fluid from the treatment fluid reservoir due to the much lower density of the air compared to the density of the treatment fluid. When the air inlet valve is closed, the negative pressure at the wound draws fluid from the treatment fluid reservoir into the system and flood into the wound. Treatment fluid passes through the treatment device and wound and through the pump to the reservoir as the pump maintains a vacuum pressure at the wound. Reopening the air valve again stops the flow of treatment fluid and causes a pressure differential to move fluid comprising treatment fluid and exudate from the wound. Thus, cycling the air inlet valve can also achieve addition and removal of treatment fluid to and from the wound in a cyclic manner. The amount of treatment fluid added is dependent on how long or how much air has been introduced. The amount of treatment fluid introduced to the system may be proportional to an amount of air introduced to the system.

Figure 76:
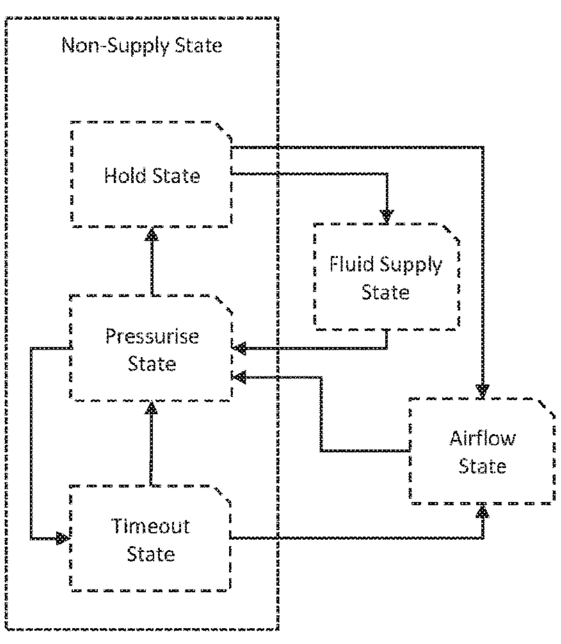
FIG. 76 provides a high-level control flow diagram for various embodiments of a NPWT system described herein.

An example implementation of the system of FIG. 68 is now described with reference to FIGS. 76 to 79. As illustrated in FIG. 76, the controller is configured to implement a fluid supply mode or state in addition to the airflow state described above. The controller implements a non-supply/non-airflow mode in which the air inlet valve and the treatment fluid valve are closed and the pump is operated to achieve a negative pressure at the wound. In the illustrated embodiment the non-airflow state comprises a pressurise state, a hold state and a timeout state.

The air flow state and pressurise state of FIG. 76 are as described above with reference to FIGS. 72 and 73. Once the airflow state and pressurise state of FIGS. 68 and 69 have been run the controller implements the fluid supply hold state of FIG. 77.

With reference to FIG. 77 in the hold state the controller maintains the air inlet valve in the closed position and continues to operate the pump to maintain the desired or acceptable vacuum pressure at the wound treatment device, by turning the pump on and off, for example under PID control to achieve a desired pressure threshold (at Pp and/or Pv). The controller maintains the vacuum pressure with the air inlet valve shut for a time period, e.g. 20 seconds. Once 20 seconds has elapsed, the controller turns the pump off and checks to see if the fluid supply state is required. If the fluid supply state is not required, the controller returns to the air flow mode and the cycling of the opening and closing of the air inlet valve is repeated as described above with reference to FIG. 71. The controller implements the fluid supply state if no treatment fluid supply has been provided for a predetermined time period, for example 8 hours, or a user set fluid supply cycle time is triggered, or if a user manually requests a fluid supply, for example by pressing a button on the user interface of the vacuum unit.

The time period between activating the fluid supply state is much greater than the air inlet valve open and close cycle time period. For example, the air inlet valve cycle time period may be less than 1 minute and the time period between fluid supply states may be more than 1 hour With reference to FIG. 78, in the fluid supply state the controller opens the fluid valve to allow the treatment fluid to flow from the treatment fluid reservoir to the upstream side of the treatment device and runs the pump to achieve a pressure threshold. If the pressure sensed by the pressure sensor Pv at the upstream side of the treatment device is less than 100 mmHg, and the pressure sensed by the pressure sensor Pp at the downstream side of the treatment device is less than 150 mmHg, the controller runs the pump. The control of the pump when the treatment fluid valve is open may be the same or similar to the pump control when the air inlet valve is open as described above. In the illustrated example the controller maintains the fluid valve open for 10 seconds, however other time periods are possible. The controller closes the fluid valve and may allow for a fluid contact dwell time to allow the fluid introduced to the wound to flood or remain in the wound site for a set period of time. The controller may allow for a user input to set the dwell time of between 0 minutes to 10 minutes or other time period. Following the delay to allow fluid contact within the wound the controller enters a flushing cycle to flush the treatment fluid from the wound. In the illustrated embodiment the controller repeats the flushing cycle three times, however the controller may perform the flushing cycle once, twice or more than three times. In the illustrated embodiment the controller repeats the fluid supply state three times before returning to the pressurise state, however the controller may perform the fluid supply state once, twice or more than three times.

Figure 78:
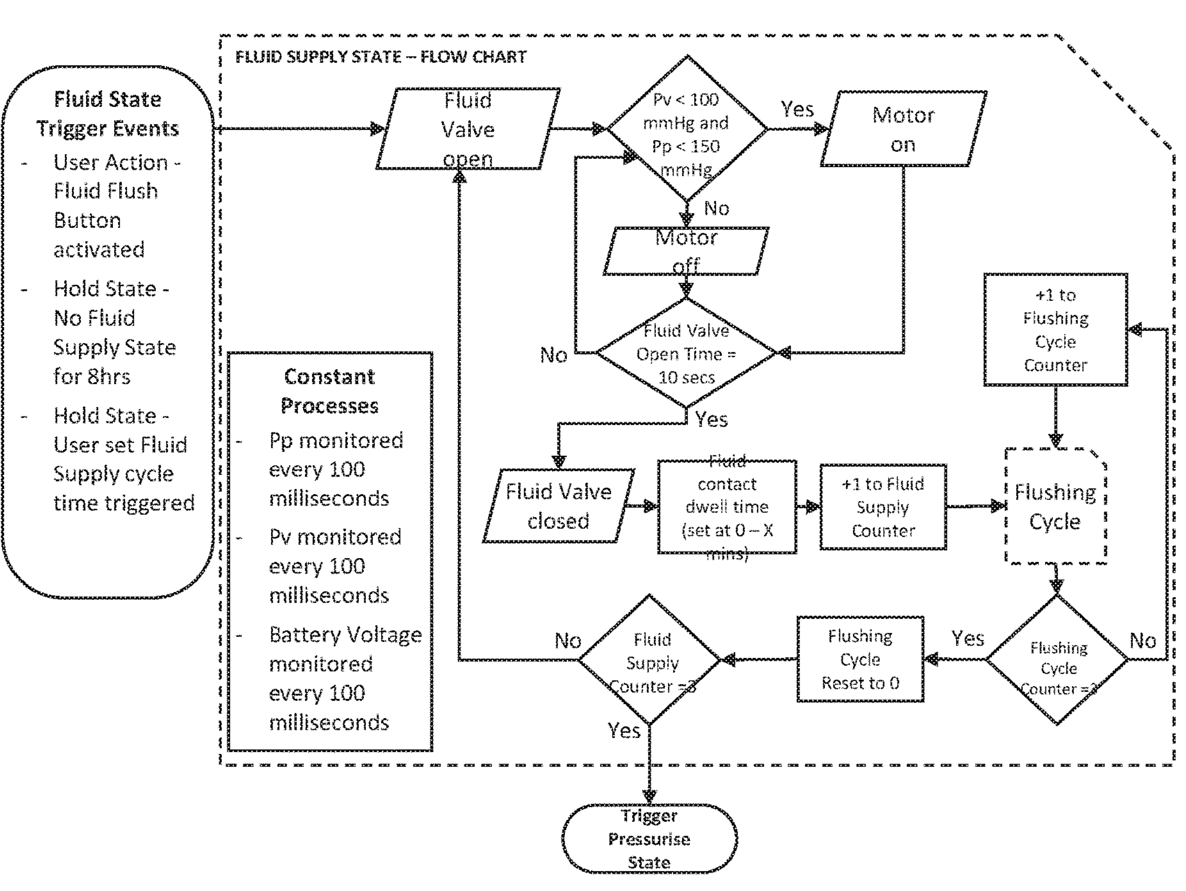
FIG. 78 provides a control flow diagram for a fluid flow state of the control flow diagram of FIG. 76.
Figure 79:
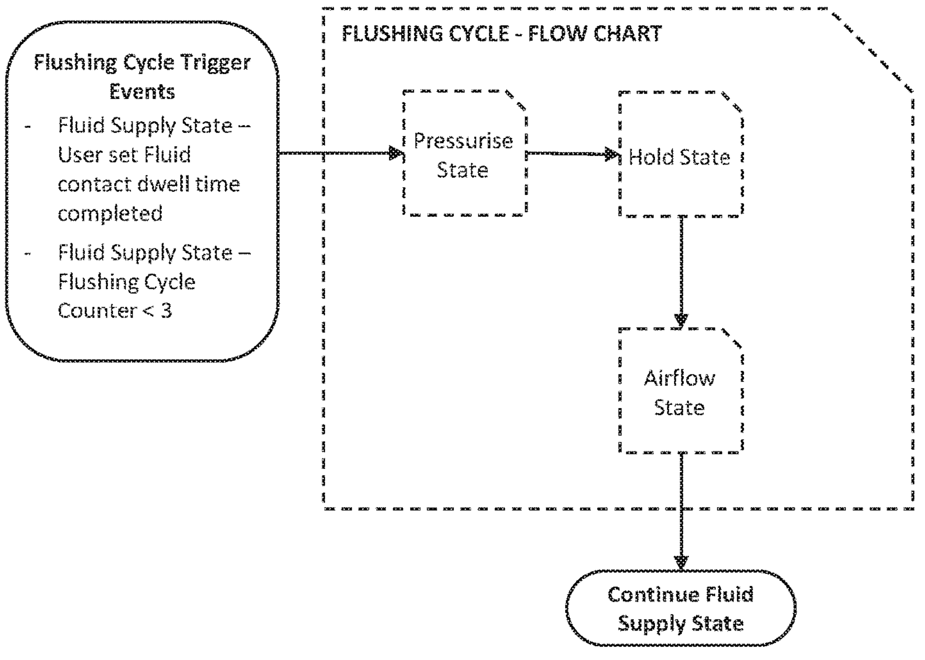
FIG. 79 provides a control flow diagram for a flushing cycle of the fluid flow state of FIG. 76.
Figure 80:
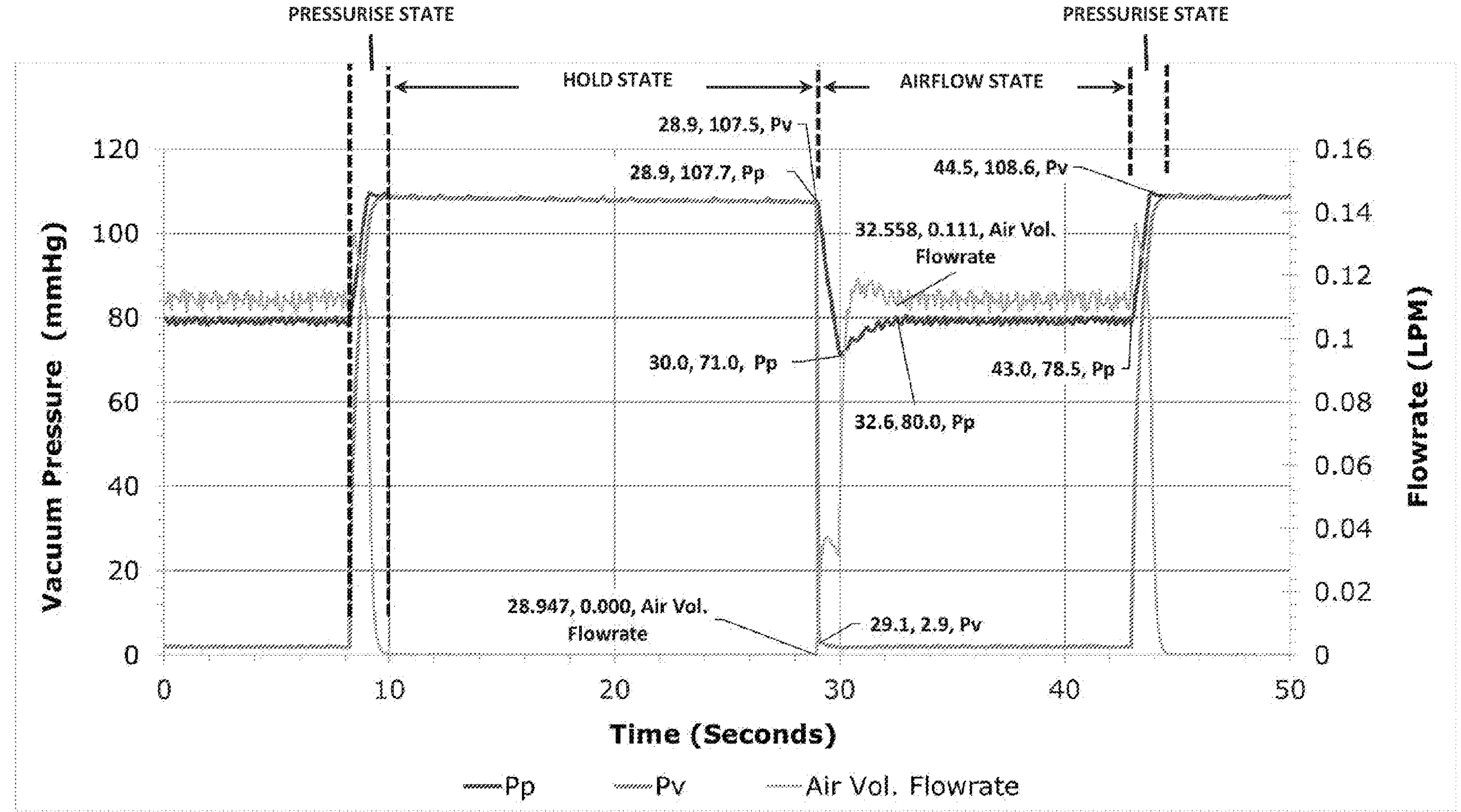
FIG. 80 provides a chart showing system performance of a treatment system test set-up.

With reference to FIG. 79, in the flushing cycle the controller steps through the pressurise state, hold state and airflow state as described above with reference to FIGS. 73 and 74, before continuing with the fluid supply state to repeat the fluid supply state to open the fluid valve again if required as shown in FIG. 78. At the conclusion of the fluid supply state the controller returns to the pressurise state of FIG. 73. The system continues to pressurise, hold pressure and cycle the air inlet valve open and closed as described above.

In the illustrated embodiment, the fluid inlet valve is open for 10 seconds and closed for 102 seconds in each open and close cycle of the fluid inlet valve. The close time is dependent on the dwell time and the combined flushing cycle run time. In the illustrated embodiment, the fluid supply state includes three flushing cycles. With each flushing cycle requiring 34 seconds, and for an example dwell time of zero, in the illustrated example the fluid supply valve is closed for a total of 102 seconds. In the illustrated example the fluid inlet valve is open for around 10% of the cycle pitch. The fluid inlet valve may be open for at least 5% of the cycle pitch, or at least 10% of the cycle pitch, or at least 20% of the cycle pitch.

The fluid supply and flushing states provides a treatment fluid to the wound while maintaining a negative pressure and flushes the treatment fluid from the wound using the introduction of air to remove the fluid and exudate from the wound. As described above, a number of treatment fluid flushes may be provided. This procedure reduces stagnated fluid in the wound, thereby reducing blockages in the system and ensure negative pressure to be continually applied to the wound site.

The operation of the system 2100, 2200, 2300 may be via the user interface 14, which enables a user to selectively operate the system. The user interface may provide visual (e.g. LEDs) and/or audio indication to the user to communicate system settings. The user interface 14 may includes several buttons to initiate or cease the delivery of negative pressure to the connected wound treatment device 61, turn the unit power on or off, silence the audible alarm and/or connect the device to a remote wireless receiving device to transmit data regarding the operation or status of the system.

The controller may provide system logic and control algorithms in electrical communication with the actuator for the air valve 2018, the actuator for the dressing control valve 2029, the motor of the pump 2015, and pressure sensors Pv, Pp. The controller 2017 is configured to control the air inlet valve 2018, and the pump assembly 2015 based on the readings at the pressure sensors Pv, Pp. The controller may also communicate with power management and sensor circuits to manage the power supply or provide battery level warning alarm.

The controller 2017 is configured to operate the pump assembly 2015 to maintain a negative pressure at the internal wound 62 via the implanted wound treatment device 61 while opening and closing the air inlet valve 2018. The air inlet valve 2018 is opened to introduce air to the wound site while the pump assembly continues to run to maintain a negative pressure at the wound as described elsewhere within this specification.

Negative pressure treatment can result in a stagnant system that can exacerbate system blockages due to coagulation of blood, fibrin etc at the wound and/or elsewhere in the system. A blockage can ultimately result in failure to provide negative pressure at the wound, reducing the effectiveness of the negative pressure treatment.

The controller may be configured to adapt to anticipated changes that can occur system in response to the changes occurring at the wound treatment site 62 and implanted treatment device 61. As the treatment device is subjected to repeated cycles through the pressurise, hold and airflow state it has been discovered that a pressure differential between the Pv and Pp pressure sensors can occur in response to changes in the treatment site 62 and/or implanted wound treatment device 61 as a result of tissue in-growth, accumulation of wound debris and many other factors.

In response to these dynamic changes the system adjusts the target pressure level being applied at the Pv pressure sensor during the pressure site to compensate for the changes in the treatment device 61. For example, if the motor has stopped as a result of the Pp pressure sensor being above 150 mmHg the system may be configured drop the target vacuum pressure level from for example, the Target 1 (100 mmHg) pressure being applied at the Pv pressure sensor by 10 mmHg to a Target 2 pressure of 90 mmHg before advancing to the hold state. If the pressure drop across the implanted treatment device 61 increases again the system will continue to drop the target level by one step until the Pv pressure level reaches a pressure below 60 mmHg (Target 5).

| Pv Target Level | Pressure Level |
|---|---|
| Target 1 | Pv = 100 mmHg |
| Target 2 | Pv = 90 mmHg |
| Target 3 | Pv = 80 mmHg |
| Target 4 | Pv = 70 mmHg |
| Target 5 | Valve closed |

Once the pressure level measured at the Pv pressure sensor reaches this level the system will then halt the transition from the hold state to the airflow state which will revert the system to a continuous vacuum pressure level system.

If the vacuum pressure level at Pv returns to 90 mmHg (Target 2), following a drop to below (Target 5) during the hold state, the system will resume the advancement to the airflow state where the cycling between hold, airflow and pressurise will resume.

A system as described herein may provide significant benefits, including but not limited to one or more of the following:

- Improved fluid removal from the wound site, providing improved healing benefits such as reduced edema by the removal of excess exudate;
- Reduced risk of blockages forming in the system;
- Maintaining effective negative pressure at the wound even during addition of air to ensure effective treatment;
- Removal of exudate from a lower portion of a wound where there is a height differential at the wound;
- Low power consumption suited for application in portable wound treatment systems;
- Application of treatment fluids to the wound while maintaining effective negative pressure at the wound to ensure effective treatment;
- Provision of negative pressure to a larger portion of a treatment space to improve treatment throughout the entire treatment space;
- System configurability with and without the provision of a treatment fluid supply to the wound;
- Ease of providing a sterile interface between an air inlet and a wound site.

Although the invention has been described by way of example, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A bioresorbable device for implantation in the body of a patient for administering fluid and/or negative pressure to a treatment site, the device comprising a bioresorbable resilient truss for holding two tissue surfaces spaced apart, the truss comprising:

two flexible elongate wall members wound in a manner to define a channel, the two elongate wall members intersecting each other periodically at a plurality of cross-over nodes; and at least two flexible elongate bracing members, wherein each bracing member loops around the wall members or the wall members loop around the respective bracing member to mechanically link and fixably interlock each bracing member to each of the two elongate wall members at a plurality of the cross-over nodes.

2. A device as claimed in claim 1, wherein the bracing members extend generally longitudinally along a side of the channel.

3. A device as claimed in claim 2, wherein the bracing members are provided on opposite sides of the channel.

4. A device as claimed in claim 1, wherein the wall members are wound to form a porous wall such that fluid from the treatment site can drain from the channel and/or fluid can be delivered to the treatment site from the channel.

5. A device as claimed in claim 1, wherein the device is generally tubular.

6. A device as claimed in claim 1, wherein each bracing member comprises a main filament that forms a full 360 degree loop around the wall members at the respective cross-over nodes.

7. A device as claimed in claim 6, wherein each bracing member main filament loops 720 degrees around the wall members at the respective cross-over nodes.

8. A device as claimed in claim 6, wherein each bracing member further comprises a secondary filament that twists around the main filament.

9. A device as claimed in claim 1, wherein each bracing member comprises two filaments twisted together, with the wall members held between the two filaments at the respective cross-over nodes.

10. A device as claimed in claim 9, wherein there is at least one full twist of the filaments between adjacent interlinked cross-over nodes.

11. A device as claimed in claim 1, wherein each bracing member is mechanically linked and fixably interlocked to the two elongate wall members at the respective cross-over nodes by way of the wall members looping around the respective bracing member.

12. A device as claimed in claim 1, wherein each elongate wall member is generally helical.

13. A device as claimed in claim 12, wherein a first one of the wall members is generally helical with a first pitch length, and a second one of the wall members is generally helical with a second pitch length that is the same as the first pitch length.

14. A device as claimed in claim 12, wherein the two wall members are oppositely wound.

15. A device as claimed in claim 12, wherein each wall member has a pitch length that is between about 2 mm and about 10 mm.

16. A device as claimed in claim 15, wherein each wall member has a pitch length of about 4 mm.

17. A device as claimed in claim 1, wherein a first one of the wall members is a left-side wall member, and a second one of the wall members is a right-side wall member.

18. A device as claimed in claim 1, wherein the wall members and bracing members comprise suture.

19. A device as claimed in claim 1, wherein the truss forms a flexible tube having a round or oval cross-section.

20. A device as claimed in claim 19, wherein the channel has a cross-sectional area of at least 16 $mm^2$.

21. A device as claimed in claim 1, further comprising a flexible bioresorbable sheet, the sheet forming at least a portion of a wall of the channel.

22. A device as claimed in claim 21, wherein the flexible bioresorbable sheet is wrapped around the truss.

23. A device as claimed in claim 22, comprising a plurality of apertures in the flexible bioresorbable sheet to permit fluid flow into the channel.

24. A device as claimed in claim 21, comprising two flexible bioresorbable sheets, wherein the channel is formed between facing surfaces of the two flexible sheets.

25. A device as claimed in claim 24, comprising a plurality of apertures in one or both flexible sheets along a wall of the channel to permit fluid flow into the channel.

26. A device as claimed in claim 21, wherein the flexible sheet comprises one or more layers of extracellular matrix (ECM) or polymeric material.

27. A device as claimed in claim 26, wherein the ECM is formed from decellularised propria-submucosa of a ruminant forestomach.

28. A device as claimed in claim 1, comprising a port in fluid communication with the one or more channels and being connectable to a source of negative pressure or positive pressure.

29. A device as claimed in claim 1, wherein the treatment site is a space between surfaces of muscle tissue, connective tissue or skin tissue that have been separated during surgery or as a result of trauma.

30. A device as claimed in claim 1, wherein each bracing member loops around the wall members or the wall members loop around each bracing member to mechanically link and fixably interlock both bracing members to both of the two elongate wall members at a plurality of the cross-over nodes.

31. A device as claimed in claim 30, wherein each bracing member loops around the wall members or the wall members loop around each bracing member to mechanically link and fixably interlock both bracing members to both of the two elongate wall members at each of the plurality of cross-over nodes.

32. A device as claimed in claim 30, wherein each bracing member loops around the wall members or the wall members loop around each bracing member to mechanically link and fixably interlock both bracing members to both of the two elongate wall members at a plurality of the cross-over nodes to prevent or minimize relative movement between said elongate wall members and to prevent or minimize movement of each bracing member relative to the cross-over node.

33. A system for draining fluid from a treatment site or delivering fluid to a treatment site in the body of a patient comprising:

(i) a device as claimed in claim 1;

(ii) a conduit releasably coupled to either the port of the device or to a fluid impermeable dressing;

(iii) a reservoir located external to the body of the patient, the reservoir in fluid communication with the conduit for receiving fluid from the conduit or delivering fluid to the conduit; and (iv) a source of pressure coupled to the conduit for delivering positive pressure or negative pressure to the device.

34. A system as claimed in claim 33, wherein the source of pressure is capable of delivering negative pressure to the device so that fluid is drained from the treatment site into the device and transferred through the conduit to the reservoir.

35. A system as claimed in claim 34, wherein the negative pressure source is arranged to draw a treatment fluid through the device.

36. A method of draining fluid from a treatment site or delivering fluid to a treatment site in the body of a patient comprising:

(i) implanting a device of claim 1 at the treatment site;

(ii) coupling a conduit to the device, the conduit being connected to at least one reservoir located external to the body of the patient for receiving fluid from the conduit or delivering fluid to the conduit; and (iii) delivering negative pressure to the device so that fluid from the treatment site is drawn into the device for removal and/or so that treatment fluid is drawn into the device and delivered to the treatment site.

* * * * *